(12) United States Patent
Ren et al.

(10) Patent No.: US 11,744,898 B2
(45) Date of Patent: Sep. 5, 2023

(54) MULTI-ARM POLYMER CONJUGATES OF TLR AGONIST COMPOUNDS AND RELATED IMMUNOTHERAPEUTIC TREATMENT METHODS

(71) Applicant: Nektar Therapeutics, San Francisco, CA (US)

(72) Inventors: Zhongxu Ren, Foster City, CA (US); Neel K. Anand, San Mateo, CA (US); Haiying Cai, Cupertino, CA (US); Bo-Liang Deng, San Ramon, CA (US); Bhalchandra V. Joshi, Madison, AL (US); Jonathan Zalevsky, Berkeley, CA (US); Takahiro Miyazaki, San Francisco, CA (US); Saul Kivimae, San Francisco, CA (US)

(73) Assignee: Nektar Therapeutics, San Francisco, CA (US)

( * ) Notice: Subject to any disclaimer, the term of this patent is extended or adjusted under 35 U.S.C. 154(b) by 628 days.

(21) Appl. No.: 16/475,972

(22) PCT Filed: Jan. 10, 2018

(86) PCT No.: PCT/US2018/013199
§ 371 (c)(1),
(2) Date: Jul. 3, 2019

(87) PCT Pub. No.: WO2018/132496
PCT Pub. Date: Jul. 19, 2018

(65) Prior Publication Data
US 2021/0128737 A1    May 6, 2021

Related U.S. Application Data

(60) Provisional application No. 62/510,019, filed on May 23, 2017, provisional application No. 62/510,024, filed on May 23, 2017, provisional application No. 62/488,407, filed on Apr. 21, 2017, provisional application No. 62/488,251, filed on Apr. 21, 2017, provisional application No. 62/467,945, filed on Mar. 7, 2017, provisional application No. 62/444,735, filed on Jan. 10, 2017, provisional application No. 62/444,756, filed on Jan. 10, 2017.

(51) Int. Cl.
| | |
|---|---|
| *A61K 47/60* | (2017.01) |
| *A61K 47/54* | (2017.01) |
| *A61K 47/64* | (2017.01) |
| *A61P 35/00* | (2006.01) |
| *A61K 9/00* | (2006.01) |

(52) U.S. Cl.
CPC ............ *A61K 47/60* (2017.08); *A61K 9/0029* (2013.01); *A61K 47/54* (2017.08); *A61K 47/642* (2017.08); *A61P 35/00* (2018.01)

(58) Field of Classification Search
CPC ...... A61K 47/60; A61K 9/0029; A61K 47/54; A61K 47/642; A61P 35/00
See application file for complete search history.

(56) References Cited

U.S. PATENT DOCUMENTS

| | | |
|---|---|---|
| 4,810,646 A | 3/1989 | Jamas et al. |
| 4,992,540 A | 2/1991 | Jamas et al. |
| 5,028,703 A | 7/1991 | Jamas et al. |
| 5,389,640 A | 2/1995 | Gerster et al. |
| 5,607,677 A | 3/1997 | Jamas et al. |
| 5,741,495 A | 4/1998 | Jamas et al. |
| 5,939,090 A | 8/1999 | Beaurline et al. |
| 7,744,861 B2 | 6/2010 | Zhao et al. |
| 8,394,365 B2 | 3/2013 | Zhao et al. |

(Continued)

FOREIGN PATENT DOCUMENTS

| | | |
|---|---|---|
| WO | WO 03/043572 A2 | 5/2003 |
| WO | WO 2005/110013 A2 | 11/2005 |

(Continued)

OTHER PUBLICATIONS

English Translation of Israeli Office Communication corresponding to Israeli Patent Application No. 267,929 dated Feb. 22, 2022.
English Translation of Japanese Notice of Reasons for Rejection corresponding to Japanese Patent Application No. 2019-537064 dated Feb. 14, 2022.
English Translation of Mexican 1$^{st}$ Substantive Examination Requirement corresponding to Mexican Patent Application No. MX/a/2019/008276 dated Feb. 17, 2022.

(Continued)

*Primary Examiner* — Robert S Cabral
(74) *Attorney, Agent, or Firm* — Jacqueline F. Mahoney

(57) ABSTRACT

Provided are multi-arm polymer conjugates of Toll-Like Receptor ("TLR") agonists such as TLR 7/8 agonists, as well as related compositions, and methods of making and using such conjugates. Exemplary conjugates are encompassed by Formula I: (I) or a pharmaceutically acceptable salt form thereof, where R, taken together with each Q, is a residue of a polyol, polythiol, or polyamine bearing from 3 to about 50 hydroxyl, thiol, or amino groups; each Q is a linker selected from oxygen, sulfur and —NH; each POLY is independently a water-soluble, non-peptidic polymer; each Xr is independently a linkage-containing spacer moiety; q is a positive integer from 3 to about 50; and each TLR 7/8 AG is a Toll-like receptor 7/8 agonist. Also provided is a method of administering to a patient having cancer (a) an IL-2Rβ-activating amount of a long-acting, IL-2Rβ-selective agonist; and (b) a Toll-like receptor agonist such as a conjugate as described above, as well as related compositions, kits and methods.

$$R\text{-}(\text{-Q-POLY-Xr-TLR7/8 AG})_q \qquad (I)$$

8 Claims, 8 Drawing Sheets

(56) References Cited

U.S. PATENT DOCUMENTS

| | | | |
|---|---|---|---|
| 9,475,804 | B2 | 10/2016 | Wightman |
| 9,902,724 | B2 | 2/2018 | Wightman |
| 2005/0079155 | A1 | 4/2005 | Marshall |
| 2005/0281781 | A1 | 12/2005 | Ostroff |
| 2008/0044438 | A1 | 2/2008 | Ostroff et al. |
| 2010/0303850 | A1 | 12/2010 | Lipford et al. |
| 2015/0110742 | A1* | 4/2015 | Spiegel ............. A61K 31/4745 544/198 |

FOREIGN PATENT DOCUMENTS

| | | |
|---|---|---|
| WO | WO 2010/019233 A1 | 2/2010 |
| WO | WO 2011/063156 A2 | 5/2011 |
| WO | WO 2012/065086 A1 | 5/2012 |
| WO | WO 2013/096512 A1 | 6/2013 |
| WO | WO 2015/125159 A1 | 8/2015 |

OTHER PUBLICATIONS

English Translation of Mexican 2nd Substantive Examination Requirement corresponding to Mexican Patent Application No. MX/a/2019/008276 dated Jun. 2, 2022.

Hayashi et al., "Additive melanoma suppression with intralesional phospholipid-conjugated TLR7 agonists and systemic IL-2" Melanoma Research, vol. 21, No. 1, pp. 66-75, (Feb. 2011).

Australian Examination report No. 1 corresponding to Australian Patent Application No. 2018207283 dated Feb. 17, 2023.

English Translation of Notification of the First Office Action corresponding to Chinese Patent Application No. 201880006411.8 dated Oct. 9, 2022.

English Translation of Notice of Reasons for Rejection corresponding to Japanese Patent Application No. 2019-537064 dated Dec. 2, 2022.

English Translation of Office Action corresponding to Mexican Patent Application No. MX/a/2019/008276 dated Sep. 27, 2022.

Anz, et al., "Suppression of Intratumoral CCL22 by Type I Interferon Inhibits Migration of Regulatory T Cells and Blocks Cancer Progression", Cancer Research, vol. 75, No. 21, pp. 4483-4493, (2015).

Bacchi, et a., "Novel Synthetic Polyamines Are Effective in the Treatment of Experimental Microsporidiosis, an Opportunistic AIDS-Associated Infection", Antimicrobial Agents and Chemotherapy, vol. 46, No. 1, pp. 55-61, (Jan. 2002).

Basith, et al., "Toll-like receptor modulators: a patent review (2006-2010)", Expert Opin. Ther. Patents, vol. 21, No. 6, pp. 927-944, (2011).

Berge, et al., "Pharmaceutical Salts", Journal of Pharmaceutical Sciences, vol. 66, No. 1, pp. 1-19, (Jan. 1977).

Burns, et al., "The Imidazoquinolines, Imiquimod and R-848, Induce Functional, but Not Phenotypic, Maturation of Human Epidermal Langerhans' Cells", Clinical Immunology, vol. 94, No. 1, pp. 13-23, (2000).

Charych, et al., "Tipping the balance in the tumor microenvironment: An engineered cytokine (NKTR-214) with altered IL2 receptor binding selectivity and improved efficacy", Cancer Research, Abstract 482, Proceedings: AACR 104th Annual Meeting (2013).

Chi, et al., "Anti-tumor Activity of Toll-Like Receptor 7 Agonists", Frontiers in Pharmacology, vol. 8, Article 304, pp. 1-10, (May 2017).

Jego, et al., "Pathogen-associated molecular patterns are growth and survival factors for human myeloma cells through Toll-like receptors", Leukemia, vol. 20, pp. 1130-1137, (2006).

Kaczanowska, et al., "TLR agonists: our best frenemy in cancer immunotherapy", Journal of Leukocyte Biology, vol. 3, pp. 847-863, (2013).

Kiniwa, et al., "CD8[+] Foxp3[+] Regulatory T Cells Mediate Immunosuppression in Prostate Cancer", Clin. Cancer Res. vol. 13, No. 23, pp. 6947-6958, (Dec. 1, 2007).

Lu, et al., "TLR agonists for cancer immunotherapy: tipping the balance between the immune stimulatory and inhibitory effects", Frontiers in Immunology, vol. 5, Article 83, pp. 1-4, (Mar. 2014).

Zhao, et al., "Combination therapy targeting toll like receptors 7, 8 and 9 eliminates large established tumors", Journal for ImmunoTherapy of Cancer, vol. 2, No. 12, pp. 1-10, (2014).

PCT International Search Report and the Written Opinion corresponding to PCT Application No. PCT/US2018/013199 dated Apr. 24, 2018.

PCT International Preliminary Report on Patentability corresponding to PCT Application No. PCT/US2018/013199 dated Jul. 25, 2019.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003-1st, (Jan. 2003).

NOF Corporation, Peg Derivatives, Phospholipid and Drug Delivery Materials for Pharmaceuticals, 27 pages, Catalogue 2003-2nd, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

POLYPURE Products, PEG amines; PEG acids and amino acids; PEG thiols and disulfides; BIOTINS, 5 pages, (Apr. 2004).

POLYPURE Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producerand provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

European Communication corresponding to European Patent Application No. 18 705 743.5 dated Feb. 2, 2021.

English Translation of Indian Examination Report corresponding to Indian Patent Application No. 201917030041 dated Mar. 16, 2021.

* cited by examiner

MULTI-ARM POLYMER CONJUGATES OF TLR AGONIST COMPOUNDS AND RELATED IMMUNOTHERAPEUTIC TREATMENT METHODS

CROSS REFERENCE TO RELATED APPLICATIONS

This application is a 35 U.S.C. § 371 application of International Application No. PCT/US2018/013199, filed on Jan. 10, 2018, designating the United States, and claims the benefit of priority under 35 U.S.C. § 119(e) to U.S. Provisional Patent Application No. 62/444,735, filed on Jan. 10, 2017, to U.S. Provisional Patent Application No. 62/444,756, filed on Jan. 10, 2017, to U.S. Provisional Patent Application No. 62/467,945, filed on Mar. 7, 2017, to U.S. Provisional Patent Application No. 62/488,251, filed on Apr. 21, 2017, to U.S. Provisional Patent Application No. 62/488,407, filed on Apr. 21, 2017, to U.S. Provisional Patent Application No. 62/510,019, filed on May 23, 2017, and to U.S. Provisional Patent Application No. 62/510,024, filed on May 23, 2017, the disclosures of which are incorporated herein by reference in their entireties.

FIELD

The instant application relates to (among other things), multi-arm polymer conjugates of Toll-like receptor ("TLR") agonists, and in particular, Toll-like receptor agonists of TLR 7 and/or TLR 8, as well as to compositions comprising the multi-arm polymer TLR agonist conjugates, and methods of making and using the conjugates. The instant application also relates to the field of cancer immunotherapy and involves, for example, the treatment of an individual having cancer by administering to the individual a toll-like receptor (TLR) agonist, e.g., a multi-arm polymer conjugate of a toll-like receptor agonist, in combination with a long-acting IL-2Rβ-biased agonist, and related compositions and methods, to be described in greater detail herein.

BACKGROUND

Toll-like receptors ("TLRs") are expressed on several cell types belonging to the innate and adaptive immune system. At least 13 different TLRs have been identified to date in mammals (Zhao, G., et al., *Journal for ImmunoTherapy of Cancer* 2014, 2:12). TLR1, -2, -4, -5, -6, and -10 are expressed on the cell surface, while TLR 3, -7, -8, and -9 are situated on endosomal membranes within the cell (Kaczanowska, S., et al., *J. Leukoc Biol.* 2013 June; 93(6): 847-863). TLRs are sensors detecting pathogen and malignant cell-derived molecules called pathogen-associated molecular patterns (PAMPs) which, upon binding to TLRs, trigger the (NF)-κB and type I interferon pathways resulting in the production of pro-inflammatory cytokines in dendritic cells (DCs) and other antigen presenting cells such as macrophages. TLRs are crucial for stimulation of DC maturation, antigen uptake and presentation, and the differentiation of CD4$^+$ cells and control of regulatory T (Treg) cells.

TLR agonists have been investigated for their antitumor properties, however, in general, most TLR agonists have underperformed as cancer therapeutics. It has been postulated that such underperformance might be explained by a mechanism in which induction of immune suppressive factors dampens TLR agonist-induced inflammation. (Lu, H. *Frontiers in Immunology*, March 2014, 5, 83). For example, TLR agonists have immune stimulatory effects through the induction of co-stimulatory molecules such as CD80, CD86, and CD40 on dendritic cells and inflammatory cytokines such as TNF-α and IL-12 that polarize the immune response. However, TLR agonists also have immune inhibitory effects, e.g., by inducing several immune suppressive factors including IL-10, regulatory T cells (Tregs), and PD-1, all of which can suppress anti-tumor immunity (Lu, H., 2014, ibid).

TLRs-7, -8, and -9 are similar in their recognition of nucleic acid motifs and expression within endosomal compartments (Zhao, G., 2014, ibid). Several ligands, both synthetic and natural nucleosides, have been characterized as TLR7 and/or TLR8 ligands. Recognition of these nucleoside ligands by TLR7 or TLR8 receptors activates intracellular pathways that culminate in the induction of proinflammatory cytokines, chemokines, and type I interferons (IFNs), and in the upregulated on of co-stimulatory molecules. TLRs are type I membrane proteins, characterized by an ectodomain composed of leucine-rich repeats, responsible for recognition of pathogen-associated molecular patterns, and a cytoplasmic domain, called the Toll/interleukin-1 receptor (TIR) domain, which is required for downstream signaling. TLR7 and TLR8 are closely related, sharing their intracellular endosomal location, as well as their ligands. Recognition of a ligand by TLR7 or TLR8 is followed by recruitment of the TLR domain-containing adaptor molecule myeloid differentiation primary response gene 88 (MyD88). The association of TLR7/8 and MyD88 stimulates the recruitment of members of the interleukin-1 receptor-associated kinase family, resulting in the downstream activation of mitogen-activated protein kinases (MAPKs) and the IκB kinase (IKK) complex. Toll-like receptor agonists of TLR 7 and TLR 8 activate macrophages and can, in some instances, change the tumor environment from a tumor-promoting to a tumor-suppressive (inflammatory) environment.

In light of their potential ability to activate several cell types such as DCs, monocytes, macrophages, fibroblasts, and human keratinocytes, induce apoptosis, generate enhanced immunogenicity and sensitization to killing mediated by cytotoxic T-cell lymphocytes and chemotherapeutics, TLR ligands are considered to be a class of immune-response modifiers having the potential to generate an effective antitumor immune response. Furthermore, TLR8 ligands have been shown to reverse the suppressive function of CD8$^+$ Treg cells (Kiniwa Y., et al., *Clin Cancer Res* 2007; 13: 6947-58). Moreover, the application of TLR8 ligands resulted in a reduction of tumor infiltrating Foxp3$^+$ Treg cells changing the tumor environment from tumor promoting to tumor suppressive (Anz D. et al., *Cancer Res.* 2015; 75: 4483-93). On the other hand, TLR activation has, in certain instances, been shown to be advantageous for the proliferation, invasiveness, and/or survival of tumor cells (see, e.g., Bohnhorst J., et al., *Leukemia* 2006; 20:1138-1144; and Jego C., et al., *Leukemia* 2006; 20:1130-1137). Certain TLR 7/8 agonists have also been shown to induce immunosuppression and autoimmune disease (Chi H., et al. *Frontiers in Pharmacology.* 2017; 8: 304).

Although there have been substantial efforts in developing new and improved TLR agonists that overcome one or more of the above-noted drawbacks, there remains a need to identify and provide new and more effective TLR agonists and related treatment regimens that overcome the shortcomings of prior art compounds and existing treatment methodologies whilst also providing a favorable immune response without triggering significant undesirable side effects such as inflammation. The present disclosure seeks to address this and other needs. The TLR7/8 agonists described herein can be used as stand-alone immunotherapeutics (i.e., as a mono-immunotherapeutic), or, in another aspect, can be used in combination with a long acting IL-2Rβ-biased agonist.

SUMMARY

In a first aspect, the disclosure is directed to a multi-arm polymer conjugate of a Toll-like receptor ("TLR") agonist. More particularly, the conjugate comprises a TLR 7/8 agonist compound covalently attached, via a linkage-containing spacer moiety, to a multi-arm, water-soluble, non-peptidic polymer. Among other things, the conjugates provided herein allow local administration of the conjugate, e.g., to a tumor site, wherein the conjugate is effective to preferentially initiate anti-tumor immunity locally during residence at the tumor site. The architecture of the multi-armed conjugate, along with the particular TLR 7/8 agonist, attachment chemistry, and mode of administration are effective to result in a conjugate that remains for an extended period of time within a tumor, and is effective to increase tumor antigen presentation and T-cell stimulation (i.e., to result in enhanced CD8 T cell priming), that is, to elicit an innate immune response, while accompanied by minimal toxic side effects due to localized activity.

In some embodiments of the multi-arm conjugate, the TLR 7/8 agonist compound is a small molecule.

In yet one or more further embodiments of the multi-armed polymer conjugate, the multi-armed water-soluble polymer comprises from 3 to about 50 polymer arms, or from 3 to about 10 polymer arms, or from 3 to 6 polymer arms. In one or more particular embodiments, the multi-armed polymer conjugate comprises 3, 4, or 5 polymer arms. In one or more further embodiments, the multi-armed polymer conjugate comprises 4 polymer arms.

In some embodiments, the conjugate comprises a TLR 7/8 agonist covalently attached at the terminus of one or more of the arms of the multi-arm, water-soluble non-peptidic polymer. In one or more embodiments, the TLR 7/8 agonist is covalently attached at the terminus of each of the arms of the multi-arm, water-soluble non-peptidic polymer. In yet one or more embodiments, each of the polymer arms of the multi-armed polymer conjugate is the same.

In some particular embodiments, a multi-arm polymer conjugate has a structure in accordance with Formula I:

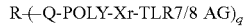  Formula I wherein R, taken together with each Q, is a residue of a polyol, polythiol, or polyamine bearing from 3 to about 50 hydroxyl, thiol, or amino groups; each Q is a linker selected from oxygen, sulfur and —NH (e.g., corresponding to an oxygen, sulfur or nitrogen atom from the polyol, polythiol, or polyamine, respectively); each POLY is independently a water-soluble, non-peptidic polymer; each $X_r$ is independently a linkage-containing spacer moiety; q is a positive integer from 3 to about 50; and each TLR 7/8 AG is a Toll-like receptor 7/8 agonist; or is a pharmaceutically acceptable salt form thereof.

In yet one or more further embodiments, the TLR 7/8 agonist is (N-[4-(4-amino-2-ethyl-1H-imidazo[4,5c]quinolin-1-yl)butyl] methane sulfonamide or [8-(3-(pyrrolidin-1-ylmethyl)benzyl)-4-amino-2-butoxy-7,8-dihydropteridin-6 (5H)-one].

In some other embodiments, the TLR 7/8 agonist is an imidazoquinoline compound. In one or more preferred embodiments, the TLR 7/8 agonist is resiquimod or imiquimod, or an analog, derivative, or isomer thereof.

In yet some further embodiments in reference to Formula I, R, taken together with Q, is a residue of a polyol.

In some embodiments pertaining to Formula I, each $X_r$ is independently a stable linkage-containing spacer moiety. In yet some alternative embodiments, each $X_r$ is independently a releasable linkage-containing spacer moiety.

In some additional embodiments related to Formula I, q is a positive integer selected from 3 to 10, or is a positive integer selected from 3 to 6, or is a positive integer selected from 3, 4, and 5, or is 4.

In yet some further embodiments, the linkage-containing spacer moiety comprises a thioether, carbamate, ester, carbonate, or urea functional group.

In yet some additional embodiments, the linkage-containing spacer moiety comprises an enzyme-cleavable peptidic linkage.

In one or more particular embodiments pertaining to Formula I, Xr is in accordance with Formula II:

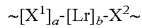  Formula II where a is zero or one (meaning that when a is zero, $X^1$ is absent, and when a is one, $X^1$ is present); b is zero or one (meaning that when b is zero, Lr is absent, and when b is one, Lr is present); $X^1$, when present, is a spacer; Lr, when present, is a linkage; and $X^2$ is a functional group directly covalently attached to the TLR 7/8 agonist.

In some embodiments related to Formula II, "a" is zero. In yet some other embodiments, "b" is zero. In some additional embodiments, both "a" and "b" are zero. In yet some further embodiments, "a" is one. In yet some further embodiments, "b" is one. In yet some additional embodiments, both "a" and "b" are one.

In some further embodiments related to Formula II, $X^1$ is —CH$_2$C(O)—.

In yet some additional embodiments related to Formula II, $X^2$ is selected from the group consisting of —C(O)—NH—, —NH—C(O)—NH—, —NH—C(O)—, and —NH.

In yet some additional embodiments related to Formula II, Lr is selected from the group consisting of —(CR$_x$R$_y$)$_z$—, and —NH(CR$_x$R$_y$)$_z$—, where each R$_x$ and R$_y$ is independently selected from hydrogen, lower alkyl, halo, and halo-substituted lower alkyl, and z is an integer from 1 to 6. For example, in some additional particular embodiments of the foregoing, Lr is selected from —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CHF—, —CHCH$_3$—, —CHCH(CH$_3$)$_2$—, —CHCH$_2$CH(CH$_3$)$_2$—, —C(CH$_3$)$_2$—, —NHCH$_2$—, —NHCH$_2$CH$_2$—, —NHCH$_2$CH$_2$CH$_2$—, —NHCH$_2$CH$_2$CH$_2$CH$_2$—, —NHCH$_2$CH$_2$CH$_2$CH$_2$CH$_2$—, —NHCH$_2$CH$_2$CH$_2$CH$_2$CH$_2$CH$_2$—, —NHCH$_2$CHF—, —NHCHCH$_3$—, —NHCHCH(CH$_3$)$_2$—, —NHCHCH$_2$CH(CH$_3$)$_2$—, and —NHC(CH$_3$)$_2$—.

In one or more embodiments of the multi-arm polymer portion of the conjugate, the water-soluble, non-peptidic polymer is a poly(alkylene oxide). In some particular embodiments, the poly(alkylene oxide) is a poly(ethylene oxide).

In some embodiments, the water-soluble, non-peptidic polymer comprised within each of "q" polymer arms contains from about 1 to about 30 monomeric subunits. In yet some other embodiments, the overall water-soluble, non-peptidic polymer, i.e., including each of its polymer arms, has a molecular weight of from about 2,000 Daltons to about 150,000 Daltons. In some certain other embodiments, the overall water-soluble, non-peptidic polymer has a molecular weight of from about 5,000 Daltons to about 40,000 Daltons. In yet additional embodiments, the overall water-soluble, non-peptidic polymer has a molecular weight of from about 5,000 Daltons to about 25,000 Daltons.

In one or more particular embodiments, the multi-arm polymer conjugate of a TLR 7/8 agonist has a formula in accordance with Formula III:

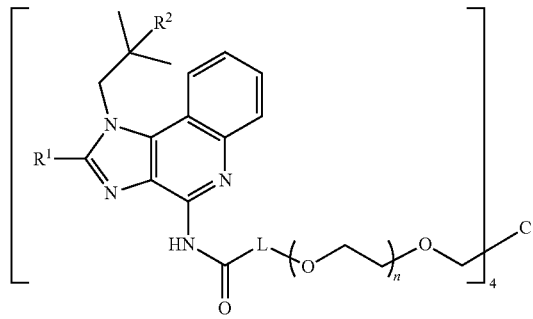

(Formula III)

or a pharmaceutically acceptable salt or stereoisomer thereof, wherein L is —(CH$_2$)$_m$—, —(CH$_2$)$_m$—NH—C(O)—(CH$_2$)$_m$—, —CHF—(CH$_2$)$_m$—NH—C(O)—(CH$_2$)$_m$—, —CH(CH$_3$)—NH—C(O)—(CH$_2$)$_m$—, —(CH$_2$)$_m$—CH(CH(CH$_3$)$_2$)—NH—C(O)—(CH$_2$)$_m$—, —(CH$_2$)$_m$—CH(CH$_2$CH(CH$_3$)$_2$)—NH—C(O)—(CH$_2$)$_m$—, —C(CH$_3$)$_2$—NH—C(O)—(CH$_2$)$_m$—, a single bond, or —NH—(CH$_2$)$_m$—, each m is independently an integer from 1 to 5, inclusive; each n is independently an integer from 40 to 350, inclusive; R$^1$ is hydrogen or —CH$_2$—O—CH$_2$—CH$_3$; and R$^2$ is hydrogen or hydroxyl. In yet some further embodiments related to Formula III, L is selected from —CH$_2$—, —CH$_2$—CH$_2$—NH—C(O)—CH$_2$—, —CH$_2$—CH$_2$—CH$_2$—, —CHF—CH$_2$—NH—C(O)—CH$_2$—, —CH$_2$—NH—C(O)—CH$_2$—, —CH(CH$_3$)—NH—C(O)—CH$_2$—, —CH$_2$—CH(CH(CH$_3$)$_2$)—NH—C(O)—CH$_2$—, —CH$_2$—CH(CH$_2$CH(CH$_3$)$_2$)—NH—C(O)—CH$_2$—, —C(CH$_3$)$_2$—NH—C(O)—CH$_2$—, a single bond, and —NH—CH$_2$—CH$_2$—.

In yet some further embodiments of Formula III, each n is independently an integer from 100 to 250, inclusive. In yet some other embodiments, R$^1$ is hydrogen and R$^2$ is hydrogen. In yet some additional embodiments, R$^1$ is —CH$_2$—O—CH$_2$—CH$_3$ and R$^2$ is hydroxyl.

In one or more particular embodiments, the multi-armed polymer conjugate is selected from Compounds 1-10 and 12-16 as follows:

Compound 1

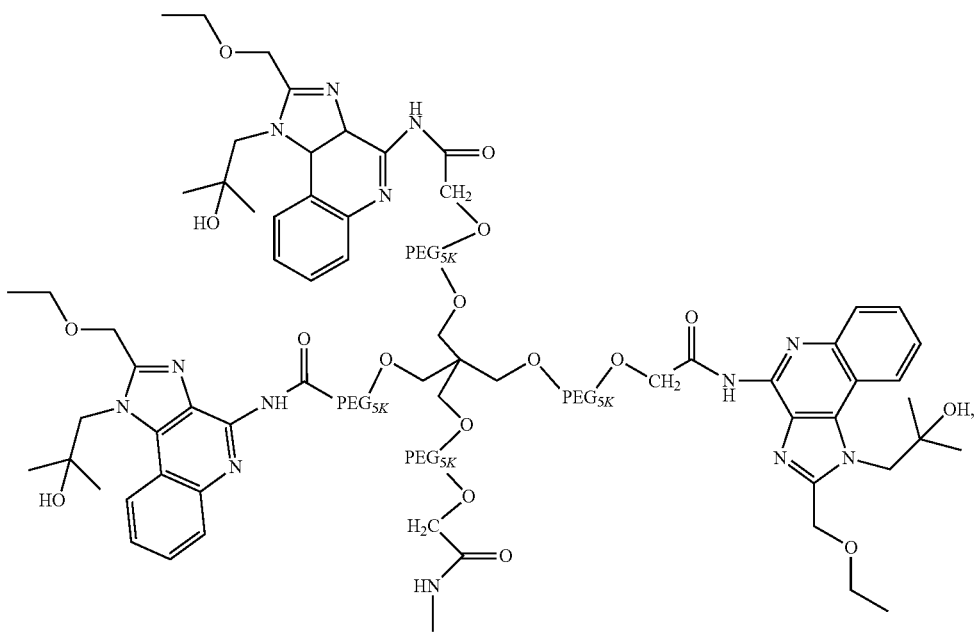

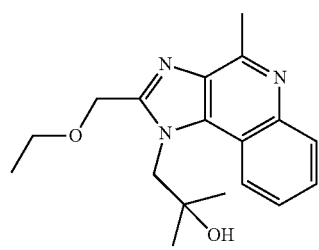

wherein each PEG5k is linear polyethylene glycol having a formula ~$(CH_2CH_2O)_y CH_2CH_2$~, where y is about 113;
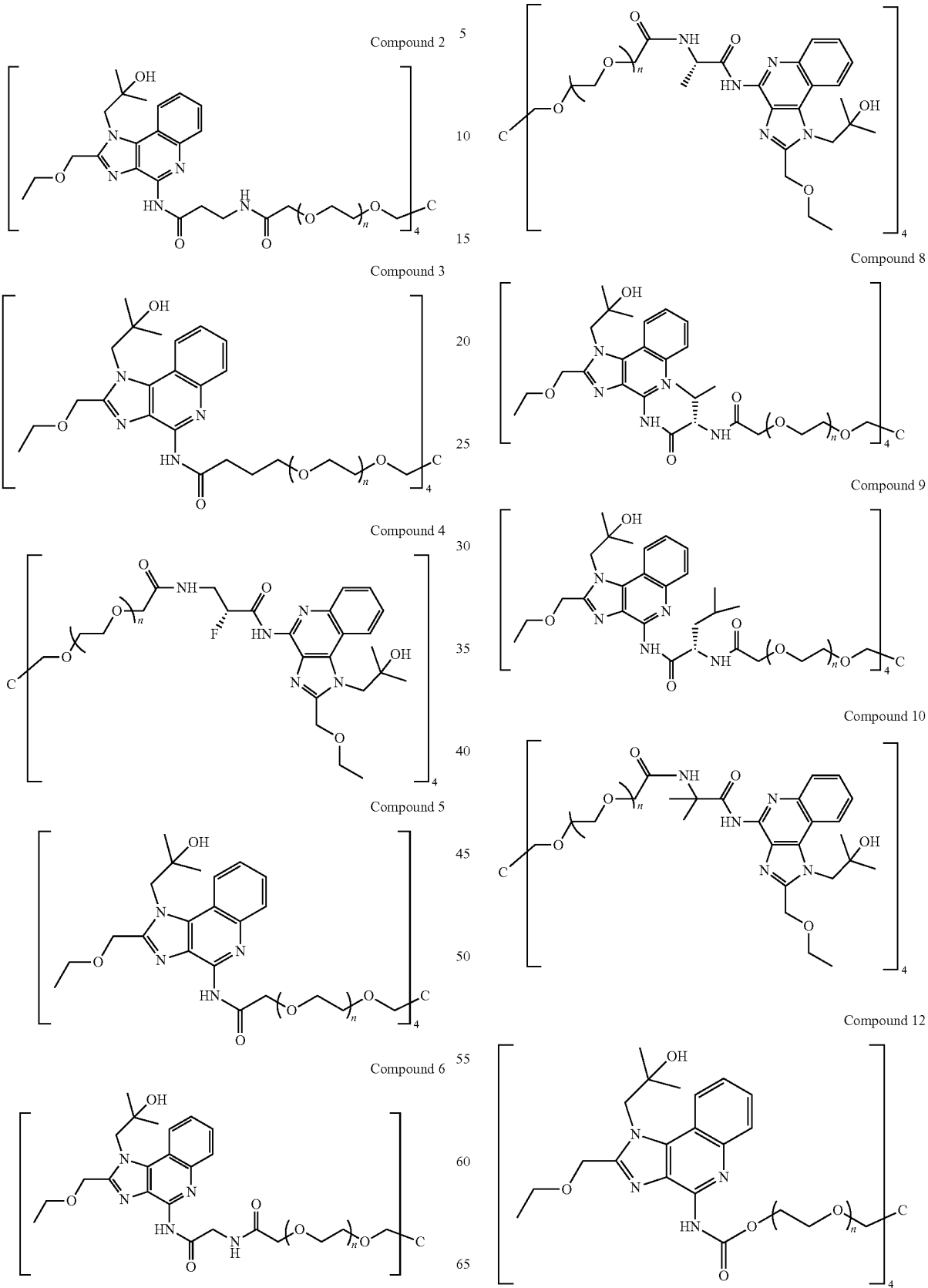

-continued

Compound 13

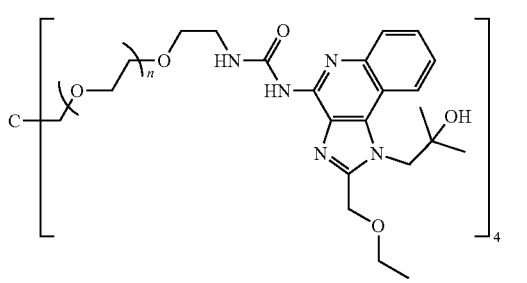

Compound 14

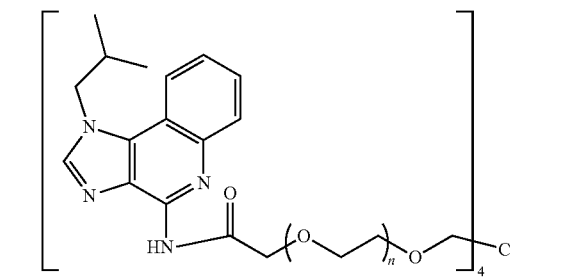

Compound 15

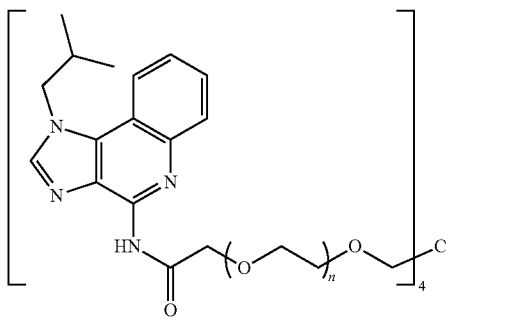

Compound 16

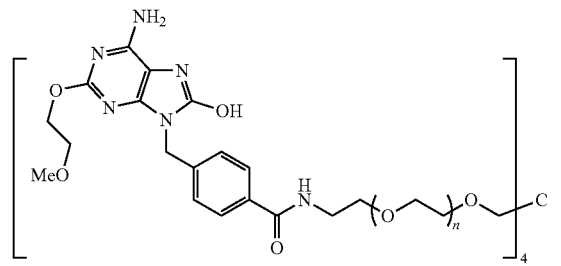

or a pharmaceutically acceptable salt or stereoisomer thereof, wherein each n is independently an integer from 40 to 350.

In one or more particular embodiments, the multi-armed polymer conjugate is Compound 6.

In yet one or more additional embodiments, provided is a composition comprising a multi-arm polymer conjugate as described herein and a pharmaceutically acceptable excipient.

In yet another aspect (e.g., a second aspect), the disclosure provides a method of treatment comprising administering a multi-arm polymer conjugate as provided herein to a subject in need thereof.

In yet another, i.e., third, aspect, disclosed is a multi-armed polymer conjugate of a TLR 7/8 agonist as provided herein for use in the treatment of cancer.

In a related, i.e., fourth, aspect, disclosed is a multi-armed polymer conjugate of a TLR 7/8 agonist as provided herein for use in the preparation of a medicament useful in the treatment of cancer.

In yet another, i.e., fifth, aspect, disclosed is a method of preparing a multi-armed polymer conjugate of a TLR 7/8 agonist by covalently attaching either via a stable or releasable linkage-containing spacer moiety, a TLR 7/8 agonist to a multi-armed water-soluble polymer under conditions suitable to effect said covalent attaching.

In yet a further, i.e., sixth, aspect, provided herein is a method comprising administering to a subject having cancer, a TLR agonist such as, for example, a multi-armed polymer conjugate of a TLR 7/8 agonist as disclosed herein and an IL-2Rβ-activating amount of a long acting IL-2Rβ-biased agonist, both to be described in greater detail herein. In certain embodiments, the combination is effective to promote activation of the immune system (for example through promotion of CD8 T cells, CD11c+ and CD8+ dendritic cells, and neutrophils), while also overcoming immune suppression (for example though suppression of T regulatory cells, macrophages, and monocytes).

By way of clarity, with regard to the sequence of administering, the TLR 7/8 agonist and the long acting IL-2Rβ-biased agonist may be administered concurrently or sequentially and in any order, and via the same and/or different routes of administration, each in an immunomodulating amount. Moreover, treatment may comprise a single cycle of therapy, or may comprise multiple (i.e., two or more) cycles of therapy.

In one or more embodiments, the TLR agonist is administered locally and the long acting IL-2Rβ-biased agonist is administered parenterally. In one or more related embodiments, the TLR agonist, e.g., a multi-armed polymer conjugate of a TLR 7/8 agonist, is administered directly to the site of a tumor.

In one or more embodiments related to the sixth aspect, the TLR agonist, e.g., a multi-armed polymer conjugate of a TLR 7/8 agonist, is administered to the subject separately from the long acting IL-2Rβ-biased agonist.

In yet one or more further embodiments, the TLR agonist, e.g., a multi-armed polymer conjugate of a TLR 7/8 agonist, is administered to the subject prior to administering the long acting IL-2Rβ-biased agonist. For example, in one or more embodiments, the TLR agonist and the long acting IL-2Rβ-biased agonist are both administered on day 1 of treatment. In one or more alternative embodiments, the TLR agonist is administered on day 1 of treatment and the long acting IL-2Rβ-biased agonist is administered on any one of days 1 to 4 of treatment. For example, the long acting IL-2Rβ-biased agonist is administered on any one of days 1, 2, 3, or 4 of treatment.

In a preferred embodiment, the subject is a human subject.

In one or more additional embodiments, the cancer is a solid cancer. For example, the cancer is selected from the group consisting of breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Hodgkin's disease and adrenocortical cancer.

In some embodiments, the long-acting IL-2Rβ-biased agonist comprises aldesleukin releasably covalently attached to polyethylene glycol. In yet some additional embodiments, the long acting IL-2Rβ-biased agonist comprises aldesleukin releasably covalently attached to from 4, 5 and 6 polyethylene glycol polymers. In yet some further embodiments, the long acting IL-2Rβ-biased agonist comprises aldesleukin releasably covalently attached to an average of about 6 polyethylene glycol polymers. In one or more additional embodiments, the polyethylene glycol polymers that are releasably covalently attached to aldesleukin are branched.

In yet some further embodiments related to any one or more of the foregoing aspects or embodiments, the TLR agonist is a TLR 7 or a TLR 8 agonist. In one or more embodiments, the TLR agonist is a TLR 7 agonist. In yet one or more alternative embodiments, the TLR agonist is a TLR 8 agonist. In some embodiments, the TLR agonist is a long-acting TLR agonist such as a long acting TLR 7 or a long-acting TLR 8 agonist (e.g., a multi-armed polymer modified TLR 7 or TLR 8 agonist.

In yet some additional embodiments, the long-acting TLR agonist is a multi-armed water-soluble polymer conjugate of a TLR agonist such as a TLR 7/8 agonist. In yet one or more further embodiments, the multi-armed water-soluble polymer is stably covalently linked to the TLR agonist, e.g., the TLR 7/8 agonist. In one or more alternative embodiments, the multi-armed water-soluble polymer is releasably covalently linked to the TLR agonist, e.g., the TLR 7/8 agonist.

In yet one or more particular embodiments, the long-acting TLR agonist is a 4-arm-pentaerythritolyl-based polyethylene glycol conjugate having a TLR agonist molecule covalently linked, either stably or releasably, at the terminus of each of its four polymer arms.

In some preferred embodiments, the long acting IL-2Rβ-biased agonist comprises compounds encompassed by the following formula:

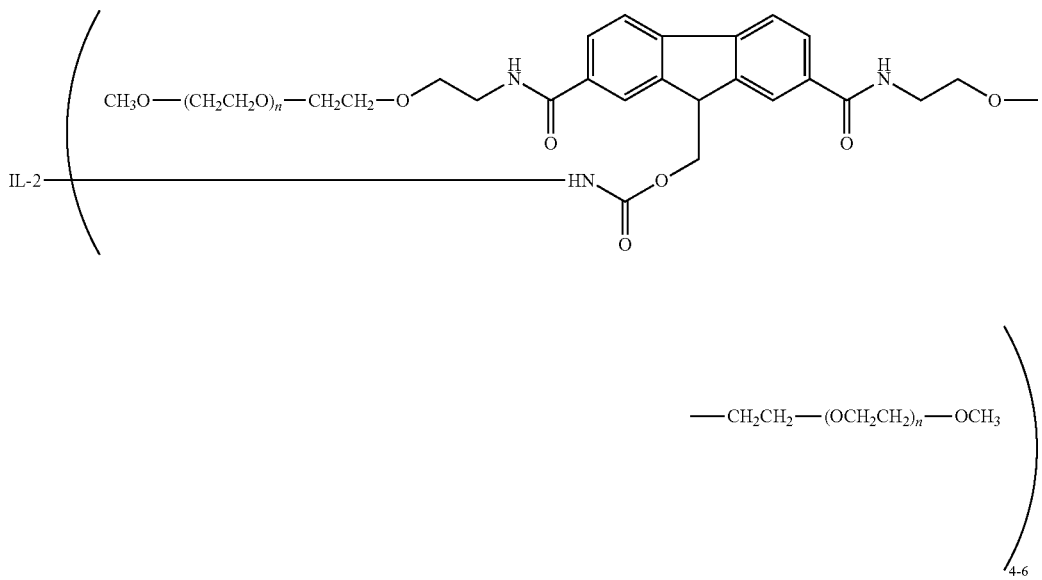

wherein IL-2 is an interleukin-2, "n" is an integer from about 3 to about 4000, or pharmaceutically acceptable salts thereof.

In some embodiments, the long acting IL-2Rβ-biased agonist having a formula as set forth in the preceding paragraph is comprised in a composition comprising no more than 10% (based on a molar amount) of compounds encompassed by the following formula:

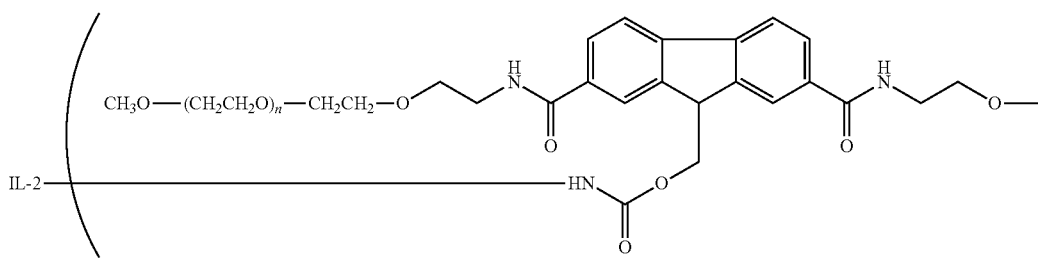

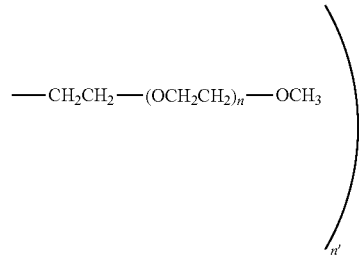

wherein IL-2 is interleukin-2, n' is an integer selected from the group consisting of 1, 2, 3, 7 and >7, and pharmaceutically acceptable salts thereof.

In some further embodiments of the method of administering, the TLR 7/8 conjugate has the following structure:

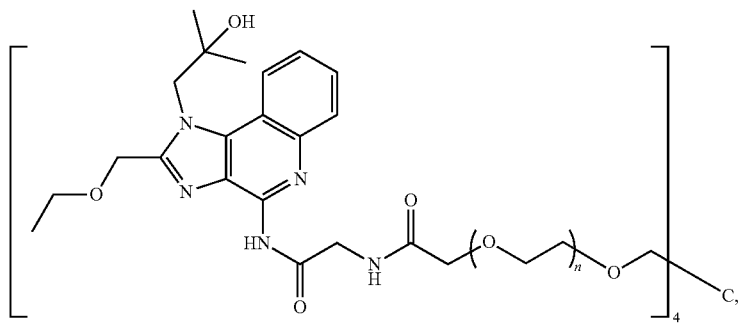

wherein each n is independently an integer from 40 to 350. In one or more related embodiments, the value of n in each of the polymer arms is substantially the same. In some particular embodiments, the value of n in each of the four polymer arms is about 113.

In some embodiments of the sixth aspect, the administering is effective to produce an abscopal effect in the subject.

In some further embodiments related to the foregoing, the administering is effective to provide a percent survival rate, when evaluated in a suitable animal model, such as a mouse CT-26 colon tumor model, at a day after start of treatment that is after the day by which all subjects in the vehicle only group have reached 0% survival, e.g., between days 35 and 50, that is greater than that observed for administration of each of the single agents alone, i.e., the long-acting IL-2Rβ-biased agonist and the TLR agonist.

In yet another aspect, provided is a kit comprising an IL-2Rβ-activating amount of a long acting IL-2Rβ-biased agonist and an innate immunity activating amount of a TLR agonist, e.g., the multi-armed polymer conjugate of a TLR 7/8 agonist, accompanied by instructions for use in treating a subject having cancer.

In one or more embodiments of the kit, the long acting IL-2Rβ-biased agonist and the TLR agonist are comprised in a single composition for administration to the subject, where the single composition optionally comprises a pharmaceutically acceptable excipient.

In some alternative embodiments of the kit, the long acting IL-2Rβ-biased agonist and the TLR agonist are provided in separate containers, and the kit comprises instructions for administering the TLR agonist and the long-acting IL-2Rβ-biased agonist separately to the subject.

In some embodiments of the kit, both the long-acting IL-2Rβ-biased agonist and the TLR agonist are in solid form. In one or more related embodiments, each of the long acting IL-2Rβ-biased agonist and the long acting TLR agonist are in a solid form suitable for reconstitution in an aqueous diluent.

In yet one or more further embodiments, each of the long acting IL-2Rβ-biased agonist and the TLR agonist is comprised within separate compositions each comprising a pharmaceutically acceptable excipient.

Additional embodiments of the present conjugates, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment.

DETAILED DESCRIPTION

Definitions

Figure 1:
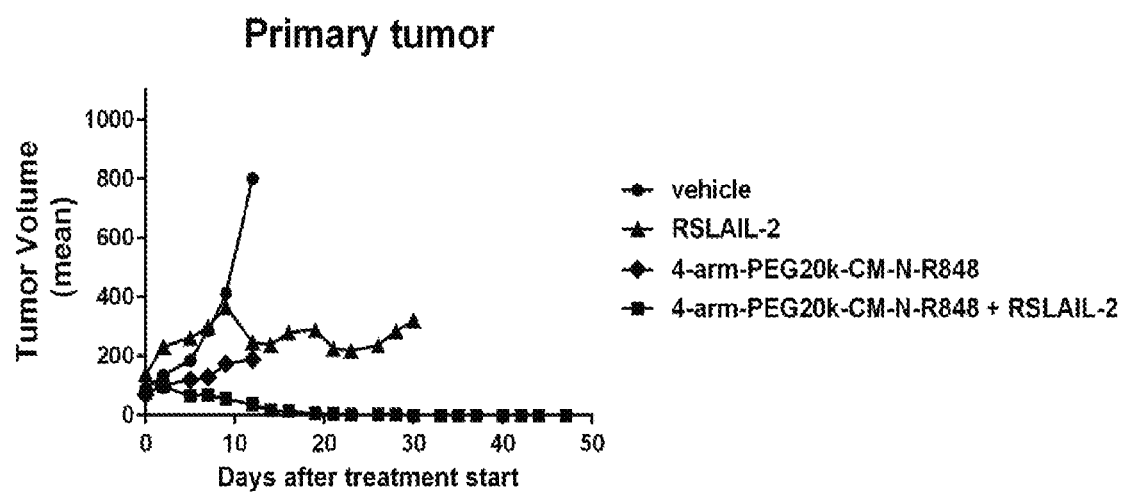
FIG. 1 is a plot showing primary tumor (TLR agonist injection site) volume versus days following initial dosing of mice treated with various interventions (vehicle, exemplary long acting IL-2Rβ-biased agonist, RSLAIL-2; an exemplary TLR agonist, 4-arm-PEG20k-CM-N—R848; and a combination of RSLAIL-2 and 4-arm-PEG20k-CM-N—R848) in a mouse colon carcinoma model (CT-26) as described in detail in Example 21.

As used in this specification, the singular forms "a," "an," and "the" include plural referents unless the context clearly dictates otherwise.

"Water soluble, non-peptidic polymer" indicates a polymer that is at least 35% (by weight) soluble, preferably greater than 70% (by weight), and more preferably greater than 95% (by weight) soluble, in water at room temperature. Typically, an unfiltered aqueous preparation of a "water-soluble" polymer transmits at least 75%, more preferably at least 95%, of the amount of light transmitted by the same solution after filtering. It is most preferred, however, that the water-soluble polymer is at least 95% (by weight) soluble in water or completely soluble in water. With respect to being "non-peptidic," a polymer is non-peptidic when it has less than 35% (by weight) of amino acid residues.

The terms "monomer," "monomeric subunit" and "monomeric unit" are used interchangeably herein and refer to one of the basic structural units of a polymer. In the case of a homo-polymer, a single repeating structural unit forms the polymer. In the case of a co-polymer, two or more structural units are repeated—either in a pattern or randomly—to form the polymer. Preferred polymers are homo-polymers. The water-soluble, non-peptidic polymer comprises one or more monomers serially attached to form a chain of monomers. The polymer can be formed from a single monomer type (i.e., is homo-polymeric) or two or three monomer types (i.e., is co-polymeric).

A "polymer" as used herein is a molecule possessing from about 2 to about 2000 or more, e.g. from about 2 to about 4000, monomers. Specific polymers include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG polymer" or any polyethylene glycol is one in which substantially all (preferably all) monomeric subunits are ethylene oxide subunits, though, the polymer may contain distinct end capping moieties or functional groups, e.g., for conjugation. PEG polymers can comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG polymers, the variable (n) (i.e., number of repeat units) ranges from about 2 to 2000, or from about 2 to 4000, and the terminal groups and architecture of the overall PEG can vary. When PEG further comprises a functional group for linking to, e.g., a small molecule drug, the functional group when covalently attached to a PEG polymer does not result in formation of an oxygen-oxygen bond (—O—O—, a peroxide linkage).

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy or an alkaaryloxy group. Thus, examples of end-capping moieties include alkoxy (e.g., methoxy and, ethoxy), benzyloxy, as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) of interest to which the polymer is coupled, can be determined by using a suitable detector. Such labels include, without limitation, fluorescers, chemiluminescers, moieties used in enzyme labeling, colorimetric moieties (e.g., dyes), metal ions, radioactive moieties, and the like. Suitable detectors include photometers, films, spectrometers, and the like. In addition, the end-capping group may contain a targeting moiety.

The term "targeting moiety" refers to a molecular structure that helps the conjugates to localize to a targeting area, e.g., help enter a cell, or bind a receptor. Preferably, the targeting moiety comprises a vitamin, antibody, antigen, receptor, DNA, RNA, sialyl Lewis X antigen, hyaluronic acid, sugars, cell-specific lectins, steroid or steroid derivative, RGD peptide, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phosphatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When a polymer conjugate has a targeting group comprising a detectable label, the amount and/or distribution/location of the polymer and/or the moiety (e.g., active agent) to which the polymer is conjugated can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation, or viscometry to determine weight average molecular weight. PEG polymers are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

"Branched," in reference to the geometry or overall structure of a polymer, refers to a polymer having two or more polymers "arms" extending from a branch point.

"Forked," in reference to the geometry or overall structure of a polymer, refers to a polymer having two or more functional groups (typically through one or more atoms) extending from a branch point.

A "branch point" refers to a bifurcation point comprising one or more atoms at which a polymer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group may vary depending upon the type of chemically reactive group that is being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "releasable linkage" is a relatively labile bond that cleaves under physiological conditions, wherein the cleavage may occur by way o any of a number of different mechanisms. One type of exemplary releasable linkage is a hydrolysable bond, that is, one that cleaves upon reaction with water (i.e., is hydrolyzed), e.g., under physiological conditions, such as for example, hydrolysis of an amide bond such as an aromatic amide bond. The tendency of a bond to hydrolyze in water may depend not only on the general type of linkage connecting two atoms but also on the substituents attached to these atoms. Appropriate hydrolytically unstable or weak linkages may include but are not limited to carboxylate ester, phosphate ester, anhydrides, acetals, ketals, acyloxyalkyl ether, imines, orthoesters, peptides, oligonucleotides, thioesters, and carbonates. Releasable linkages also include enzymatically releasable linkages, where an "enzymatically releasable linkage" means a linkage that is subject to cleavage by one or more enzymes. Additional types of release mechanisms include but are not limited to 1,6-benzyl elimination, β-elimination, and the like. While certain bonds may be considered to be stable or releasable, such characterization should be considered within the overall structure of a molecule or structural entity. In certain instances, a polymer conjugate containing a releasable bond is referred to as a prodrug, wherein upon cleavage of the releasable bond in vivo (i.e., under physiological conditions), the parent drug is released (or is eventually released, depending upon the number of polymeric moieties releasably attached to an active agent). A covalent "releasable" linkage, for example, in the context of a water soluble polymer such as polyethylene glycol that is covalently attached to an active moiety such as interleukin-2 or a TLR agonist such as resiquimod (also known as R848), is one that cleaves under physiological conditions to thereby release or detach a water soluble polymer from the active moiety, or to detach an active moiety from a water-soluble polymer.

A "stable" linkage or bond refers to a chemical bond that is substantially stable in water (e.g., under physiological conditions), that is to say, does not undergo hydrolysis under physiological conditions to any appreciable extent over an extended period of time. Examples of hydrolytically stable linkages generally include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under physiological conditions. Hydrolysis rates of representative chemical bonds can be found in most standard chemistry textbooks.

A "TLR 7/8 agonist" (or "TLR agonist") is any compound which is an agonist to Toll-like receptor 7 and/or Toll-like receptor 8.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Alkyl" refers to a hydrocarbon chain, ranging from about 1 to 20 atoms in length. Such hydrocarbon chains are preferably but not necessarily saturated and may be branched or straight chain. Exemplary alkyl groups include methyl, ethyl, propyl, butyl, pentyl, 2-methylbutyl, isopropyl, 3-methylpentyl, and the like. As used herein, "alkyl" includes cycloalkyl when three or more carbon atoms are referenced. An "alkenyl" group is an alkyl group of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo atoms (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclyl, amino, phenoxy, nitro, carboxy, acyl, cyano, or the like. The substituted alkyl groups may be substituted once, twice or three times with the same or with different substituents.

"Lower alkyl" refers to an alkyl group containing from 1 to 7 carbon atoms, and may be straight chain or branched, as exemplified by methyl, ethyl, n-butyl, i-butyl, t-butyl.

"Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Pharmaceutically acceptable excipient" or "pharmaceutically acceptable carrier" refers to a component that may be included in the compositions described herein and causes no significant adverse toxicological effects to a patient.

The term "aryl" means an aromatic group having up to 14 carbon atoms. Aryl groups include phenyl, naphthyl, biphenyl, phenanthrenyl, naphthalenyl, and the like. "Substituted phenyl" and "substituted aryl" denote a phenyl group and aryl group, respectively, substituted with one, two, three, four or five (e.g., 1-2, 1-3 or 1-4 substituents) chosen from halo (F, Cl, Br, I), hydroxy, cyano, nitro, alkyl (e.g., $C_{1-6}$ alkyl), alkoxy (e.g., $C_{1-6}$ alkoxy), benzyloxy, carboxy, aryl, and so forth.

An exemplary conjugate, active moiety, or other suitably applicable chemical moiety as described herein is meant to encompass, where applicable, analogues, isomers, polymorphs, solvates, and pharmaceutically acceptable salt forms thereof.

"Pharmacologically effective amount," "physiologically effective amount," and "therapeutically effective amount" are used interchangeably herein to mean the amount of an active agent, typically a polymer conjugate, that is needed to provide a desired level of active agent and/or conjugate in the bloodstream or in the target tissue. The precise amount may depend upon numerous factors, e.g., the particular active agent, the components and physical characteristics of the composition, intended patient population, patient considerations, and may readily be determined by one skilled in the art, based upon the information provided herein and available in the relevant literature.

A basic reactant or an acidic reactant described herein includes neutral, charged, and any corresponding salt forms thereof.

The term "patient," or "subject" as used herein refers to a living organism suffering from or prone to a condition that can be prevented or treated by administration of a compound or composition or combination as provided herein, such as a cancer, and includes both humans and animals. Subjects include, but are not limited to, mammals (e.g., murines, simians, equines, bovines, porcines, canines, felines, and the like), and preferably are human.

"Optional" or "optionally" means that the subsequently described circumstance may but need not necessarily occur, so that the description includes instances where the circumstance occurs and instances where it does not.

A "small molecule" as used herein refers to an organic compound typically having a molecular weight of less than about 1000.

Overview

The multi-arm water-soluble polymer-TLR 7/8 agonist conjugates described herein incorporate a number of innovative advances in drug design and treatment rationale that integrate into a novel, potentially safer and highly efficacious anti-cancer therapy. They are capable of innate immune system activation, and, when comprised of releasable linkages to the TLR agonist compound, are effective to release and retain an active TLR 7/8 agonist in an injected tissue such as a cancerous tumor. The conjugates, when administered intratumorally, are effective to activate local tumor antigen presentation to cytotoxic T cells and overcome immune suppressive signals in the tumor environment. The multi-arm water-soluble polymer scaffold contributes to an injected conjugate being primarily retained at the injected tumor site, whereby TLR 7/8 agonist dependent immune activation is highest in the treatment site with reduced systemic activity. A key advantage of such drug design over prior systemic small molecule TLR agonists is localized drug activity at the treated tumor and decreased systemic exposure reducing potential toxicities.

Additionally, a combination treatment as provided herein, in which a multi-arm water-soluble polymer-TLR 7/8 agonist conjugate is administered in combination with a long acting IL-2Rβ-biased agonist, stems from an inherent synergy of the local TLR 7/8 agonist polymer conjugate-driven anti-tumor innate immune activation and a systemic intratumoral expansion of cytotoxic T cells by the long acting IL-2Rβ-biased agonist. As described herein, studies in multiple syngeneic tumor models show that optimization of pharmacokinetic and pharmacodynamic properties of the dual therapeutic combination results in a highly efficacious combination therapy that successfully couples anti-tumor innate and adaptive immune activation analogously to a natural pathogen driven immune response. Both treatment components activate complementary arms of the immune system to engage the entire immune activation cascade required for systemic tumor clearance. The combination therapy described herein is designed to synergistically elicit a safer and more effective anti-tumor immune response than either agent administered singly. These and other features will become apparent and are described in detail in the sections which follow.

Multi-Arm Polymer Conjugates of a TLR 7/8 Agonist

As described above, provided herein are multi-arm polymer conjugates of a Toll-like receptor ("TLR") agonist compound, i.e., a TLR 7/8 agonist. In some particular embodiments, the multi-arm polymer conjugate has a structure in accordance with Formula I:

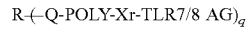

Formula I wherein R, taken together with each Q, is a residue of a polyol, polythiol, or polyamine bearing from 3 to about 50 hydroxyl, thiol, or amino groups, respectively; each Q is a independently a linker selected from oxygen, sulfur and —NH (e.g., corresponding to an oxygen, sulfur or nitrogen atom from the polyol, polythiol, or polyamine, respectively); each POLY is independently a water-soluble, non-peptidic polymer; each Xr is independently a linkage-containing spacer moiety; q is a positive integer from 3 to about 50; and each TLR 7/8 AG is a Toll-like receptor 7/8 agonist, wherein the Formula I also encompasses pharmaceutically acceptable salts thereof. We will now consider each of the various components of the multi-arm polymer conjugate of Formula I.

Considering Formula I, in one or more embodiments, the residue of the polyol, polythiol or polyamine, "R," used in connection with the multi-arm polymer is an organic radical-containing moiety possessing from about 3 to about 150 carbon atoms (e.g., from about 3 to about 50 carbon atoms). In some preferred embodiments, R when taken together with Q, that is, $(R-Q)_q$, that is the polyol, polyamine or polythiol core molecule, comprises from 3 to about 25 carbon atoms, or from 3 to about 10 carbon atoms, e.g., such as 3, 4, 5, 6, 7, 8, 9, or 10 carbon atoms. The residue may contain one more heteroatoms (e.g., O, S, or N) in addition to those defined by Q. By residue, in reference to a polyol (or polyamine or polythiol), is meant the parent molecule following removal of one or more of its terminal hydrogen atoms, to provide an organic radical suitable for attachment to POLY.

As previously indicated, the residue of the polyol, polythiol or polyamine, "R-Q"$_q$ that forms the basis of the branching for the multi-armed conjugates provided herein, originates from a corresponding polyol, polythiol or polyamine. In one or more embodiments, the corresponding polyol, polythiol, or a polyamine bears at least three hydroxyl, thiol, or amino groups, respectively, available for polymer attachment. A "polyol" is a molecule comprising three or more hydroxyl groups. A "polythiol" is a molecule that comprises three or more thiol groups. A "polyamine" is a molecule comprising three or more amino groups.

In one or more embodiments, the polyol, polyamine or polythiol typically contains 3 to about 25 hydroxyl groups, or amino groups, or thiol groups, respectively, such as from 3 to about 10 (i.e., 3, 4, 5, 6, 7, 8, 9, or 10) hydroxyl, amino groups or thiol groups, respectively, preferably from 3 to about 8 (i.e., 3, 4, 5, 6, 7, or 8) hydroxyl, amino groups or thiol groups, respectively. In one or more embodiments, the number of atoms between each hydroxyl, thiol, or amino group will vary, although lengths of from about 1 to about 20 (e.g., from 1 to about 5) intervening atoms, such as carbon atoms, between each hydroxyl, thiol or amino group, are exemplary. In referring to intervening core atoms and lengths, —CH$_2$— is considered as having a length of one intervening atom, —CH$_2$CH$_2$— is considered as having a length of two atoms, and so forth.

Exemplary polyols and polyamines have (Radical)-(OH)$_q$ and (Radical)-(NH$_2$)$_q$ structures, respectively, where (Radical) corresponds to an organic-containing radical and q is a positive integer from 3 to about 50. Note that, as described above, in Formula I, the variable "Q," when taken together with R, typically represents a residue of the core organic radical as described herein. That is to say, when describing polyols, polythiols and polymer amines, particularly by name, these molecules are referenced in their form prior to incorporation into a multi-armed polymer-containing structure (i.e., are referred to as their parent molecules). That is to say, when describing preferred organic core molecules, particularly by name, the core molecules are described in their precursor form, rather than in their radical form after removal of, for example, one or more protons. So, if for example, the organic core radical is derived from pentaerythritol, the precursor polyol possesses the structure C(CH$_2$OH)$_4$, and the organic core radical, together with Q, corresponds to C(CH$_2$O—)$_4$, where Q is O. So, for example, for a conjugate of Formula I wherein R taken together with Q is a residue of the polyol, pentaerythritol C(CH$_2$OH)$_4$, a residue R together with Q corresponds to "C(CH$_2$O—)$_4$", such that each of "q" polymer arms in the multi-armed polymer conjugate will emanate from each of the oxygen atoms of the pentaerythritol core or residue.

Illustrative polyols include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Exemplary polyols include glycerol, trimethylolpropane, pentaerythritol, dipentaerythritol, tripentaerythritol, ethoxylated forms of glycerol, trimethylolpropane, pentaerythritol, dipentaerythritol, tripentaerythritol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is also included as an exemplary polyol.

Exemplary polyamines include aliphatic polyamines such as diethylene triamine, N,N',N"-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methyl amine, and N,N-dimethyl-dipropylene-triamine. Naturally occurring polyamines that can be used include putrescine, spermidine, and spermine. Numerous suitable pentamines, tetramines, oligoamines, and pentamidine analogs suitable for use are described in Bacchi et al. (2002) *Antimicrobial Agents and Chemotherapy*, 46(1):55-61, which is incorporated by reference herein.

Provided below are illustrative structures corresponding to residues of polyols (although each structure is depicted with the oxygen atom ("O") derived from the corresponding hydroxyl group, each "O" can be substituted with sulfur ("S") or NH to depict the corresponding residue of a polythiol or polyamine, respectively). Note that the residues shown below would be understood in terms of conjugates of Formula I as corresponding to R taken together with Q to provide a multi-armed polymer conjugate having a number of arms corresponding to the number of oxygen (or other suitable heteroatom) atoms shown below.

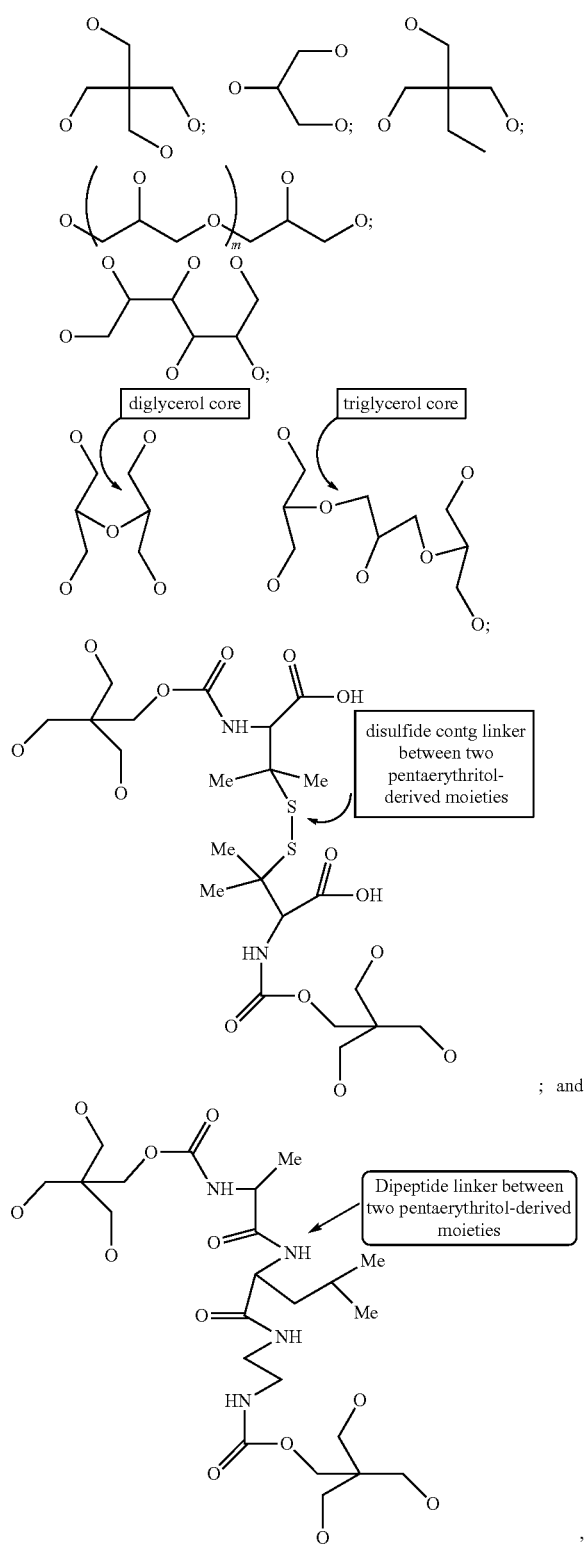

wherein m is a positive integer from 0-40 [e.g., 0-10, for example, 0-5 (i.e., 0, 1, 2, 3, 4, 5)]. The Water-Soluble, Non-Peptidic Polymer, "POLY".

The multi-arm polymer conjugates comprise a water-soluble, non-peptidic polymer. A wide array of polymers can be used and the structures provided herein are not limited with respect to the type (e.g., polyethylene oxide or polyoxazoline), or size (e.g., from 2 to 4,000 monomers in size) of water-soluble polymer.

With respect to type, the water-soluble, non-peptidic polymer is understood as a series of repeating monomers, wherein the type of monomer(s) dictates the type of water-soluble, non-peptidic polymer. Exemplary monomers include, but are not limited to alkylene oxides, such as ethylene oxide or propylene oxide; olefinic alcohols, such as vinyl alcohol, 1-propenol or 2-propenol; vinyl pyrrolidone; hydroxyalkyl methacrylamide and hydroxyalkyl methacrylate, where, in each case, alkyl is preferably methyl; α-hydroxy acids, such as lactic acid or glycolic acid; phosphazene, oxazoline, carbohydrates such as monosaccharides, alditol such as mannitol; and N-acryloylmorpholine. In one or more embodiments, the water-soluble, non-peptidic polymer is a co-polymer of two monomer types selected from this group, or, more preferably, is a homo-polymer of one monomer type selected from this group. With respect to co-polymers, which includes block copolymers, the two monomer types in a co-polymer may be of the same monomer type, for example, two alkylene oxides, such as ethylene oxide and propylene oxide.

With respect to size, the water-soluble, non-peptidic polymer can be a relatively small or the water-soluble, non-peptidic polymer can be relatively large.

In reference to POLY, that is to say, each polymer arm, in those embodiments in which a relatively small water-soluble, non-peptidic polymer is present, exemplary values of molecular weights include: below about 2000; below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons. Exemplary ranges for a relatively small water-soluble, non-peptidic polymer include from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

For relatively small water-soluble, non-peptidic polymers ("POLY"), the number of monomers in will typically fall within one or more of the following ranges: between 1 and about 30 (inclusive); between about 2 and about 25; between about 2 and about 20; between about 2 and about 15; between about 2 and about 12; between about 2 and about 10. In certain instances, the number of monomers in series in the polymer (and the corresponding conjugate) is one of 1, 2, 3, 4, 5, 6, 7, or 8. In additional embodiments, the polymer (and the corresponding conjugate) contains 9, 10, 11, 12, 13, 14, 15, 16, 17, 18, 19, or 20 monomers. In yet further embodiments, the polymer portion in each polymer "arm" (and the corresponding conjugate) possesses 21, 22, 23, 24, 25, 26, 27, 28, 29 or 30 monomers in series. Thus, for example, when the water-soluble, non-peptidic polymer arm comprises —(OCH$_2$CH$_2$)$_n$—, "n" is an integer that, in some embodiments, is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30, and can fall within one or more of the following ranges: between about 1 and about 25; between about 1 and about 20; between about 1 and about 15; between about 1 and about 12; between about 1 and about 10.

When the molecular weight of the overall water-soluble, non-peptidic polymer in the conjugate is relatively large (e.g., greater than 2,000 Daltons), the overall molecular weight can fall within the range of 2,000 Daltons to about 150,000 Daltons. Exemplary ranges, however, include molecular weights in the range of from about 3,000 Daltons to about 120,000 Daltons; in the range of from about 5,000 Daltons to about 110,000 Daltons; in the range of from greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary molecular weights for relatively large water-soluble, non-peptidic polymers, in reference to each of the polymer arms "POLY", in Formula I, include about 500 Daltons, about 750 Daltons, about 1,000 Daltons, about 1500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, and about 20,000 Daltons.

Exemplary molecular weights for relatively large water-soluble, non-peptidic polymers, in reference to the overall polymer portion of the multi-arm conjugate include, for example, about 20,000 Daltons 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble, non-peptidic polymer having a total molecular weight of any of the foregoing can also be used in each of the polymer arms to provide a multiply-branched conjugate.

Thus, regardless of whether a relatively small or large water-soluble, non-peptidic polymer is used, when the water-soluble, non-peptidic polymer is a poly(ethylene oxide), the polymer will comprise a number of $(OCH_2CH_2)$ monomers [or $(CH_2CH_2O)$ monomers, depending on how the PEG is defined]. As used throughout the description, the number of repeat units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

With respect to multi-arm water-soluble, non-peptidic polymers, these polymers typically contain three or more discernable water-soluble, non-peptidic polymer arms or segments. Among other benefits, multi-arm water-soluble, non-peptidic polymers—given the ability of each arm to covalently attach to a TLR 7/8 agonist—have the potential to provide greater drug character compared to, for example, a linear polymer having a single TLR 7/8 agonist attached thereto.

The Linkage-Containing Spacer Moiety, "Xr".

In reference to Formula I, the linkage-containing spacer moiety that generally covalently attaches POLY to the TLR 7/8 agonist can be hydrolytically and/or enzymatically stable or releasable at biologically relevant pHs. That is to say, in some embodiments, Xr is a hydrolytically stable linkage. In yet some other embodiments, Xr comprises a releasable linkage.

As described previously, a stable linkage is one that does not appreciably cleave in vivo following administration to a patient. In this regard, stable linkages are known to those of ordinary skill in the art. In addition, whether a given linkage serves as a stable linkage in connection with the conjugates provided herein can be tested through experimentation (e.g., by administering a conjugate having the proposed stable linkage to a patient and testing, e.g., via chromatographic or other suitable techniques, periodically obtained blood samples for indications of cleavage).

In some embodiments of a multi-arm conjugate, the linkage containing spacer moiety comprises a releasable linkage interposed between the TLR 7/8 agonist and the water-soluble, non-peptidic polymer. Thus, a releasable linkage is one that cleaves in vivo following administration to a patient, to thereby release the TLR 7/8 agonist compound (or a slightly modified version thereof, e.g., with a small molecular tag) from its polymer arm. In this regard, releasable linkages are known to those of ordinary skill in the art. In addition, whether a given linkage is releasable in nature in connection with the multi-armed conjugates provided herein can be tested through experimentation (e.g., by administering a conjugate having the proposed releasable linkage to a patient and testing, e.g., via chromatographic or other suitable techniques, periodically obtained blood samples for indications of cleavage). In some preferred embodiments, a multi-arm polymer conjugate of a TLR 7/8 agonist comprises a releasable linkage, that is to say, Xr comprises a releasable linkage.

For example, assessment of the releasable nature of a linkage comprised in a multi-armed polymer conjugate of a TLR 7/8 agonist can be determined in vitro after incubation of a conjugate sample with heparinized and pooled plasma (pH 7.2-7.4) from humans at 37° C. and samples withdrawn at various time points, where samples are immediately frozen until sample analysis and quantification, e.g., using any suitable technique for detection and quantification such as LC-MS. An apparent conversion half-life ($t_{1/2,app}$) is then calculated based on the assumption that the conjugate conversion from its initial nominal incubation concentration is attributed only to TLR 7/8 agonist release, where a $t_{1/2}$ of about 300 hours or less can be considered to be indicative of a releasable linkage or a releasable conjugate.

Exemplary releasable linkages for use in connection with the conjugates provided herein may include, without limitation, amide, thioether, carbamate, ester, carbonate, urea and enzyme-cleavable peptidic linkages, depending upon the structure of the TLR 7/8 agonist compound and the overall linker structure. In some instances, a bond or linkage may not generally be considered to be "releasable" or cleavable in nature, when considered alone, however, when taken together with the structure of the molecular entity to which it is covalently attached, e.g., a TLR 7/8 agonist compound having an imidazoquinoline structure, such linkage may releasable, due to particular release mechanism such as a beta-elimination, amide hydrolysis, or the like. For example, thioether, amide, carbamate, ester, carbonate, urea, and the like can cleave via a β-elimination reaction or via hydrolysis (with or without the enzymatic coordination, e.g., an ester can serve as a releasable linkage regardless of whether the ester is cleaved via an esterase).

Multi-arm polymer conjugates of a TLR 7/8 agonist comprising a releasable linkage are, in instances when release results in release of the unmodified parent molecule, often categorized as prodrugs, since they release the covalently attached TLR 7/8 agonist compound following administration (i.e., under physiological conditions). In general, the particular multi-arm polymer resiquimod conjugates described herein comprise releasable linkages to resiquimod.

With respect to enzyme-cleavable peptidic linkages, the spacer moiety can include one or more of a series of amino acids known to be a substrate for an enzyme present in the intended patient population. In this way, upon administration to the patient, enzymatic-induced cleavage of the enzyme-cleavable peptidic linkage comprised in the conjugate will release a TLR 7/8 agonist (or a TLR 7/8 agonist with a relatively small molecular fragment or "tag" resulting from the cleavage). Examples of peptidic linkages subject to enzymatic cleavage in a given patient population are described, for example, in U.S. Patent Application Publication No. US 2005/0079155, and can also be determined experimentally.

In reference to Xr, the linkage-containing spacer moiety may comprise any of a number of exemplary amino acids, such a beta-alanine, glycine, L-alanine, L-valine, leucine, dimethylglycine and the like. In some embodiments, Xr comprises a carboxymethyl group, —CH$_2$C(O)— covalently attached to any one or more of the foregoing amino acids via its amino group, wherein its terminal carboxy group is covalently attached to an amino group of the TLR 7/8 agonist to provide an amide linkage, which in some embodiments, is releasable.

In some embodiments, the linkage-containing spacer moiety, "Xr," is in accordance with Formula II:

~[X$^1$]$_a$-[Lr]$_b$-X$^2$~ (Formula II)

wherein "a" is zero or one (such that zero represents absence of "X$^1$" and one indicates its presence); "b" is zero or one (such that zero represents absence of "Lr" and one indicates its presence); X$^1$, when present, is a spacer; Lr, when present, is a linkage; and X$^2$ is a functional group directly covalently attached to the TLR 7/8 agonist.

In those instances of Formula II wherein a and b are both zero, it will be understood that the linkage-containing spacer is made up of X$^2$, the functional group that covalently attaches the TLR 7/8 agonist to the remainder of the multi-arm polymer (e.g., to a polymer arm, POLY). In such an instance, the linkage-containing spacer only contains the functional group X$^2$ and no other atoms are present between the TLR 7/8 agonist and the water-soluble, non-peptidic polymer. Typically, X$^2$ comprises an atom or atoms of the unmodified TLR 7/8 agonist to which the remainder of the multi-arm polymer is covalently attached. For example, if attachment occurs at an amino group of the TLR 7/8 agonist, typically the amino group forms part of X$^2$.

In those instances of Formula II wherein either or both of a and b are one, it will be understood that the linkage-containing spacer contains one or more additional atoms other than those that make up X$^2$. Non-limiting exemplary X$^1$ and Lr, when considered either left to right or right to left, include —O—, —NH—, —S—, —C(O)—, —C(O)O—, —OC(O)—, —CH$_2$—C(O)O—, —CH$_2$—OC(O)—, —C(O)O—CH$_2$—, —OC(O)—CH$_2$—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, a bivalent cycloalkyl group, —N(R$^6$)—, where R$^6$ is H or an organic radical selected from the group consisting of alkyl, substituted alkyl, alkenyl, substituted alkenyl, alkynyl, substituted alkynyl, aryl and substituted aryl, and combinations of one or more of the foregoing. Additional spacers and linkages include acylamino, acyl, aryloxy, alkylene bridge containing between 1 and 5 inclusive carbon atoms, alkylamino, dialkylamino having about 2 to 4 inclusive carbon atoms, piperidino, pyrrolidino, N-(lower alkyl)-2-piperidyl, morpholino, 1-piperizinyl, 4-(lower alkyl)-1-piperizinyl, 4-(hydroxyl-lower alkyl)-1-piperizinyl, 4-(methoxy-lower alkyl)-1-piperizinyl, fluorenyl, and guanidine. For purposes of the present description, however, a group of atoms is not considered a spacer when it is immediately adjacent to a polymeric segment, and the group of atoms is the same as a monomer of the polymer such that the group would represent a mere extension of the polymer chain.

When present, a spacer and or linkage is typically but is not necessarily linear in nature. In addition, a spacer and/or linkage is typically but is not necessarily hydrolytically stable and/or is enzymatically stable. In one or more embodiments, a spacer or linkage, when present, has a chain length of less than about 12 atoms (e.g., less than about 10 atoms, less than about 8 atoms, and less than about 5 atoms).

With respect to determining length of a particular spacer or linkage, length herein is defined as the number of atoms in a single chain, not counting substituents. For instance, a urea linkage such as this, R-POLY-NH—(C=O)—NH-TLR 7/8 Agonist, is considered to have a chain length of three atoms (—NH—C(O)—NH—).

In reference to Formula II, a particular example of $X^1$, when present, includes —CH$_2$C(O)— (referred to herein as carboxy methyl).

Examples of $X^2$ include, —C(O)—NH— (where NH is a point of attachment to the TLR 7/8 agonist, and forms part of the unmodified TLR agonist prior to covalent attachment); —NH—C(O)—NH— (where NH is a point of attachment to the TLR 7/8 agonist and forms part of the unmodified TLR agonist prior to covalent attachment); —NH—C(O) (where the carbonyl carbon represents a point of attachment to the TLR 7/8 agonist and forms part of the unmodified TLR agonist prior to covalent attachment), and —NH (where the nitrogen atom represents a point of attachment to the TLR 7/8 agonist and forms part of the unmodified TLR agonist prior to covalent attachment).

Examples of Lr include —(CR$_x$R$_y$)$_z$—, and —NH (CR$_x$R$_y$)$_z$— where each R$_x$ and R$_y$ is independently selected from hydrogen, lower alkyl, halo (X), and halo-substituted lower alkyl, and z is an integer from 1 to 6, e.g., is selected from 1, 2, 3, 4, 5, and 6. Examples of lower alkyl include methyl, ethyl, propyl, butyl, isobutyl, sec-butyl, pentyl, and hexyl; exemplary halo groups are fluoro, chloro, bromo, iodo. Illustrative Lr groups include, e.g., —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CHF—, —CHCH$_3$—, —CHCH(CH$_3$)$_2$—, —CHCH$_2$CH(CH$_3$)$_2$—, —C(CH$_3$)$_2$—, —NHCH$_2$—, —NHCH$_2$CH$_2$—, —NHCH$_2$CH$_2$CH$_2$—, —NHCH$_2$CH$_2$CH$_2$CH$_2$—, —NHCH$_2$CH$_2$CH$_2$CH$_2$CH$_2$—, —NHCH$_2$CH$_2$CH$_2$CH$_2$CH$_2$CH$_2$—, —NHCH$_2$CHF—, —NHCHCH$_3$—, —NHCHCH(CH$_3$)$_2$—, —NHCHCH$_2$CH(CH$_3$)$_2$—, and —NHC(CH$_3$)$_2$—. Additional structures are provided herein.

TLR 7/8 Agonists

Turning now to the TLR 7/8 agonist that is comprised in the multi-arm polymer conjugates described herein, a TLR 7/8 agonist is any compound that is an agonist to Toll-like receptor 7 and/or Toll-like receptor 8. Preferably, the TLR 7/8 agonist is a small molecule agonist. Illustrative structural classes include guanosine-containing compounds and imidazoquinolines.

Illustrative TLR 7/8 agonist compounds include, for example, 3M-052 (MEDI-9797), R848 (S-28463), R837 (S-26308), S-28690, 3M-001 (852A, PF-4878691, TMX-101), GS-9620), ANA-773, AZD8848, CL097, CL057 (3M-002), 3M-003, TMX-202, TMX-302, TMX-306, IV136, IV209, 3M-011, SM-276001, SM-324405, SM-324405, SM-360320, PF-4171455, CpG, CpR, ssRNA, BHMA, SM-324405, AZ12441970, and AZ12443988.

For example, the TLR 7/8 agonist may be selected from following: 4-((6-amino-8-hydroxy-2-(2-methoxyethoxy)-9H-purin-9-yl)-methyl)-N-(20-azido-3,6,9,12,15,18-hexaoxaicosyl)benzamide; 3-(1-(1-(4-((6-amino-8-hydroxy-2-(2-methoxyethoxy)-9H-purin-9-yl)methyl)phenyl)-1-oxo-5,8,11,14,17,20-hexaoxa-2-azadocosan-22-yl)-1H-1,2,3-triazol-4-yl)propanoic acid; 4-((6-amino-8-hydroxy-2-(2-methoxyethoxy)-9H-purin-9-yl)-methyl)-N-(20-amino-3,6,9,12,15,18-hexaoxaicosyl)benzamide; 4-((6-amino-8-hydroxy-2-(2-methoxyethoxy)-9H-purin-9-yl)methyl)-N-(32-azido-3,6,9,12,15,18,21,24,27,30-decaoxa-yl)methyl)-N-(32-azido-3,6,9,12,15,18,21,24,27,30-decaoxadotriacontyl)benzamide; 3-(1-(1-(4-((6-amino-8-hydroxy-2-(2-methoxyethoxy)-9H-3-(1-(1-(4-((6-Amino-8-hydroxy-2-(2-methoxyethoxy)-9Hpurin-9-yl)methyl)phenyl)-1-oxo-5,8,11,14,17,20,23,26,29,32-decaoxa-2-azatetratriacontan-34-yl)-1H-1,2,3-triazol-4-yl)-propanoic acid; 4-((6-amino-8-hydroxy-2-(2-methoxyethoxy)-9H-purin-9-yl)methyl)-N-(32-amino-3,6,9,12,15,18,21,24,27,30-decaoxadotriacontyl)-benzamide; 4-((6-amino-8-hydroxy-2-(2-methoxyethoxy)-9H-purin-9-yl)methyl)-N-(59-amino-3,6,9,12,15,18,21,24,27,30,33,36,39,42,45,48,51,54,57-nonadecaoxanonapentacontyl)benzamide; {N-[4-(4-amino-2-ethyl-1H-imidazo[4,5c]quinolin-1-yl)butyl] methanesulfonamide}; [8-(3-(pyrrolidin-1-ylmethyl)benzyl)-4-amino-2-butoxy-7,8-dihydropteridin-6(5H)-one]; [2-(4-((6-amino-2-(2-methoxyethoxy)-8-oxo-7H-purin-9(8H)-yl) methyl) benzamido) ethyl 2,3-Bis (dodecanoyloxy) propyl phosphate]; [1-(4-((6-amino-2-(2-methoxyethoxy)-8-oxo-7H-purin-9(8H)-yl) methyl) phenyl)-1-oxo-5,8,11,14,17,20-hexaoxa-2-azatricosan-23-oic acid]; [9-benzyl-8-hydroxy-2-(2-methoxyethoxy) adenine; methyl 2-(3-{[6-amino-2-butoxy-8-oxo-7H-purin-9(8H)-yl]methyl}phenyl) acetate, SM-324406: 2-(3-{[6-amino-2-butoxy-8-oxo-7H-purin-9(8H)-yl]methyl}phenyl)acetic acid; methyl 2-(3-(((3-(6-amino-2-butoxy-8-oxo-7H-purin-9(8H)-yl)propyl) (3-(dimethylamino)propyl)amino)phenyl) acetate; and 2-(3-(((3-(6-amino-2-butoxy-8-oxo-7H-purin-9(8H)-yl)propyl) (3-(dimethylamino)propyl)amino)phenyl).

In some particular embodiments of a multi-arm polymer conjugate of a TLR 7/8 agonist, the TLR 7/8 agonist is 3M-052 (MEDI-9797), R848 (S-28463), R837 (S-26308), S-28690, 3M-001 (852A, PF-4878691), TMX-101, GS-9620, ANA-773, AZD8848, CL097, SM-324405, AZ12441970, GSK2245053, SZ-101, 4-[6-amino-8-hydroxy-2-(2-methoxyethoxy)purin-9-ylmethyl]benzaldehyde (UC-1V150), 9-benzyl-8-hydfroxy-2-(2-merthoxyethoxy) adenine (SM360320, 1V136), VTX-1463 and VTX-2337. In yet some other embodiments, the TLR 7/8 agonist is (N-[4-(4-amino-2-ethyl-1H-imidazo[4,5c]quinolin-1-yl)butyl] methanesulfonamide or [8-(3-(pyrrolidin-1-ylmethyl)benzyl)-4-amino-2-butoxy-7,8-dihydropteridin-6(5H)-one].

In certain preferred embodiments, the TLR 7/8 agonist is an imidazoquinoline compound. Illustrative imidazoquinolines include, for example, 1-substituted, 2-substituted 1H-imidazo[4,5-c]-quinolin-4-amine compounds such as described in U.S. Pat. No. 5,389,640. Such compounds include 4-amino-7-chloro-alpha, alpha-dimethyl-2-ethoxymethyl-1H-imidazo[4,5-c]quinoline-1-ethanol; 4-amino-alpha, alpha-dimethyl-2-hydroxymethyl-1H-imidazo[4,5-c]quinoline-1-ethanol; 4-amino-alpha, alpha-dimethyl-2-methoxymethyl-1H-imidazo[4,5-c]quinoline-1-ethanol; 2-ethoxymethyl-1-(3-methoxypropyl)-1H-imidazo [4,5-c]quinolin-4-amine; and 1-(2-methoxyethyl)-2-methoxymethyl-1H-imidazo[4,5-c]quinolin-4-amine.

In one or more preferred embodiments, the TLR 7/8 agonist is resiquimod (R-848) or imiquimod (1-isobutyl-1H-imidazo[4,5-c]quinolin-4-amine), or is a derivative thereof.

In one or more particular embodiments, the TLR 7/8 agonist is imiquimod,

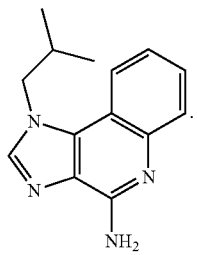 [SMILES: CC(C)Cn1cnc2c(N)nc3ccccc3c21]

In yet certain other particular embodiments, the TLR 7/8 agonist is resiquimod,

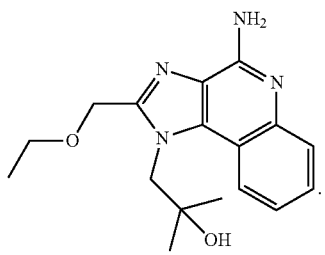

R-848

Covalent attachment of the TLR 7/8 agonist to the multi-armed polymer may take place via attachment to any suitable functional group or atom on the TLR 7/8 agonist compound. Illustrative functional groups suitable for attachment to the multi-armed polymer include amino, hydroxyl, carboxy, and thiol, and the like. In certain preferred embodiments, covalent attachment to imiquimod takes place at the aromatic —$NH_2$ group. In other preferred embodiments, covalent attachment to resiquimod takes place at the aromatic —$NH_2$ group. Exemplary structures are provided below.

Methods for Synthesizing Conjugates.

The conjugates described herein can be prepared in a variety of methods, and exemplary syntheses are provided in the examples which follow.

In one example, the conjugates are prepared by a method comprising covalently attaching a multi-arm water-soluble, non-peptidic reactive polymer to a TLR 7/8 agonist. Many TLR 7/8 agonists can be obtained commercially or synthesized by methods known to those of skill in the art.

With respect to the reactive multi-arm water-soluble, non-peptidic polymer, such polymers can be obtained commercially in a form bearing one or more reactive groups, thereby providing a reagent suited for covalent attachment to a TLR 7/8 agonist, or can be synthesized directly via alkoxylation as described in PCT Publication No. WO 2011/063156. In this form, the water-soluble, non-peptidic polymer is often referred to as a polymeric reagent or as an activated polymer.

As an example, any of a number of suitable polyol core materials can be purchased from a chemical supplier such as Aldrich (St. Louis, Mo.). The terminal hydroxyls of the polyol are first converted to their anionic form, using, for example, a strong base, to provide a site suitable for initiating polymerization, followed by direct polymerization of monomer subunits, e.g., ethylene oxide, onto the core. Chain building is allowed to continue until a desired length of polymer chain is reached in each of the arms, followed by terminating the reaction, e.g., by quenching, and optionally, introduction of suitable reactive groups.

In an alternative approach, an activated multi-armed polymer precursor can be synthetically prepared by first providing a desired polyol core material, and reacting the polyol under suitable conditions with a heterobifunctional PEG mesylate of a desired length, where the non-mesylate PEG terminus is optionally protected to prevent reaction with the polyol core. The resulting multi-armed polymer precursor is then suitable for additional transformations or direct coupling to a TLR 7/8 agonist, following deprotection if necessary.

Commercial suppliers for such polymeric reagents include Sigma-Aldrich (St. Louis, Mo.), Creative PEG-Works (Winston Salem, N.C. USA), SunBio PEG-Shop (SunBio USA, Orinda, Calif.), JenKem Technology USA (Allen, Tex.), and NOF America Corporation (White Plains, N.Y.) (see, for example, the SUNBRIGHT series of multi-arm polymers having 4 or 8 polymer arms, or the branched polymer series having 3 or 4 polymer arms extending from a polyol core). Using routine experimentation, one of ordinary skill in the art can identify multi-arm polymeric reagents having sizes, architectures, and reactive groups and so forth for preparing the subject TLR 7/8 agonist conjugates.

For example, it is possible to prepare a series of conjugates wherein each member in the series differs in a feature (e.g., the size of the water-soluble, non-peptidic polymer, the type of reactive groups, the ability of a linkage to release, and so forth) and then administer one member in the series to a patient followed by periodic detection and quantification (e.g., using chromatographic techniques) of blood and/or urine samples. Each member of the series is administered and quantified in a similar way to a naïve patient. Once each member of the series is tested, the results can be reviewed to determine which feature(s) provide conjugates having the desired effect(s).

Covalently attaching the polymeric reagent to a TLR 7/8 agonist is typically conducted under conjugation conditions, which conditions include combining a TLR 7/8 agonist with a polymeric reagent (often a molar excess of the multi-armed polymeric reagent relative to the TLR 7/8 agonist) under conditions of temperature, pH, time and solvent that allow for covalent attachment between reactive groups of the multi-arm polymeric reagent to a reactive group on the TLR 7/8 agonist. In one or more particular embodiments, the reactive group is a reactive amino group.

Exemplary polymeric reagents will have a structure akin to Formula I, e.g., R—(Q-POLY-Y)$_q$, where Y represents Xr in Formula I, with the exception that Y terminates in a functional group effective to react with a reactive group or atom of the TLR 7/8 agonist to provide the ultimate covalent attachment to the TLR 7/8 agonist compound. For instance, in reference to Formula II, Y is akin to ~$[X^1]_a$-$[Lr]_b$-$X^2$~ with the exception that rather than comprising $X^2$, the direct covalent attachment to the TLR 7/8 agonist, Y has a structure according to Formula II', ~$[X^1]_a$-$[Lr]_b$-$X^{pre-2}$~, where each of the variables is as described above for Formula II, with the exception of $X^{pre-2}$, which represents a reactive group suitable for reaction with a reactive group or atom of the TLR 7/8 agonist (i.e., an $X^2$ group precursor), such that coupling with the TLR 7/8 agonist results in a covalent linkage, $X^2$.

In some embodiments, a multi-armed polymeric reagent is selected such that (i) the reactive group(s) of the polymeric reagent form a covalent attachment at a reactive group of the TLR 7/8 agonist, and (ii) the polymeric reagent includes a releasable linkage (i.e., prior to covalently attachment to a TLR 7/8 agonist) or results in formation of a releasable linkage (e.g., following covalent attachment of the multi-arm polymer reagent to the TLR 7/8 agonist).

In yet some other embodiments, the multi-armed polymeric reagent is selected such that (i) the reactive group of the polymeric reagent forms a covalent attachment at a reactive group of the TLR 7/8 agonist, and (ii) the polymeric reagent comprises a stable linkage (e.g., prior to covalent attachment to a TLR 7/8 agonist) or results in formation of a stable linkage (e.g., following covalent attachment to the TLR 7/8 agonist).

Illustrative reactive groups for forming a covalent attachment to a small molecule such as a TLR 7/8 agonist e.g., $X^{pre-2}$, include N-succinimidyl carbonate, amine, hydrazide, succinimidyl propionate, succinimidyl butanoate, succinimidyl succinate, succinimidyl ester, benzotriazole carbonate, glycidyl ether, oxycarbonylimidazole, p-nitrophenyl carbonate, aldehyde, maleimide, orthopyridyl-disulfide, acrylol, vinylsulfone, and the like. In one or more embodiments, $X^{pre-2}$ is carboxyl or is an activated ester.

In some exemplary embodiments, a multi-arm polymer reagent having an activated carboxy methyl group at the terminus of each of its polymer arms (e.g., an NHS ester of a carboxymethyl group) is covalently attached to an amino acid, e.g., a beta-alanine, glycine, L-alanine, L-valine, leucine, dimethylglycine, and so forth, to provide an activated multi-armed polymeric reagent suitable for coupling to a TLR 7/8 agonist as described herein.

Exemplary conjugation conditions between a given polymeric reagent bearing a reactive group and a reactive group on a TLR 7/8 agonist will be known to one of ordinary skill in the art based upon the disclosure provided herein and in the context of the relevant literature. See, for example, *Poly(ethylene glycol) Chemistry and Biological Applications*, American Chemical Society, Washington, D.C. (1997). Representative detailed examples for preparing the subject multi-arm polymer conjugates are provided in the accompanying supporting Examples. See, for example, Examples 1-16.

Certain features of a multi-arm polymer conjugate of a TLR 7/8 agonist are preferred and each of these features as described below is to be considered individually and explicitly in combination. In some preferred embodiments, each of the polymer arms emanating from the central core is the same. That is to say, for example, in reference to Formula I, emanating from R, each Q, POLY, Xr and TLR 7/8 agonist is the same. In certain preferred embodiments, q is 4. In other preferred embodiments, the multi-arm polymer conjugate comprises a pentaerythritol core. In yet some further embodiments, the TLR 7/8 agonist is resiquimod. In yet some additional embodiments, POLY is a polyethylene glycol and POLY-Xr comprises —CH$_2$—C(O)-amino acid-, where the amino acid is selected from beta-alanine, glycine, L-alanine, L-valine, leucine, H$_2$NCH$_2$CHFCOOH, and dimethylglyine, and the amino group of the amino acid is directly attached to the carbonyl group. In yet further embodiments of the foregoing, the amino acid is glycine. In yet some further embodiments, the multi-arm polymer conjugate is Compound 6.

Exemplary Conjugates

Representative conjugates having features as described above are provided below. For example, a conjugate may have a structure as defined by Formula III:

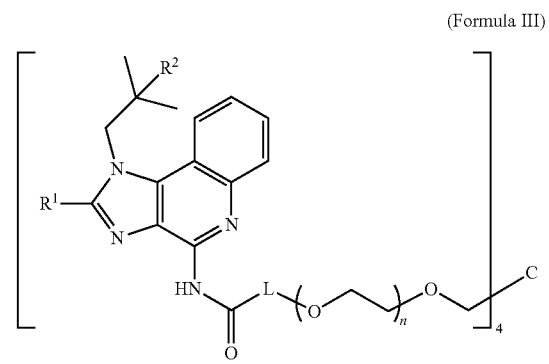

(Formula III)

or a pharmaceutically acceptable salt or stereoisomer thereof, wherein L is —(CH$_2$)$_m$—, —(CH$_2$)$_m$—NH—C(O)—(CH$_2$)$_m$—, —CHF—(CH$_2$)$_m$—NH—C(O)—(CH$_2$)$_m$—, —CH(CH$_3$)—NH—C(O)—(CH$_2$)$_m$—, —(CH$_2$)$_m$—CH(CH(CH$_3$)$_2$)—NH—C(O)—(CH$_2$)$_m$—, —(CH$_2$)$_m$—CH(CH$_2$CH(CH$_3$)$_2$)—NH—C(O)—(CH$_2$)$_m$—, —C(CH$_3$)$_2$—NH—C(O)—(CH$_2$)$_m$—, a single bond, or —NH—(CH$_2$)$_m$—; each m is independently an integer from 1 to 5, inclusive; each n is independently an integer from 40 to 350, inclusive; R$^1$ is hydrogen or —CH$_2$—O—CH$_2$—CH$_3$; and R$^2$ is hydrogen or hydroxyl.

In particular conjugates of Formula III, L is selected from, for example, —CH$_2$—, —CH$_2$—CH$_2$—NH—C(O)—CH$_2$—, —CH$_2$—CH$_2$—CH$_2$—, —CHF—CH$_2$—NH—C(O)—CH$_2$—, —CH$_2$—NH—C(O)—CH$_2$, —CH(CH$_3$)—NH—C(O)—CH$_2$—, —CH$_2$—CH(CH(CH$_3$)$_2$)—NH—C(O)—CH$_2$—, —CH$_2$—CH(CH$_2$CH(CH$_3$)$_2$)—NH—C(O)—CH$_2$—, —C(CH$_3$)$_2$—NH—C(O)—CH$_2$—, a single bond, and —NH—CH$_2$—CH$_2$—.

Some specific embodiments of Formula III are as follows.

For example, in some embodiments, each n is independently an integer from 100 to 250, inclusive.

In some conjugates of Formula III, R$^1$ is hydrogen and R$^2$ is hydrogen.

In yet further conjugates of Formula III, R$^1$ is —CH$_2$—O—CH$_2$—CH$_3$ and R$^2$ is hydroxyl.

Particular multi-armed conjugates have structures as follows. That is to say, in some embodiments, a multi-armed polymer conjugate has a structure of any one of Compounds 1-10 or 12-16:

Compound 1
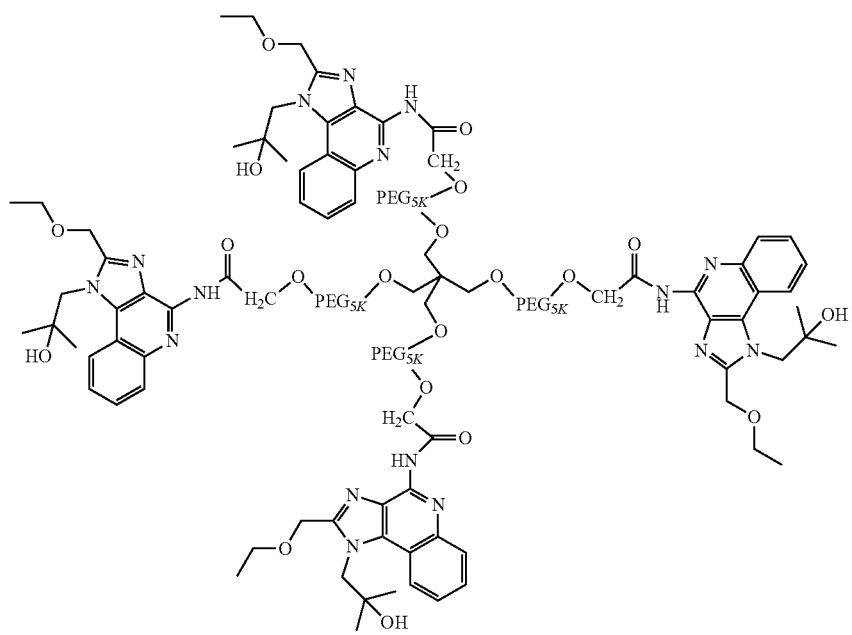
Compound 2
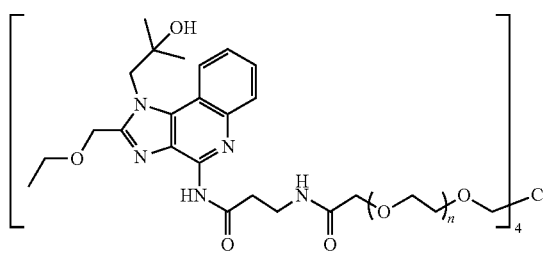
Compound 3
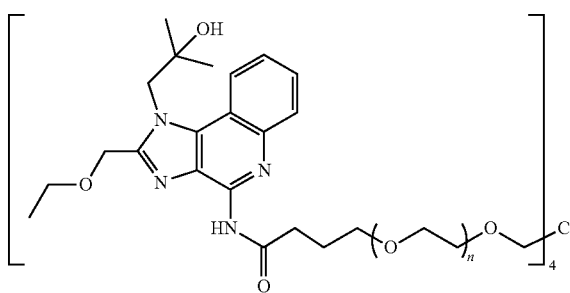
Compound 4
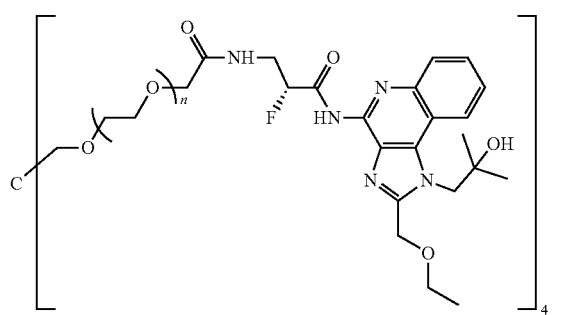
Compound 5
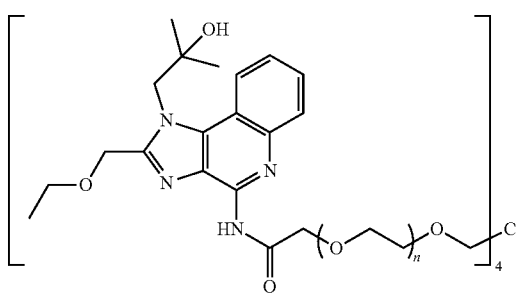
Compound 6
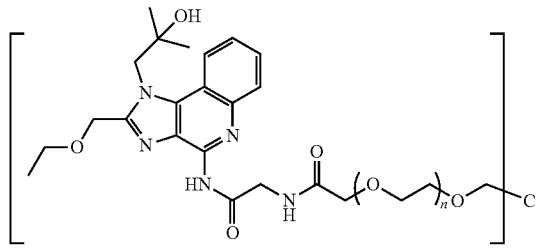
Compound 7
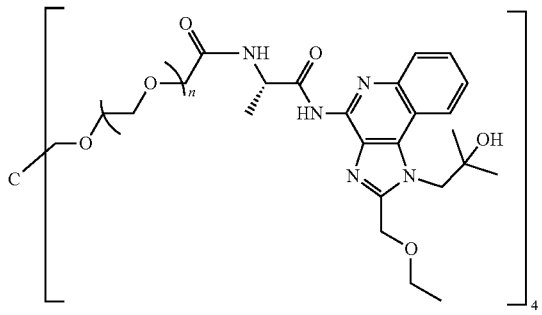

-continued

Compound 8

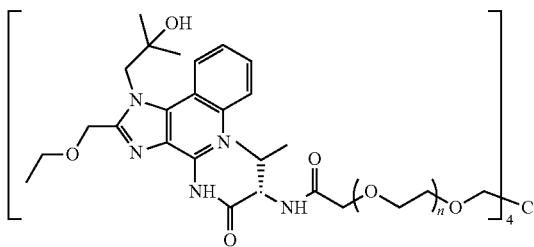

Compound 9

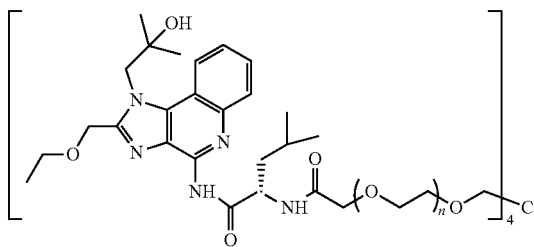

Compound 10

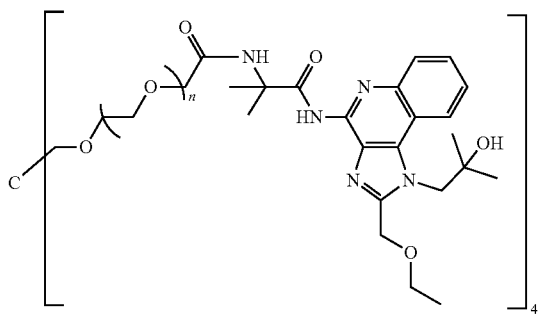

Compound 12

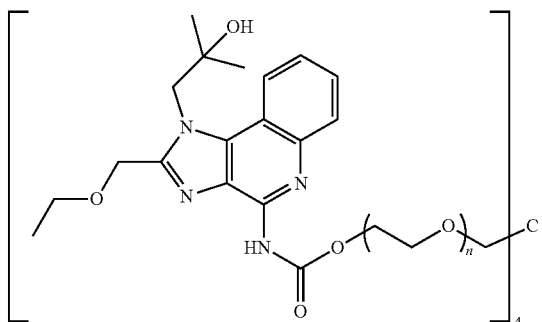

Compound 13

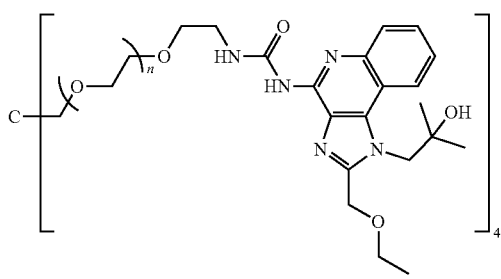

Compound 14

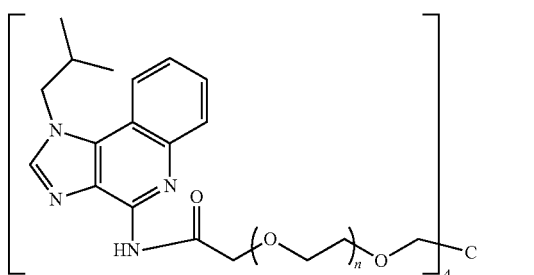

Compound 15

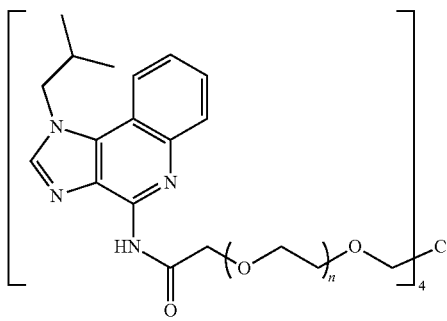

Compound 16

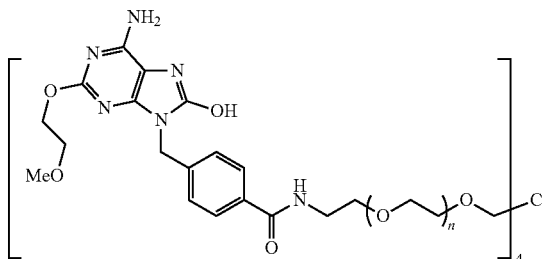

or a pharmaceutically acceptable salt or stereoisomer thereof.

In some embodiments, due to incomplete chemical conversion (i.e., covalent coupling to a TLR 7/8 agonist), less than 100% yields, and/or other unavoidable complications routinely encountered during chemical syntheses, exemplary compositions comprising a multi-arm polymer conjugate will comprise fewer than the idealized number of TLR 7/8 agonist compounds attached to each of the number of "q" polymer arms. Such number is typically referred as degree of polymer loading, wherein 100% loading represents complete loading such that a TLR 7/8 agonist compound is covalently attached to the terminus of each of "q" polymer arms. For instance, an exemplary "4-arm-PEG" conjugate can be characterized as a mixture comprising four-arm conjugates, wherein at least 50 area percent (a/a, as measured by HPLC) of the four-arm conjugates in the composition have each of the four arms conjugated to a TLR 7/8 agonist. Further exemplary compositions comprising an exemplary "4-arm-PEG" conjugate can be characterized as compositions comprising four-arm conjugates, wherein at least 65-90, 70-85, or 70-75 area percent (a/a, as measured by HPLC) of the four-arm conjugates in the composition have each of the four arms conjugated to a TLR 7/8 agonist.

Compositions

The conjugates may be administered per se or in the form of a pharmaceutically acceptable salt, and any reference to the any one or more of the multi-arm polymer conjugates herein is intended to include pharmaceutically acceptable salts. If used, a salt of a conjugate as described herein should be both pharmacologically and pharmaceutically acceptable. Such pharmacologically and pharmaceutically acceptable salts can be prepared by reaction of the conjugate with an organic or inorganic acid, using standard methods detailed in the literature. Examples of useful salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, malonic, succinic, naphthalene-2-sulphonic and benzenesulphonic, trifluoracetic acid, and the like. Also, pharmaceutically acceptable salts can be prepared as alkaline metal or alkaline earth salts, such as sodium, potassium, or calcium salts of a carboxylic acid group.

The conjugates, and in particular, the TLR 7/8 agonist portions of the conjugates, may contain one or more chiral centers. For each chiral center comprised therein, the instant compounds and structures are intended to encompass each optical isomer as well as any combination or ratio of or an optically active form, for example, a single optically active enantiomer, or any combination or ratio of enantiomers (e.g., scalemic and racemic mixtures). In addition, the small molecule drug may possess one or more geometric isomeric forms, and each is considered to be encompassed herein. With respect to geometric isomers, a conjugate can comprise a single geometric isomer or a mixture of two or more geometric isomers, although preferred is a single geometric isomer within a particular multi-arm polymer conjugate structure.

Also provided herein are pharmaceutical preparations comprising a multi-arm polymer conjugate of a TLR 7/8 agonist as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, maltitol, lactitol, xylitol, sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Non-limiting examples of suitable antimicrobial agents include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines, fatty acids and fatty esters; steroids, such as cholesterol; and chelating agents, such as EDTA, zinc and other such suitable cations.

Pharmaceutically acceptable acids or bases may be present as an excipient in the preparation. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

Other pharmaceutical excipients and/or additives suitable for use in the compositions according to the disclosure and related methods for formulation can be found in, for example, "Remington: The Science & Practice of Pharmacy", 22nd Ed., Remington: The Essentials of Pharmaceutics (2009); and in the "Physician's Desk Reference", 2017, and in "Handbook of Pharmaceutical Excipients", $7^{th}$ edition.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. The optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, excipients will be present in the composition in an amount of about 1% to about 99% by weight, preferably from about 5%-98% by weight, more preferably from about 15-95% by weight of the excipient, with concentrations less than 30% by weight most preferred.

The pharmaceutical compositions can take any number of forms and the composition is not limited in this regard. Exemplary preparations may be in a form suitable for oral administration such as a tablet, caplet, capsule, gel cap, troche, dispersion, suspension, solution, elixir, syrup, lozenge, transdermal patch, spray, suppository, and powder. In a preferred embodiments, the composition is a form suitable for intratumoral administration.

Oral dosage forms include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, flow agents, and the like. Binders are used to impart cohesive qualities to a tablet, and thus ensure that the tablet remains intact. Suitable binder materials include, but are not limited to, starch (including corn starch and pre-gelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethylcellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or cross-linked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (as a lyophilizate or precipitate, which can be in the form of a powder or cake), as well as formulations prepared for injection, which are liquid and require the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of non-aqueous solutions, suspensions, or emulsions, normally being sterile. Examples of non-aqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugates can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugates can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

In some preferred embodiments, a conjugate or composition comprising a conjugate is administered intratumorally, e.g, administered directly into a tumor, e.g., by injection. Such administration provides for a high concentration of the TLR 7/8 agonist to be achieved in the tumor, with delayed release of the TLR 7/8 agonist into the systemic circulation, and in the case of a conjugate comprising releasable linkages, into the tumor itself. An exemplary formulation for intratumoral administration of a multi-arm polymer conjugate of a TLR 7/8 agonist comprises Na/K phosphate buffer at pH 7.4.

In some embodiments, the compositions comprising the conjugates may further be incorporated into a suitable delivery vehicle. Such delivery vehicles may provide controlled and/or continuous release of the conjugates and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* species are preferred; however, any yeast cell may be used. These yeast cells exhibit different properties in terms of hydrodynamic volume and also differ in the target organ where they may release their contents. The methods of manufacture and characterization of these particles are described in U.S. Pat.

Nos. 5,741,495, 4,810,646, 4,992,540, 5,028,703, 5,607,677 and U.S. Patent Application Publication Nos. 2005/0281781 and 2008/0044438.

Also provided is a method for administering a multi-arm polymer conjugate of a TLR 7/8 agonist as provided herein to a patient suffering from a condition that is responsive to treatment with the conjugate, such as for example, a patient having cancer. The method comprises administering a therapeutically effective amount of the conjugate (preferably provided as part of a pharmaceutical preparation), where illustrative modes of administration include, in addition to oral administration, routes such as pulmonary, nasal, buccal, rectal, sublingual, transdermal, intratumoral, and parenteral. As used herein, the term "parenteral" includes subcutaneous, intravenous, intra-arterial, intraperitoneal, intracardiac, intrathecal, and intramuscular injection, as well as infusion injections.

In certain embodiments, the cancer is a solid cancer. For example, the cancer may be selected from the group consisting of breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Hodgkin's disease and adrenocortical cancer.

In instances where parenteral administration is utilized, it may be useful to employ somewhat bigger polymers, for example with molecular weights ranging from about 500 to 60,000 Daltons (e.g., having molecular weights of about 500, 1000, 2000, 2500, 3000, 5000, 7500, 10000, 15000, 20000, 25000, 30,000, 40,000, 50,000 or more).

In an embodiment, a method is provided, the method being directed to a method of treating cancer, which method comprises administering to a patient a pharmaceutical composition comprising a conjugate as described herein.

In an embodiment, provided herein is a use of a conjugate as described herein in the preparation of a medicament which is useful in the treatment of cancer, such as a solid cancer.

The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

Treatment of a Subject Having Cancer by Administering a Toll-Like Receptor (TLR) Agonist in Combination with a Long-Acting IL-2RB-Biased Agonist Administration of IL-2Rβ-selective agonists has been suggested as being beneficial to patients suffering from certain cancers by targeting the adaptive immune system. Such administration is expected to reduce the immune-suppressing effects of regulatory T-cells while increasing CD8+ memory T-cells, to thereby recruit the patient's own immune system to eliminate cancer cells. See for example, Charych et al., AACR 2013, Abstract #482.

Recruiting the immune system of a cancer patient in the treatment of cancer via administration of IL-2Rβ-selective agonists—which can be directly immunoactivating—can, in some cases, be further enhanced, for example, through the administration of additional agents. However, numerous challenges arise when trying to activate cytotoxic immune responses against tumors by administering more than one immunomodulating substance. For instance, in some cases, the administration of a second immunomodulator can actually attenuate or suppress rather than enhance the cytotoxic effect of a first immunomodulator, which when administered as a single agent (i.e., as a monotherapy) promotes a strong antitumor response. In cancer immunotherapy, achieving a favorable balance between immune stimulation and immune inhibition to provide an effective antitumor response, especially when administering multiple active agents, represents a significant challenge.

TLR agonists have been investigated for their antitumor properties, however, in general, most TLR agonists have underperformed as cancer therapeutics. It has been postulated that such underperformance might be explained by a mechanism in which induction of immune suppressive factors dampens TLR agonist-induced inflammation. (Lu, H. *Frontiers in Immunology*, March 2014, 5, 83). For example, TLR agonists have immune stimulatory effects through the induction of co-stimulatory molecules such as CD80, CD86, and CD40 on dendritic cells and inflammatory cytokines such as TNF-α and IL-12 that polarize the immune response. However, TLR agonists also have immune inhibitory effects, e.g., by inducing several immune suppressive factors including IL-10, regulatory T cells (Tregs), and PD-1, all of which can suppress anti-tumor immunity (Lu, H., 2014, ibid). Thus, a notable challenge exists in trying to arrive at an immunotherapeutic combination in which both components interact favorably to provide an enhanced therapeutic effect.

As discussed above, although there have been substantial efforts in developing effective cancer immunotherapies encompassing various platforms to date, there remains a need to identify and provide new and more effective immunotherapeutic treatment regimens, for example, for treating cancer. This and other aspects of present disclosure seek to address this and other needs.

Overview

In an effort to address at least some of the shortcomings associated with current anti-tumor strategies involving single immunotherapeutic agents, such as for example, high systemic exposure and related toxicities and/or sub-optimal oncolytic effects, provided herein is a method comprising administering to a subject having cancer, an innate immunity activating amount of a TLR agonist and an IL-2Rβ-activating amount of a long acting IL-2Rβ-biased agonist. The present disclosure is based, at least in part, on the discovery of a surprisingly advantageous therapeutic combination comprising a TLR agonist, preferably a multi-arm polymer conjugate of a TLR 7/8 agonist as provided herein, and a long-acting IL-2R agonist, and more specifically, an IL-2Rβ-biased agonist.

IL-2 stimulates immune cell proliferation and activation through a receptor-signaling complex containing alpha (IL2Rα, CD25), beta (IL2Rβ, CD122) and common gamma chain receptors ($γ_c$, CD132). At high doses, IL2 binds to heterodimeric IL2Rβγ receptor leading to desired expansion of tumor killing CD8+ memory effector T (CD8 T) cells. However, IL2 also binds to its heterotrimeric receptor IL2Rαβγ with greater affinity, which expands immunosuppressive CD4+, CD25+ regulatory T cells (Tregs), which may lead to an undesirable effect for cancer immunotherapy. Thus, provided herein is a treatment modality that combines administration of an IL-2Rαβ-biased agonist, and in particular, a long acting IL-2Rαβ-biased agonist and a TLR agonist. Without being bound by theory, the Applicants have discovered that by utilizing a long-acting IL-2 compound in which a region that interacts with the IL2Rα subunit responsible for activating immunosuppressive Tregs is masked (i.e., its activity suppressed or dampened), i.e., a long acting IL-2Rαβ-biased agonist, when selectively combined with a TLR agonist having a mechanism of action of antigen-presenting cell maturation and T-cell priming, superior therapeutic efficacy can be achieved, as will become apparent from the instant disclosure and supporting examples. Indeed, in a representative example, the foregoing combination produced an astounding abscopal effect such that efficacy was observed in all tumors, both tumors in which a TLR agonist was directly administered (primary tumor) and those in which a TLR agonist was not directly administered (secondary tumor).

The treatment method provided herein comprises administering a TLR agonist, i.e., for stimulating an innate immune response. Administration of the TLR agonist is effective to, for example, activate innate immunity, myeloid cell response and increase tumor antigen presentation. Generally, the TLR agonist can create a tumor-suppressing microenvironment in the tumor by mimicking local infection.

Various TLR agonists can be administered in accordance with the methods described herein, and the disclosure is not limited in this regard. It is the Applicant's view that successful outcomes can be achieved via the IL-2 pathway (i.e., via co-administration of a TLR agonist and a long acting IL-2Rαβ-biased agonist) to stimulate the desired T-cell responses due to the complementary natures and mechanisms of action of the TLR agonist and the long acting IL-2Rαβ-biased agonist. Illustrative TLR agonists include, but are not limited to, for example, TLR 7 or TLR 8 agonists. Particular preferred TLR agonists are multi-arm polymer conjugates of a TLR 7/8 agonist as previously described.

In one or more embodiments, the TLR agonist is a 20,000 dalton 4-arm-pentaerythritolyl-based polyethylene glycol conjugate having a TLR agonist molecule such as resiquimod covalently linked, either stably or releasably, at the terminus of each of its four polymer arms.

In certain embodiments, the long-acting TLR agonist is a 4-arm-pentaerythritolyl-based polyethylene glycol conjugate having R848 releasably covalently linked at the terminus of each of its four polymer arms and having the following structure.

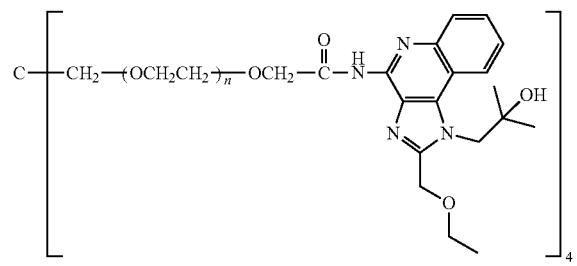

The foregoing TLR agonist multi-arm polymer conjugate is referred to herein as "4-arm-PEG-CM-N-R848", where N-indicates linkage to an amino group of the TLR agonist molecule, R848; its preparation is described in Example 3.

In certain embodiments, the TLR agonist is any one of Compounds 1-10 or 12-16, or a pharmaceutically acceptable salt form thereof.

In certain embodiments, the TLR agonist is Compound 11 having the structure shown below, where n is any suitable number of repeat units as described herein:

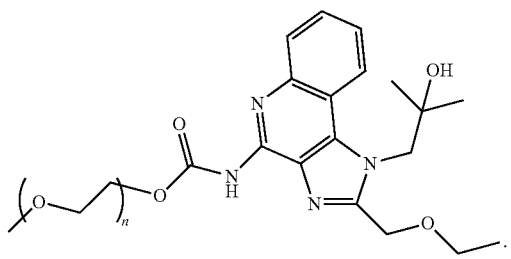

In yet other preferred embodiments, the TLR agonist compound is Compound 6, having the structure shown below, where n is any suitable number of repeat units as described herein:

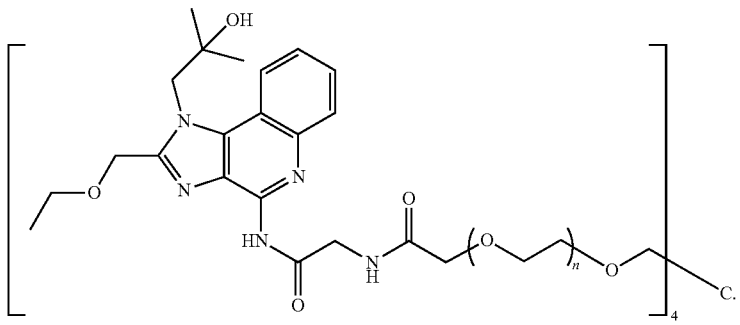

The TLR agonist may be administered by any suitable administration route, for example, intradermal, intravenous, subcutaneous, intranodel, intralymphatic, intratumoral, and the like. In one or more particular embodiments of the method, the TLR agonist is administered directly to the tumor, for example, by injection, in an amount effective to activate innate immunity in a subject.

Long Acting, IL-2Rβ-Biased Agonist

The methods, formulations, kits and the like described herein involve the administration of a long acting, IL-2Rβ-biased agonist. In this regard, the disclosure is not limited to any particular long acting, IL-2Rβ-biased agonist so long as the agonist exhibits an in vitro binding affinity for IL-2Rβ that is at least 5 times greater (more preferably at least 10 times greater) than the binding affinity for IL-2Rαβ in the same in vitro model, and has at least an effective 10-fold in vivo half-life greater than IL-2 (half-life based on the in-vivo disappearance of IL-2). By way of example, it is possible to measure binding affinities against IL-2 as a standard. In this regard, the RSLAIL-2 referenced in Example 1 herein exhibits about a 60-fold decrease in affinity to IL-2Rαβ relative to IL-2, but only about a 5-fold decrease in affinity IL-2Rβ relative to IL-2.

Non-limiting examples of long acting, IL-2Rβ-biased agonists are described in International Patent Publication Nos. WO 2012/065086 and in WO 2015/125159. An exemplary long acting, IL-2Rβ-biased agonist is RSLAIL-2 referenced in Example 19 in the present application, where the releasable PEG is based upon a 2,7,9-substituted fluorene as shown below, with poly(ethylene glycol) chains extending from the 2- and 7-positions on the fluorene ring via amide linkages (fluorene-C(O)—NH~), and releasable covalent attachment to IL-2 via attachment to a carbamate nitrogen atom attached via a methylene group (—CH$_2$—) to the 9-position of the fluorene ring. In this regard, RSLAIL-2 is a composition comprising compounds encompassed by the following formula:

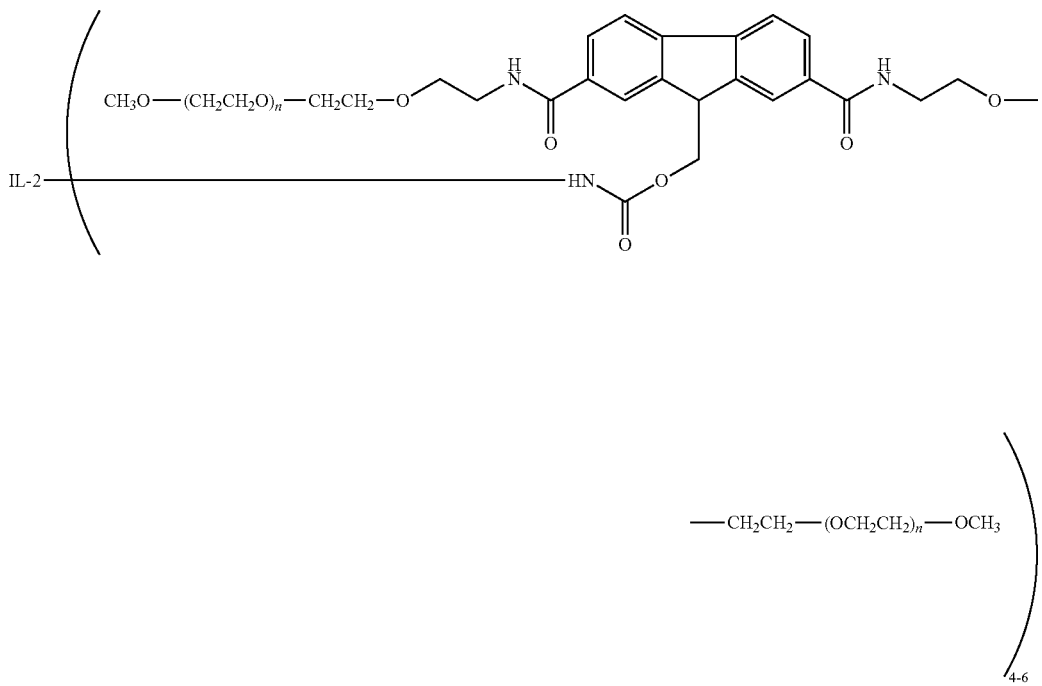

wherein IL-2 is a residue of IL-2, and pharmaceutically acceptable salts thereof, where "n" is an integer from about 3 to about 4000. In one or more embodiments, the composition contains no more than 10% (based on a molar amount), and preferably no more than 5% (based on a molar amount), of compounds encompassed by the following formula

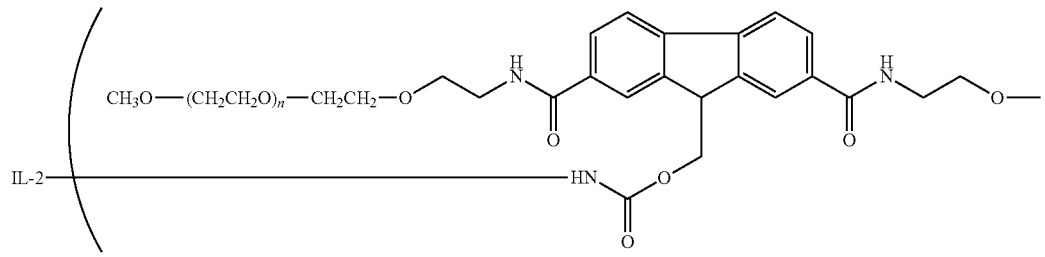

wherein IL-2 is a residue of IL-2, (n) (referring to the number of polyethylene glycol moieties attached to IL-2) is an integer selected from the group consisting of 1, 2, 3, 7 and >7, and pharmaceutically acceptable salts thereof. In some embodiments, RSLAIL-2 possesses on average about six polyethylene glycol moieties attached to IL-2. In some further embodiments, RSLAIL-2 is generally considered to be an inactive prodrug, i.e., inactive upon administration, and by virtue of slow release of the polyethylene glycol moieties in vivo, providing active conjugated forms of interleukin-2, effective to achieve sustained concentrations at the tumor site.

Additional exemplary compositions of RSLAIL-2 comprise compounds in accordance with the above formula wherein the overall polymer portion of the molecule has a weight average molecular weight in a range of from about 250 Daltons to about 90,000 Daltons. Additional suitable ranges include weight average molecular weights in a range selected from about 1,000 Daltons to about 60,000 Daltons, in a range of from about 5,000 Daltons to about 60,000 Daltons, in a range of about 10,000 Daltons to about 55,000 Daltons, in a range of from about 15,000 Daltons to about 50,000 Daltons, and in a range of from about 20,000 Daltons to about 50,000 Daltons.

Additional illustrative weight-average molecular weights for the polyethylene glycol polymer portion include about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. In some embodiments, the weight-average molecular weight of the polyethylene glycol polymer is about 20,000 daltons.

As described above, the long-acting, IL-2Rβ-biased agonist may be in the form of a pharmaceutically-acceptable salt (as is the case for the TLR agonist). Typically, such salts are formed by reaction with a pharmaceutically-acceptable acid or an acid equivalent. The term "pharmaceutically-acceptable salt" in this respect, will generally refer to the relatively non-toxic, inorganic and organic acid addition salts. These salts can be prepared in situ in the administration vehicle or the dosage form manufacturing process, or by separately reacting a long-acting interleukin-2 as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, oxylate, mesylate, glucoheptonate, lactobionate, and laurylsulphonate salts and the like. (See, for example, Berge et al. (1977) "Pharmaceutical Salts", J. Pharm. Sci. 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In reference to the foregoing IL-2Rβ-biased agonist, the term "IL-2" as used herein, refers to a moiety having human IL-2 activity. The term, 'residue', in the context of residue of IL-2, means the portion of the IL-2 molecule that remains following covalent attachment to a polymer such as a polyethylene glycol, at one or more covalent attachment sites, as shown in the formula above. It will be understood that when the unmodified IL-2 is attached to a polymer such as polyethylene glycol, the IL-2 is slightly altered due to the presence of one or more covalent bonds associated with linkage to the polymer(s). This slightly altered form of the IL-2 attached to another molecule may, in some instances, be referred to a "residue" of the IL-2.

For example, proteins having an amino acid sequence corresponding to any one of SEQ ID NOs: 1 through 4 described in International Patent Publication No. WO 2012/065086 are exemplary IL-2 proteins, as are any proteins or polypeptides substantially homologous thereto. The term substantially homologous means that a particular subject sequence, for example, a mutant sequence, varies from a reference sequence by one or more substitutions, deletions, or additions, the net effect of which does not result in an adverse functional dissimilarity between the reference and subject sequences. For the purposes herein, sequences having greater than 95 percent homology, equivalent biological activity (although not necessarily equivalent strength of biological activity), and equivalent expression characteristics are considered substantially homologous. For purposes of determining homology, truncation of the mature sequence should be disregarded. As used herein, the term "IL-2" includes such proteins modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties. In addition, the IL-2 can be derived from human sources, animal sources, and plant sources. One exemplary IL-2 is recombinant IL-2 referred to as aldesleukin.

Conventional approaches, such as those involving radiolabeling a compound, administering it in vivo, and determining its clearance, can be used to determine whether a compound proposed to be a long-acting IL-2Rβ biased agonist is "long-acting". For the purposes herein, the long acting nature of an IL-2Rβ biased agonist is typically determined using flow cytometry to measure STAT5 phosphorylation in lymphocytes at various time points after administration of the agonist to be evaluated in mice. As a reference, the signal is lost by around 24 hours with IL-2, but is sustained for a period greater than that for a long-acting IL-2Rβ-biased agonist. As an illustration, the signal is sustained over several days for the RSLAIL-2 compositions.

Considering now the IL-2Rβ bias of a long-acting agonist as described herein, Example 20 provides both in-vitro and in-vivo data related to receptor bias for exemplary compositions of RSLAIL-2. As described in Example 20, in a murine melanoma tumor model, the ratio of CD8/regulatory T cells for RSLAIL-2 when compared to IL-2 supports preferential activation of the IL-2 receptor beta over IL2 receptor alpha. Exemplary long-acting IL-2Rβ biased agonists such as RSLAIL-2 are, for example, effective to preferentially activate and expand effector CD8+ T- and NK-cells over Tregs.

Moreover, representative long-acting IL-2Rβ-biased agonists such as RSLAIL-2 provide increased tumor exposure, and preferably significantly enhanced tumor exposure relative to IL-2, for example, at least a 50-fold increased exposure, or at least a 100-fold increased exposure, or at least a 200-fold increased exposure, or at least a 300-fold increased exposure, or at least a 400-fold increased exposure, or at least a 500-fold increased exposure when normalized for equivalents of IL-2.

Methods, Compositions, and Kits Related to the Foregoing

Based upon at least one or more of the features of a long-acting IL-2Rβ-biased agonist as described herein, provided herein are methods effective to selectively optimize TLR activity in a tumor by administration, e.g., localized administration of a multi-arm polymer conjugate of a TLR agonist with minimal systemic exposure, to thereby expand T-cell responses in cancer patients by systemically administering a long-acting IL-2 compound in which a region that interacts with the IL2Rα subunit responsible for activating immunosuppressive Tregs is masked, to thereby achieve superior therapeutic efficacy for the combination.

In accordance with the methods, compositions, and kits described herein, the long-acting, IL-2Rβ-biased agonist is provided in an IL-2Rβ-activating amount. One of ordinary skill in the art can determine how much of a given long-acting, IL-2Rβ-biased agonist is sufficient to provide clinically relevant agonistic activity at IL-2Rβ. For example, one of ordinary skill in the art can refer to the literature and/or administer a series of increasing amounts of the long-acting, IL-2Rβ-biased agonist and determine which amount or amounts provide clinically effective agonistic activity of IL-2Rβ. Alternatively, an activating amount of the long acting IL-2Rβ-biased agonist can be determined using the in vivo STAT5 phosphorylation assay described above (determined in vivo following administration) where an amount sufficient to induce STAT5 phosphorylation in greater than 10% of NK cells at peak is considered to be an activating amount.

In one or more instances, however, the IL-2Rβ-activating amount is an amount encompassed by one or more of the following ranges expressed in amount of protein: from about 0.01 to 100 mg/kg; from about 0.01 mg/kg to about 75 mg/kg; from about 0.02 mg/kg to about 60 mg/kg; from about 0.03 mg/kg to about 50 mg/kg; from about 0.05 mg/kg to about 40 mg/kg; from about 0.05 mg/kg to about 30 mg/kg; from about 0.05 mg/kg to about 25 mg/kg; from about 0.05 mg/kg to about 15 mg/kg; from about 0.05 mg/kg to about 10 mg/kg; from about 0.05 mg/kg to about 5 mg/kg; from about 0.05 mg/kg to about 1 mg/kg. In some embodiments, the long acting IL-2Rβ-biased agonist is administered at a dose that is less than or equal to 0.7 mg/kg. Particular illustrative dosing ranges include for example, from about 0.1 mg/kg to about 10 mg/kg, or from about 0.2 mg/kg to about 7 mg/kg or from about 0.2 mg/kg to less than about 0.7 mg/kg.

For confirmation, with respect to the long-acting, IL-2Rβ-biased agonist, the amount and extent of the activation can vary widely and still be effective when coupled with administration of a TLR agonist. That is to say, an amount of a long-acting, IL-2Rβ-biased agonist that exhibits only minimal agonist activity at IL-2Rβ for a sufficiently extended period of time can still be a long-acting, IL-2Rβ-biased agonist so long as when administered with a TLR agonist, the methods, compositions, and kits described herein enable a clinically meaningful response. In some instances, due to (for example) synergistic interactions and responses, only minimal agonist activity of IL-2Rβ may be required when accompanied by administration of a TLR agonist (e.g., a long-acting TLR agonist).

The treatment methods described herein can continue for as long as the clinician overseeing the patient's care deems the treatment method to be effective. Non-limiting parameters that indicate the treatment method is effective include any one or more of the following: tumor shrinkage (in terms of weight and/or volume); a decrease in the number of individual tumor colonies; tumor elimination; and progression-free survival. Change in tumor size may be determined by any suitable method such as imaging. Various diagnostic imaging modalities can be employed, such as computed tomography (CT scan), dual energy CDT, positron emission tomography and MRI.

The actual doses of the TLR agonist and the long-acting, IL-2Rβ-biased agonist, as well as the dosing regimen associated with the methods, compositions, and kits described herein will vary depending upon the age, weight, and general condition of the subject as well as the type and progression of the cancer being treated, the judgment of the health care professional, and the particular TLR agonist and long-acting, IL-2Rβ-biased agonist to be administered.

With regard to the frequency and schedule of administering the TLR agonist and the long acting, IL-2Rβ-biased agonist, one of ordinary skill in the art will be able to determine an appropriate frequency. For example, in a treatment cycle, a clinician can decide to administer the TLR agonist, either as a single dose or in a series of doses, e.g., over the course of several days or weeks). In some treatment regimens, the TLR agonist is administered as a single dose at the commencement of treatment. The long acting, IL-2Rβ-biased agonist is administered, either concurrently with the TLR agonist, or prior to administration of the TLR agonist, or following administration of the TLR agonist. In a preferred treatment modality, the TLR agonist is administered prior to the long acting, IL-2Rβ-biased agonist. For example, when the TLR agonist is a multi-arm polymer conjugate of a TLR 7/8 agonist, the TLR agonist is administered intratumorally, while the IL-2Rβ-biased agonist is administered systemically, e.g., by injection. For example, in some treatment modalities, the long acting, IL-2Rβ-biased agonist is administered within 14 days of TLR agonist administration (e.g., on any one of days 1, 2, 3, 4, 5, 6, 7, 8, 9, 10, 11, 12, 13 or 14), where day 0 indicates commencement of treatment. In some treatment regimens, the long acting, IL-2Rβ-biased agonist is administered within 7 days of administration of the TLR agonist, e.g., on any one of days 1, 2, 3, 4, 5, 6 or 7; or is administered within 4 days of administration of the TLR agonist, or is administered within 2 days of administration of the TLR agonist.

Based upon the long acting nature of the IL-2Rβ-biased agonist, such compound is typically administered relatively infrequently (e.g., once every three weeks, once every two weeks, once every 8-10 days, once every week, etc.).

Exemplary lengths of time associated with the course of therapy include about one week; about two weeks; about three weeks; about four weeks; about five weeks; about six weeks; about seven weeks; about eight weeks; about nine weeks; about ten weeks; about eleven weeks; about twelve weeks; about thirteen weeks; about fourteen weeks; about fifteen weeks; about sixteen weeks; about seventeen weeks; about eighteen weeks; about nineteen weeks; about twenty weeks; about twenty-one weeks; about twenty-two weeks; about twenty-three weeks; about twenty four weeks; about seven months; about eight months; about nine months; about ten months; about eleven months; about twelve months; about thirteen months; about fourteen months; about fifteen months; about sixteen months; about seventeen months; about eighteen months; about nineteen months; about twenty months; about twenty one months; about twenty-two months; about twenty-three months; about twenty-four months; about thirty months; about three years; about four years and about five years.

The treatment methods described herein are typically continued for as long as the clinician overseeing the patient's care deems the treatment method to be effective, i.e., that the patient is responding to treatment. Non-limiting parameters that indicate the treatment method is effective may include one or more of the following: tumor shrinkage (in terms of weight and/or volume and/or visual appearance); a decrease in the number of individual tumor colonies; tumor elimination; progression-free survival; appropriate response by a suitable tumor marker (if applicable), increased number of NK (natural killer) cells, increased number of T cells, increased number of memory T cells, increased number of central memory T cells, reduced numbers of regulatory T cells such as CD4+ Tregs, CD25+ Tregs, and FoxP3+ Tregs.

The methods provided herein are useful for (among other things) treating a patient having cancer. For example, patients may be responsive to treatment with the TLR agonist alone, to treatment with the long acting, IL-2Rβ-biased agonist alone, as well as to the combination with of the TLR agonist and the long acting, IL-2Rβ-biased agonist—but are more responsive to the combination. By way of further example, patients may be non-responsive to either the TLR agonist or the long acting, IL-2Rβ-biased agonist, but are responsive to the combination. By way of still further example, patients may be non-responsive to both the TLR agonist and the long acting, IL-2Rβ-biased agonist when administered alone, but are responsive to the combination.

Administration, e.g., of the TLR agonist and/or the long acting, IL-2Rβ-biased agonist is typically via injection. Other modes of administration are also contemplated, such as pulmonary, nasal, buccal, rectal, sublingual and transdermal. As used herein, the term "parenteral" includes subcutaneous, intravenous, intra-arterial, intratumoral, intralymphatic, intraperitoneal, intracardiac, intrathecal, and intramuscular injection, as well as infusion injections. As described previously, the TLR agonist and the long acting, IL-2Rβ-biased agonist can be administered separately. Alternatively, if administration of the TLR agonist and the long acting, IL-2Rβ-biased agonist, is desired to be simultaneous, either as an initial dose or throughout the course of treatment or at various stages of the dosing regimen—and the TLR agonist and the long acting, IL-2Rβ-biased agonist are compatible together and in a given formulation—then the simultaneous administration can be achieved via administration of single dosage form/formulation (e.g., intravenous administration of an intravenous formulation that contains both immunological components). One of ordinary skill in the art can determine through routing testing whether two such components are compatible together and in a given formulation.

The therapeutic combination described herein, i.e., the long acting IL-2Rβ-biased agonist and TLR agonist, may be provided in the form of a kit. As described above, the components may be comprised in a single composition, optionally accompanied by one or more pharmaceutically acceptable excipients, or may be provided in separate containers, where the kit typically includes instructions for use. The kit components, e.g., compositions comprising the TLR agonist and the long acting IL-2Rβ-biased agonist, may be in either liquid or in solid form. In certain embodiments, both the TLR agonist and the long acting IL-2Rβ-biased agonist are in solid form. Representative solid forms are those that are solid dry forms, e.g., containing less than about 5 percent by weight water, or preferably less than 2 percent by weight water. The solid forms are generally suitable for reconstitution in an aqueous diluent.

The presently described methods, kits and related compositions can be used to treat a patient suffering from any condition that can be remedied or prevented by the methods provided herein, such as cancer. Exemplary conditions are cancers, such as, for example, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, brain cancer, breast cancer, ovarian cancer, prostate cancer, squamous cell cancer, basal cell cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, Hodgkin lymphoma, non-Hodgkin lymphoma, testicular cancer, lung cancer, small cell lung cancer, brain cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma, multiple myeloma, neuroblastoma, retinoblastoma and leukemias. In some particular embodiments, the cancer to be treated is a solid cancer, such as for example, breast cancer, ovarian cancer, colon cancer, prostate cancer, bone cancer, colorectal cancer, gastric cancer, lymphoma, malignant melanoma, liver cancer, small cell lung cancer, non-small cell lung cancer, pancreatic cancer, thyroid cancers, kidney cancer, cancer of the bile duct, brain cancer, cervical cancer, maxillary sinus cancer, bladder cancer, esophageal cancer, Hodgkin's disease and adrenocortical cancer.

The present methods, kits and compositions are useful for enhancing the therapeutic effectiveness of administration of either the TLR agonist or the long-acting IL-2Rβ-biased agonist as a single agent. An enhanced response may be evaluated at any suitable time point during treatment, after a single round of treatment, after 2-3 cycles of treatment, etc., and by any of a number of suitable methods, including shrinkage of a tumor (partial response), i.e., an evaluation of tumor size or volume, disappearance of a tumor, a reduction in disease progression (cancer has not progressed), and analysis of one or more tumor test markers if appropriate. Particularly effective treatments will prolong survival, when evaluated at 50% maximum tumor growth), by at least 5 days, or at least 10 days, or at least 12 days, or at least 15 days, or by at least 20 days, or by at least 30 days or more.

The methods, kits, compositions and the like provided herein are also useful for reducing tumor growth or size (or volume) in a subject undergoing treatment. For example, in some embodiments, one or more cycles of treatment is effective to reduce tumor size by about 25%, or by about 30%, or by about 40%, or by about 50%, or even by about 60%, or by about 70% or more, for example by about 90% or more, when compared to the size of the tumor prior to treatment.

In turning to the supporting examples, various murine tumor models were assessed for combination treatment efficacy with an exemplary multi-arm polymer conjugate of a TLR 7/8 agonist, resiquimod, 4-arm-PEG20k-CM-Gly-N-R848 (Compound 6), and an illustrative long-acting IL-2Rβ-biased agonist, RSLAIL-2, as described in detail in Examples 23-30. The tumor models included a CT26 colon carcinoma tumor model, a WEHI-164 fibrosarcoma tumor model, a JC mammary adenocarcinoma tumor model, a 4T1 mammary carcinoma tumor model, a MC38 colon carcinoma tumor model, an EMT6 mammary carcinoma tumor model, an RM-1 prostate carcinoma tumor model, and an H22 hepatocellular carcinoma tumor model, respectively. Combination treatment showed efficacy in all tested tumor models, with efficacy ranging from significant tumor growth inhibition to up to 100% complete responses in multiple models.

Results from the CT26 colon carcinoma tumor model indicate that very low amounts of intratumorally delivered TLR agonist, in combination with RSLAIL-2 treatment, significantly inhibits tumor growth at the treatment site as well as at an untreated abscopal tumor site, i.e., a site in which the TLR agonist compound was not directly administered.

In the WEHI-164 fibrosarcoma tumor model, double agent treatment with RSLAIL-2+4-arm-PEG20k-CM-Gly-N-R848 resulted in survival of 90% of the animals by the end of the study at day 52 after commencement of dosing. Strikingly, 80% of all animals in the RSLAIL-2+4-arm-PEG20k-CM-Gly-N-R848 treatment group had complete responses, meaning no measurable tumors were observed by the end of the study, where in contrast. The vehicle group had no surviving animals. All animals were removed from study due to reaching limiting tumor volume between days 17 and 31 after treatment start.

Similarly, in a JC mammary adenocarcinoma tumor model, dual agent treatment (i.e., combination therapy) with RSLAIL-2 and 4-arm-PEG20k-CM-Gly-N-R848 (Compound 6) resulted in survival of 90% of the animals by day 43, while no surviving animals were remaining in the vehicle group by day 43. RSLAIL-2+4-arm-PEG20k-CM-Gly-N-R848 combination treatment led to 20% of the animals surviving by the end of the study at day 113 after commencement of dosing. Strikingly, 10% of animals in the RSLAIL-2+4-arm-PEG20k-CM-Gly-N-R848 treatment group had complete responses, meaning that no measurable tumors were observed by the end of the study. In contrast, the vehicle group had no surviving animals. In fact, all animals were removed from study due to reaching limiting tumor volume between days 26 and 36 after treatment start.

In a similar fashion, in a 4T1 mammary carcinoma tumor model, dual immunotherapeutic agent treatment with RSLAIL-2+4-arm-PEG20k-CM-Gly-N-R848 resulted in survival of 30% of the animals by the end of the study at day 25 after commencement of dosing. The combination treatment with RSLAIL-2+4-arm-PEG20k-CM-Gly-N-R848 showed significant improvement over the vehicle treatment by slowing tumor growth in treated animals. In contrast, the vehicle group had no surviving animals by end of study at day 25. All animals were removed from study due to reaching limiting tumor volume between days 16 and 18 after treatment start.

As provided in Example 27, in an MC38 colon carcinoma tumor model, dual immunotherapeutic agent treatment with RSLAIL-2+4-arm-PEG20k-CM-Gly-N-R848 resulted in survival of 50% of the animals by the end of the study at day 70 following commencement of dosing. Significantly, all surviving animals in the RSLAIL-2+4-arm-PEG20k-CM-Gly-N-R848 treatment group had complete responses, meaning no measurable tumors were observed by the end of the study. In striking contrast, the vehicle group had no surviving animals.

In a subcutaneous EMT6 mammary carcinoma tumor model as described in Example 28, single agent treatment with RSLAIL-2 or 4-arm-PEG20k-CM-Gly-N-R848 resulted in partial control of tumor growth but no surviving animals by the end of the study at day 55 after commencement of dosing. In striking contrast, dual agent treatment with RSLAIL-2+4-arm-PEG20k-CM-Gly-N-R848 resulted in survival of 100% of the animals by the end of the study at day 55 after commencement of dosing. In the treatment regimen, tumor-forming cells were implanted subcutaneously with a tumor in each flank, and 4-arm-PEG20k-CM-Gly-N-R848 was dosed intra- or peritumorally (i.e., directly) to one of the two tumors (primary tumor), where the secondary contralateral side tumor was not treated directly with the TLR agonist, 4-arm-PEG20k-CM-Gly-N-R848. RSLAIL-2 was dosed systemically by intravenous injection. All animals in the surviving group had complete responses, with both tumors (primary and secondary) eliminated. That is to say, unexpectedly, the combination treatment with RSLAIL-2+4-arm-PEG20k-CM-Gly-N-R848 provided not only a significant improvement over the equivalent dose RSLAIL-2 or 4-arm-PEG20k-CM-Gly-N-R848 monoimmunotherapeutic treatment modalities, but also resulted in the complete eradication of both the primary tumor (injected with the TLR agonist) and the secondary tumor (no direct injection of TLR agonist, removed from site of primary tumor). The vehicle group had no surviving animals.

As provided in Example 29, studies were conducted to evaluate and compare the antitumor response of a combination of an illustrative long acting IL-2Rβ-biased agonist, RSLAIL-2, and an exemplary long-acting TLR agonist, 4-arm-PEG20k-CM-Gly-N-R848, in a RM-1 prostate carcinoma tumor model when compared to vehicle treatment. Combination therapy agent with RSLAIL-2+4-arm-PEG20k-CM-Gly-N-R848 resulted in significantly reduced tumor growth compared to vehicle treatment resulting in survival of 80% of the animals by 20 days after treatment commencement and 10% of animals by the end of study on day 36 in the RSLAIL-2+4-arm-PEG20k-CM-Gly-N-R848 treatment group. In contrast, the vehicle group had no surviving animals by day 20 after treatment start.

In yet a further illustrative in vivo study as described in Examples 30, studies were conducted to evaluate and compare the antitumor response of a combination of an illustrative long acting IL-2Rβ-biased agonist, RSLAIL-2, and an exemplary long-acting TLR agonist, 4-arm-PEG20k-CM-Gly-N-N-R848, in a H22 hepatocellular carcinoma tumor model when compared to vehicle treatment. Dual agent treatment with RSLAIL-2+4-arm-PEG20k-CM-Gly-N-R848 resulted in survival of 50% of the animals by the end of the study at day 105 after commencement of dosing. Significantly, 40% of animals in the RSLAIL-2+4-arm-PEG20k-CM-Gly-N-R848 treatment group had complete responses, meaning no measurable tumors were observed by the end of the study. In contrast, the vehicle group had no surviving animals, demonstrating, as in each of these illustrative examples, the exceptional results provided by the disclosed combination therapy.

EXAMPLES

All non-PEG chemical reagents referred to in the examples are commercially available unless otherwise indicated. The preparation of water-soluble polymer reagents can be prepared using art-known techniques described in the literature unless otherwise indicated, or can be obtained from commercially-available sources.

Materials 4-arm-PEG20kD-SCM (NETS-ester) and 4-arm-PEG40kD-SCM (NHS-ester) can be synthesized according to Example 3 of PCT Publication No. WO 2010/019233 A1.

4-arm-PEG20kD-BA (butanoic acid) can be synthesized according to Example 1 of PCT Publication No. WO 2010/019233 A1.

mPEG5kD-SC is available from NOF America Corporation, Irvine, Calif., USA.

4-arm-PEG20kD-SC is available from Biochempeg Scientific Inc., Watertown, Mass., USA.

4-arm-PEG20kD-NCO is available from JenKem Technology, Plano, Tex., USA.

4-arm-PEG20kD-amine is available from Laysan Bio, Arab, Ala., USA.

Chemical structures according to each of the foregoing is provided below.

Recombinant human IL-2 having an amino acid sequence identical to that of aldesleukin was cloned and expressed and used to prepare the exemplary long acting IL-2Rαβ-biased agonist referred to herein as RSLAIL-2.

RSLAIL-2 refers to a composition obtainable upon following the procedures of Example 1 in PCT Int. Pat. Appl. Pub. No. WO 2015/125159, and generically refers to a composition comprising multiPEGylated forms of IL-2, wherein attachment to the PEG moieties comprised in the multi-PEGylated conjugates is releasable following administration to a subject.

Instruments $^1$H NMR (nuclear magnetic resonance) data was generated on a 500 mHz Bruker NMR spectrometer.

Example 1

Synthesis of 4-arm-PEG20k-CM-N—R848 (Compound 1)

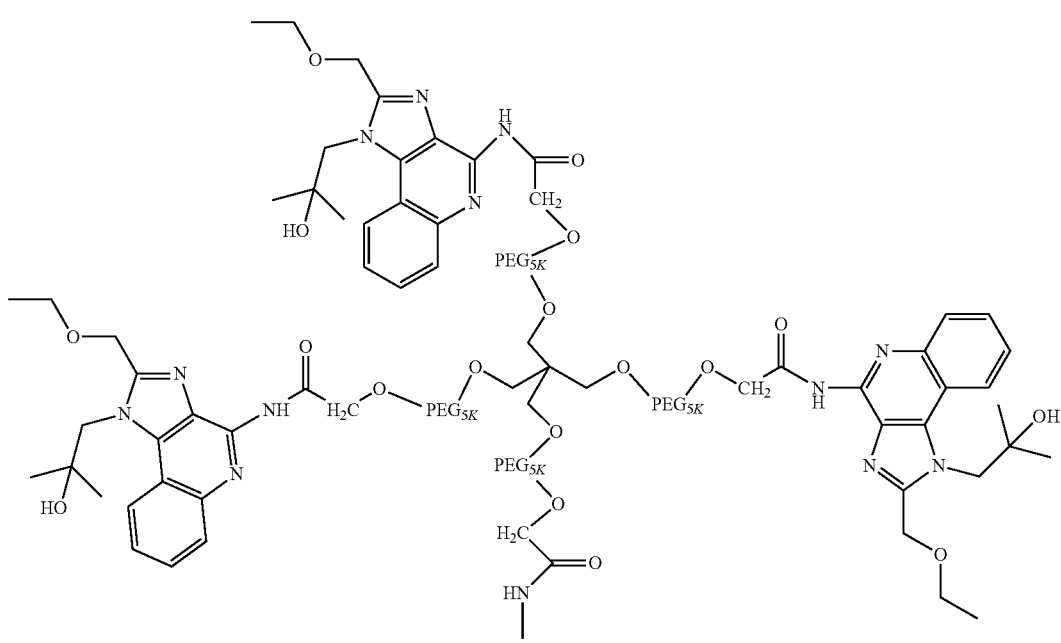

Compound 1

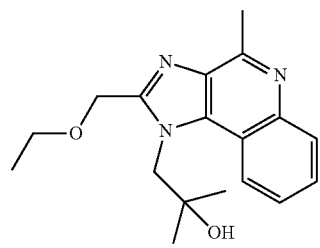
The title compound was synthesized according to the following reaction scheme.
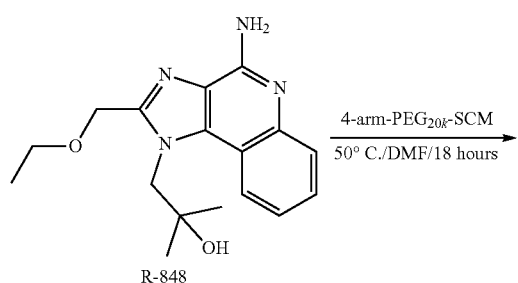
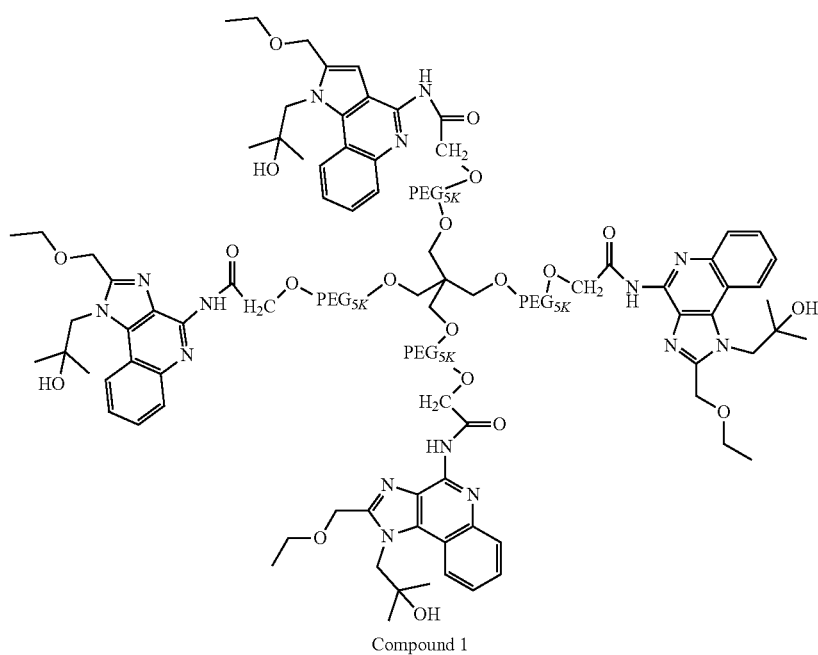
Compound 1 where 4-arm-20k-PEG-SCM has the following structure:

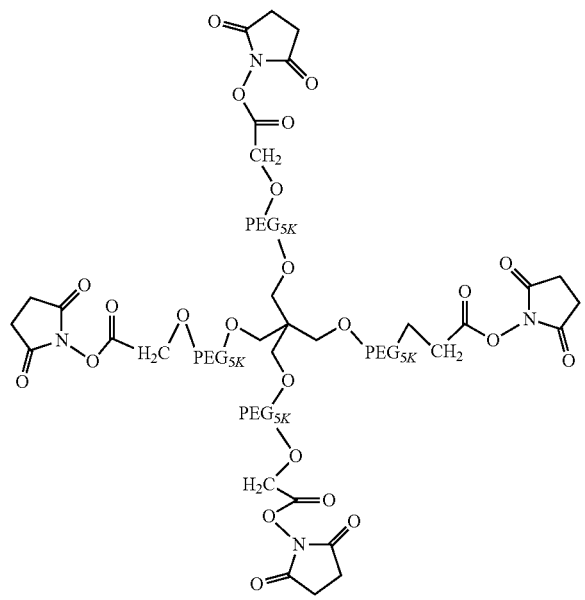

At 20° C., 4-arm-20k-PEG-SCM (5.0 g, 1.0 mmol of SCM) and R-848 (BePharm Ltd, 377 mg, 1.2 mmol) were dissolved in anhydrous N,N-dimethylformamide (25 ml). The reaction solution was stirred at 50° C. for 18 hours. The reaction solution was poured into 1 liter of ethyl ether while being stirred. The formed precipitate was collected by filtration and washed with ethyl ether (50 ml). The obtained solid was added into isopropyl alcohol (300 ml) and the suspension was heat to 60° C. to form a clear solution. The solution was cooled to room temperature while being stirred. The formed precipitate was collected by filtration and washed with ethyl ether (50 ml). The purification by precipitation in isopropyl alcohol was repeated once more and followed by drying in high vacuum overnight to give pure conjugate as a white solid (4.24 g with 5.1 wt. % R-848 loading).

$^1$H NMR (500 MHz, CDCl$_3$) δ 9.4 (broad, 3.6H), 8.22-8.14 (t, 7.1H), 7.61 (ddd, J=8.3, 7.0, 1.3 Hz, 3.6H), 7.49 (ddd, J=8.2, 7.0, 1.4 Hz, 3.6H), 4.94 (s, 7.1H), 4.80 (s, 7.1H), 3.7-3.9 (m, 1818H), 1.32 (s, 20.1H), 1.25 (t, J=7.0 Hz, 10.7H).

Example 2

Synthesis of 4-arm-PEG20k-CM-β-alanine-N-R848 (Compound 2)

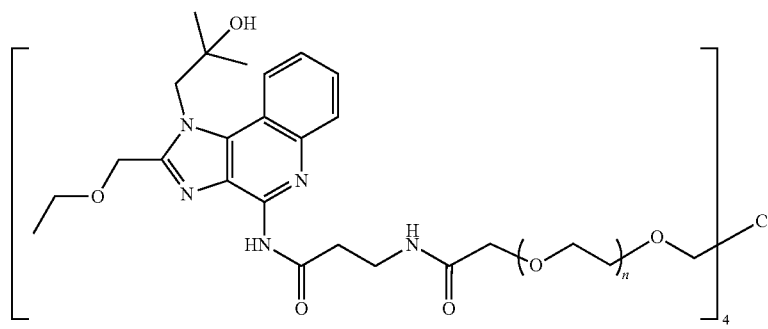

Compound 2

The title compound was synthesized according to the following reaction scheme.

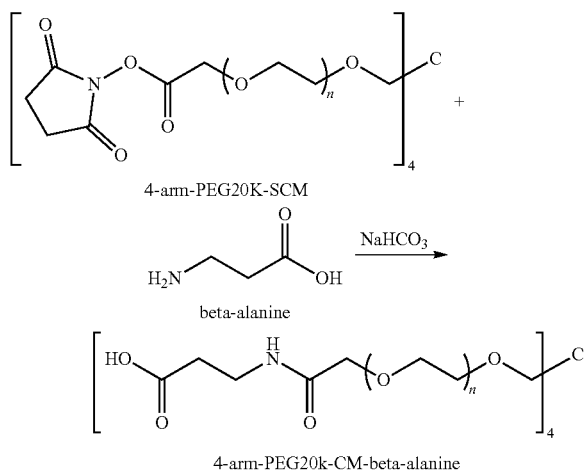

4-arm-PEG20k-CM-β-alanine:

Beta-alanine (7.100 g, 10 equiv.) and sodium bicarbonate (6.720 g, 10 equiv.) were added into deionized water (800 ml) and the mixture was stirred to form a clear solution. 4-arm-PEG20k-SCM (40.020 g, 1 equiv.) was added into the solution. The reaction solution was stirred at room temperature for 3 hours. 5N HCl was added into the solution to adjust the pH to 4.0. The solution was extracted with dichloromethane (150 ml) two times and the organic phase was combined and dried with anhydrous sodium sulfate. The solid was removed by running through a frit. The filtrate was condensed to 50 ml and then added to 500 ml ethyl ether to get precipitation. The product (35.050 g, yield 87%) as white powder was obtained by filtering and drying under high vacuum overnight.

$^1$H NMR (500 MHz, CDCl$_3$) δ 3.98 (s, 7.11H), 3.64 (t, 7.11H), 3.58-3.33 (m, 1818H), 3.27 (s, 7.90H), 2.40 (t, 7.11H).

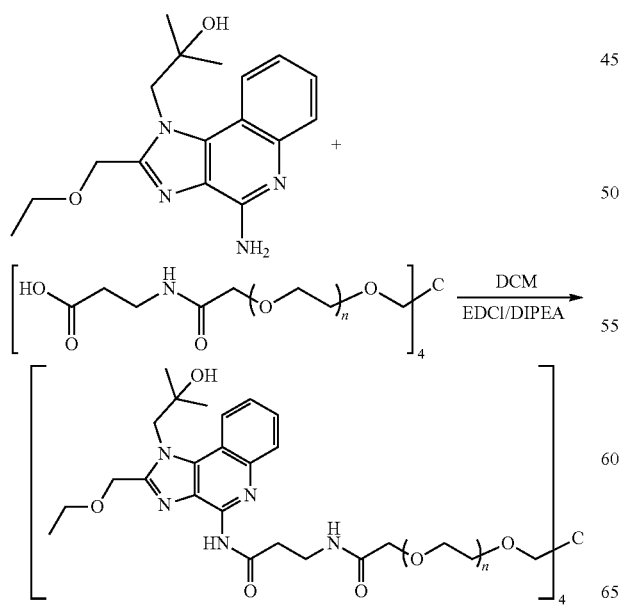

4-arm-PEG20k-CM-β-alanine-N-R848:

At 20° C., 4-arm-PEG20k-CM-β-alanine (4.012 g, 0.8 mmol of —COOH), hydroxybenzotriazole (216 mg, 1.6 mmol), N-(3-dimethylaminopropyl)-N'-ethylcarbodiimide hydrochloride (307 mg, 1.6 mmol), and N,N-diisopropylethylamine (207 mg, 1.6 mmol) were dissolved in dichloromethane (25 ml). The mixture was stirred at room temperature for 30 minutes. R848 (302 mg, 0.96 mmol) was added and the reaction solution was stirred at 20° C. for 24 hours. The reaction solution was added into 1 liter of ethyl ether while it was being stirred. The formed precipitate was collected by filtration and washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated one more time followed by drying under high vacuum overnight to give pure conjugate as white solid (3.860 g with 5.6% w/w R848 loading).

$^1$H NMR (500 MHz, CDCl$_3$) δ 8.82 (s, 3.56H), 8.17 (d, J=8.0 Hz, 4.49H), 8.07 (d, J=8.0 Hz, 4.02H), 7.49 (t, J=7.8 Hz, 4.17H), 7.49 (t, J=7.8 Hz, 7.55H), 4.93 (s, 8.39H), 4.79 (s, 9.0H), 3.99 (s, 7.60H), 3.80-3.44 (m, 1818H), 1.33 (s) and 1.26 (t, J=7.1 Hz) (in total 34.18H).

Example 3

Synthesis of 4-arm-PEG20k-BA-N-R848 (Compound 3)

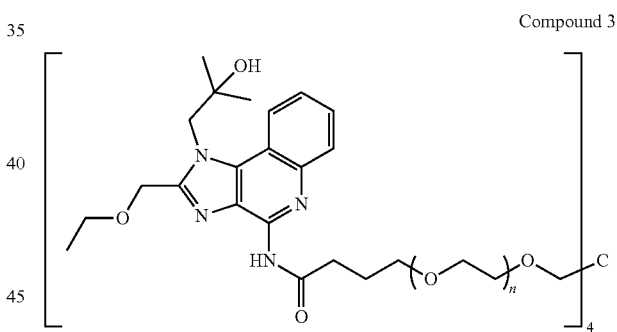

Compound 3

The title compound was synthesized according to the following reaction scheme.

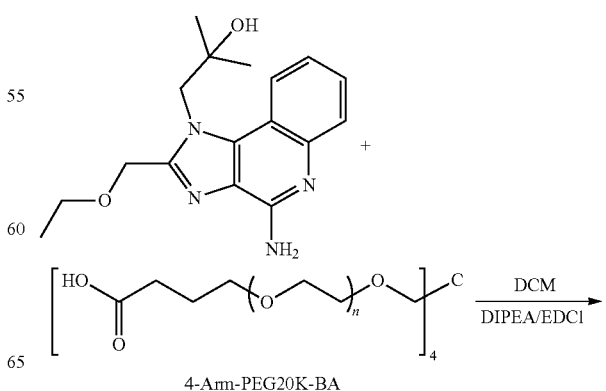

4-Arm-PEG20K-BA

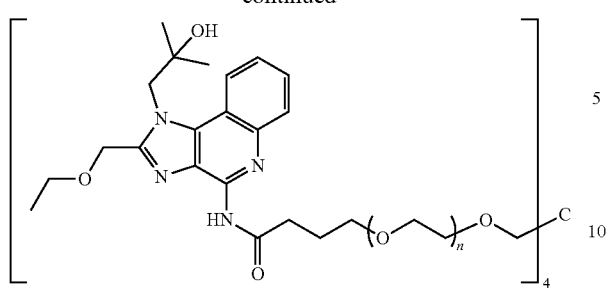

4-arm-PEG20k-BA-N-R848:

At 20° C., 4-arm-PEG20k-BA (4.020 g, 0.8 mmol of —COOH), hydroxybenzotriazole (216 mg, 1.6 mmol), N-(3-dimethylaminopropyl)-N'-ethylcarbodiimide hydrochloride (307 mg, 1.6 mmol), and N,N-diisopropylethylamine (207 mg, 1.6 mmol) were dissolved in dichloromethane (15 ml). The mixture was stirred at room temperature for 30 minutes. R848 (302 mg, 0.96 mmol) was added and the reaction solution was stirred at 20° C. for 24 hours. The reaction solution was added into 1 liter of ethyl ether while it was being stirred. The formed precipitate was collected by filtration and was washed with ethyl ether (50 ml). The obtained solid was added into isopropyl alcohol (300 ml) and the suspension was heated up to 60° C. to form clear solution. The solution was cooled to room temperature while being stirred. The formed precipitate was collected by filtration and was washed with ethyl ether (50 ml). The purification by precipitation in isopropyl alcohol was repeated one more time followed by drying under high vacuum overnight to give pure conjugate as white solid (3.805 g with 5.2% w/w R848 loading).

$^1$H NMR (500 MHz, CDCl$_3$) δ 8.16 (d, J=8.5 Hz, 3.45H), 8.07 (d, J=8.5 Hz, 3.43H), 7.59 (t, J=7.8 Hz, 3.63H), 7.47 (t, J=7.8 Hz, 3.71H), 4.91 and 4.78 (s, 15.86H), 3.77-3.40 (m, 1818H), 2.10 (t, 7.30H), 1.33 (s) and 1.26 (t, J=7.1 Hz) (in total 31.34H).

Example 4

Synthesis of 4-arm-PEG20k-CM-α-(R)-fluoro-propanamide-N-R848 (Compound 4)

Compound 4

The title compound was synthesized according to the following reaction scheme.

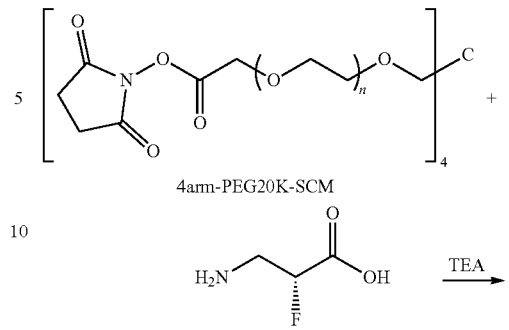

4-arm-PEG20k-CM-α-(R)-fluoro-propanoic acid:

4-arm-PEG20k-SCM (5.140 g, 1.03 mmol) was dissolved in dichloromethane (50 ml). (R)-3-amino-2-fluoro-propanoic acid (440 mg, 4.11 mmol), and triethylamine (416 mg, 4.11 mmol) were added into N,N-dimethylformamide (5 ml) to form a suspension. The suspension was added to the 4-arm-PEG20k-SCM in DCM solution. The reaction was stirred at 20° C. for 10 days and then diluted with water (200 ml). The aqueous solution was extracted with dichloromethane (3×100 ml). Organic phase was combined, dried with anhydrous magnesium sulfate and filtered. The filtrate was concentrated to 50 ml, which was added into ethyl ether (1 liter) to form precipitate. The precipitate was collected by filtration, which was dried under high vacuum to give 4.638 g white solid 4-arm-PEG20k-CM-α-(R)-fluoro-propanoic acid with 70% substitution.

$^1$H NMR (500 MHz, CDCl$_3$) δ 7.49 (s, 2.77H), 5.02 (d, J=48.5 Hz, 2.77H), 4.15 (s, 3.95H), 3.65 (br, 1818H), 3.11 (q, J=7.3 Hz, 2.92H), 1.35 (t, J=7.3 Hz, 3.95H).

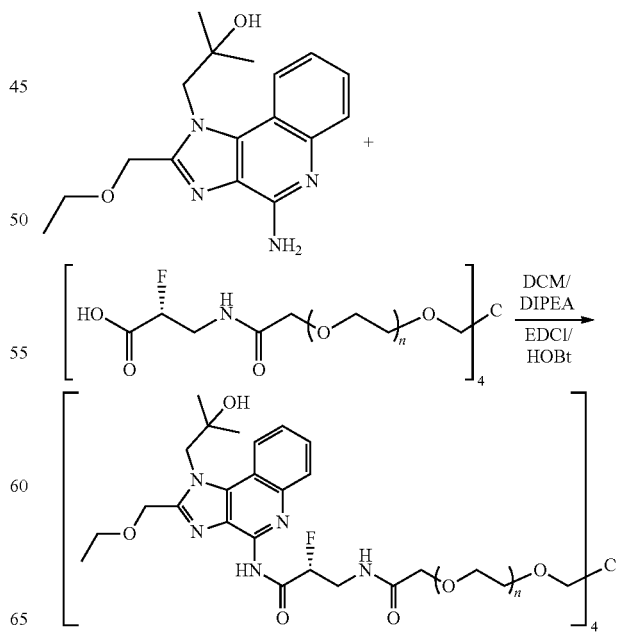

4-arm-PEG20k-CM-α-(R)-fluoro-propanamide-N-R848:

4-arm-PEG20k-CM-α-(R)-F-propanoic acid (2.004 g, 0.4 mmol of COOH), N,N-diisopropylethylamine (207 mg, 1.6 mmol), N-(3-dimethylaminopropyl)-N'-ethylcarbodiimide hydrochloride (153 mg, 0.8 mmol), and hydroxybenzotriazole (108 mg, 0.9 mmol) were dissolved in anhydrous dichloromethane (15 ml). R848 (113 mg, 0.36 mmol) was added in 30 minutes. The reaction solution was stirred at 20° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 1.602 g as white solid with 4.1 (w/w) % R848 loading.

$^1$H NMR (500 MHz, CDCl$_3$) δ 8.17 (s, 5.53H), 7.54 (d, J=57.7 Hz, 6.72H), 4.92 (s, 4.74H), 4.79 (s, 4.74H), 3.62 (br, 1818H), 1.5-1.0 (br., 30.0H).

Example 5

Synthesis of 4-arm-PEG40k-CM-N—R848 (Compound 5)

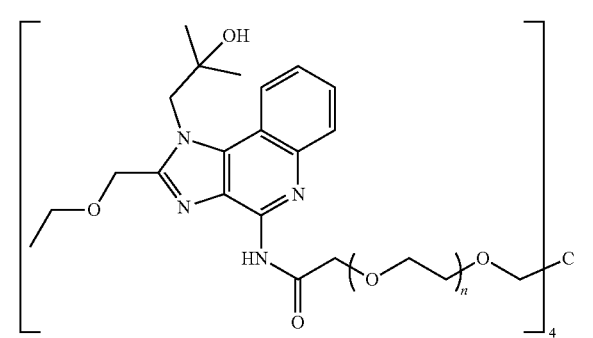

Compound 5

The title compound was synthesized according to the following reaction scheme.

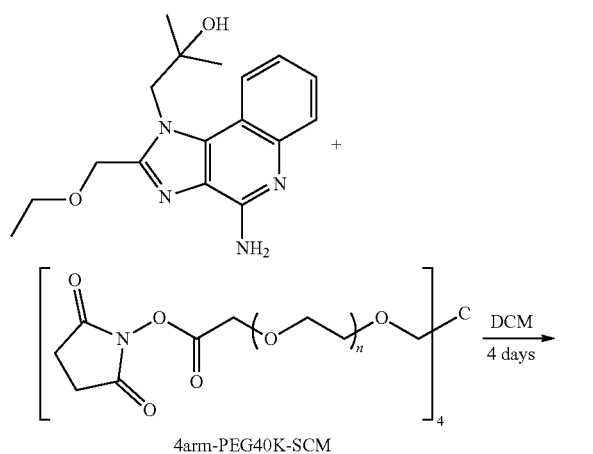

4arm-PEG40K-SCM

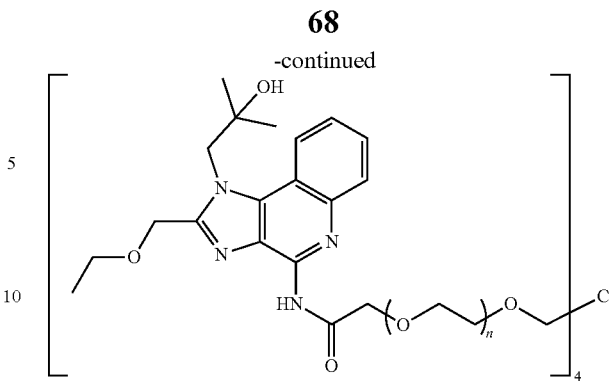

4-arm-PEG40k-CM-N—R848:

4-arm-PEG40k-SCM (4.410 g, 0.44 mmol of SCM) was dissolved in anhydrous dichloromethane (33 ml). R848 (116 mg, 0.53 mmol) was added at room temperature. The resulting mixture solution was stirred at room temperature for 4 days. The reaction mixture was concentrated to remove the solvent. The residue was recrystallized twice with isopropyl alcohol (300 ml) as mentioned above to afford 4.262 g of product as white solid. The product contained 2.0% (w/w) R848 based on NMR analysis.

$^1$H NMR (500 MHz, CDCl$_3$) δ 8.16 (m, 5.4H), 7.58 (t, 2.8H), 7.47 (t, 2.8H), 4.92-4.70 (m, 10.6H), 4.07 (s, 1.5H), 3.88-3.45 (m, 3636H), 1.23 (s) and 1.21 (t) (total 23.6H).

Example 6

Synthesis of 4-arm-PEG20k-CM-glycine-N-R848 (Compound 6)

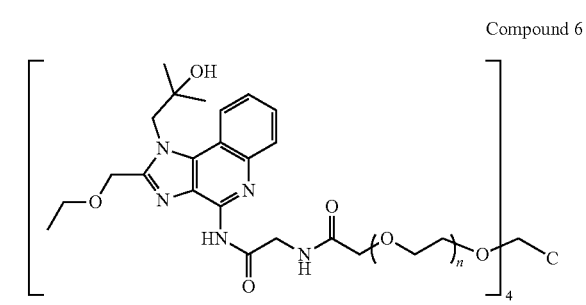

Compound 6

The title compound was synthesized according to the following reaction scheme.

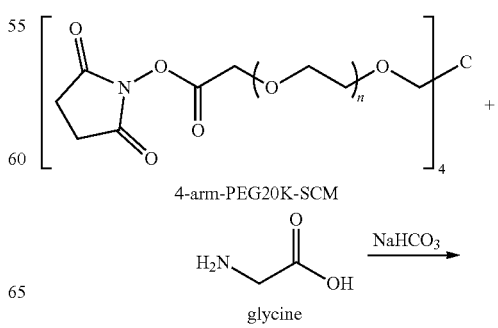

4-arm-PEG20K-SCM glycine

-continued

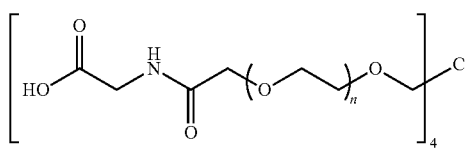

4-arm-PEG20k-CM-glycine:

Glycine (6.003 g, 10 equiv.) and sodium bicarbonate (6.720 g, 10 equiv.) were added into deionized water (800 ml) and the solution was stirred until it was clear. 4-arm-PEG20k-SCM (40.020 g, 1 equiv.) was added into the solution. The reaction solution was stirred at room temperature for 3 hours. 5N HCl solution was added into the solution to adjust the pH to 4.0. The solution was extracted with dichloromethane (2×150 ml). The organic phase was combined and dried with anhydrous sodium sulfate. The solid was removed by running through a frit. The filtrate was condensed to 50 ml and then added to 500 ml ethyl ether to obtain a precipitate. The product as white solid powder (35.050 g) was obtained by filtering and drying under high vacuum overnight.

$^1$H NMR (500 MHz, CDCl$_3$) δ 4.01 (d, 7.1H), 3.99 (s, 7.1H), 3.74-3.48 (m, 1818H), 3.35 (s, 7.1H).

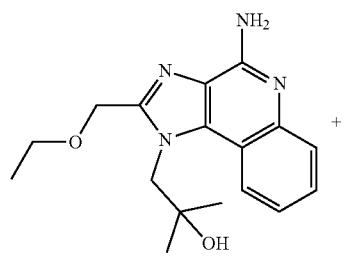

4-arm-PEG20k-CM-Glycine-N-R848:

At 20° C., 4-arm-PEG20k-CM-Glycine (2.520 g, 0.5 mmol COOH), hydroxybenzotriazole (135 mg, 1 mmol), N-(3-dimethylaminopropyl)-N'-ethylcarbodiimide hydrochloride (192 mg, 1 mmol), and N,N-diisopropylethylamine (258 mg, 2 mmol) were dissolved in dichloromethane (15 ml). The mixture was stirred at 20° C. for 30 minutes. R848 (189 mg, 0.6 mmol) was added. The reaction solution was stirred at 20° C. for 18 hours. The reaction solution was poured into 1 liter of ethyl ether while it was being stirred. The formed precipitate was collected by filtration and was washed with ethyl ether (50 ml). The obtained solid was added into isopropyl alcohol (300 ml) and the suspension was heated up to 60° C. to form clear solution. The solution was cooled to room temperature while being stirred. The formed precipitate was collected by filtration and was washed with ethyl ether (50 ml). The purification by precipitation in isopropyl alcohol was repeated one more time followed by drying under high vacuum overnight to give pure conjugate as white solid (1.823 g with 5.1% w/w R848 loading).

$^1$H NMR (500 MHz, CDCl$_3$) δ 8.97 (s, 3.56H), 8.18 (d, J=8.5 Hz, 3.52H), 8.16-8.11 (m, 2.77H), 7.81 (s, 2.92H), 7.63 (t, J=7.8 Hz, 3.06H), 7.51 (t, J=7.8 Hz, 3.48H), 4.98 (d, J=39.6 Hz, 13.32H), 4.81 (s, 6.64H), 4.13 (s, 6.20H), 3.65 (s, 1818H), 1.34 (s, 23.63H), 1.27 (t, J=7.1 Hz, 10.59H).

Alternate Synthesis of 4-arm-PEG20k-CM-glycine: t-Butyl Ester Protected 4-arm-PEG20k-CM-glycine was synthesized according to the following reaction scheme.

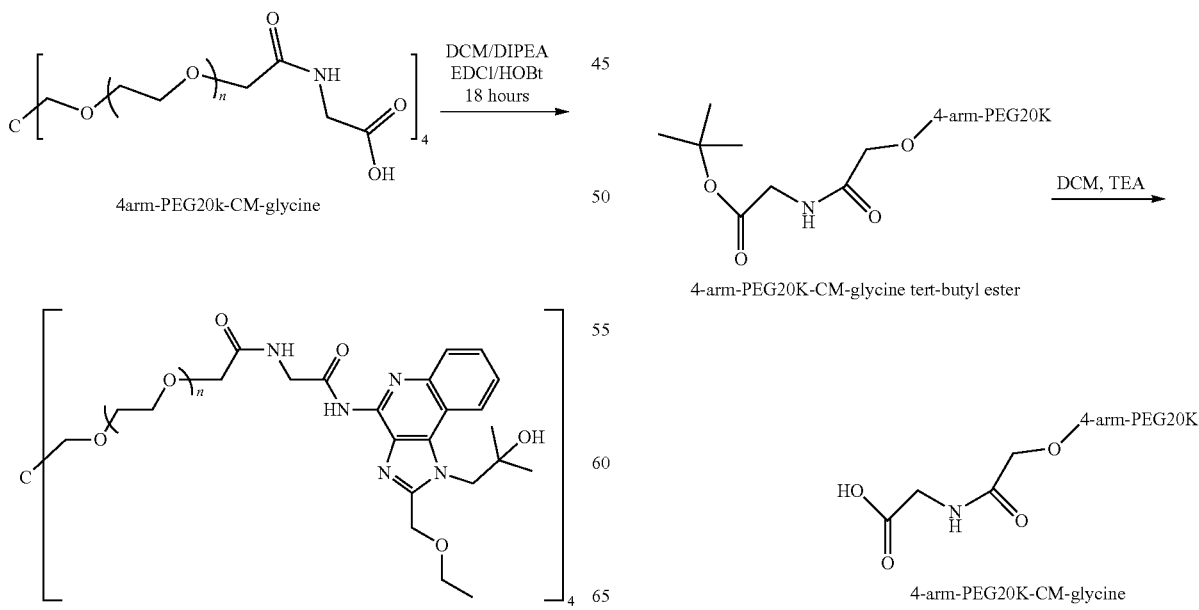

4-arm-PEG20k-CM-glycine t-butyl ester:

Glycine tert-butyl ester HCl (2.1 g, 12.6 mmol, 1.05 equiv.) was added into dichloromethane (300 ml) followed by addition of triethylamine (2.54 g, 25 mmol, 2.1 eqiv) and 4-arm-PEG20k-SCM (60 g, 3 mmol, MW of ~20,000). The reaction solution was stirred at room temperature for 12 hours and added to a stirring TBME (2.0 L) to precipitate the product. The product was isolated via filtration and washed with 30% MeOH/70% TBME (1 L) to remove NHS. The product was dried under vacuum for 12 hr to afford 4-arm-PEG20K-CM-glycine t-butyl ester (60.0 g).

4-arm-PEG20k-CM-glycine

TFA (225 ml) was added to a mixture of 4-arm-PEG20K-CM-glycine t-butyl ester (55 g) and DCM (75 ml). The resulting reaction solution was allowed to stir for 14 hours at room temperature. The reaction mixture was slowly added to a stirring TBME (2.4 L) to precipitate the product. The product was isolated via filtration and washed with 30% MeOH/70% TBME (1 L). The product was dried under vacuum to afford 4-arm-PEG20K-CM-glycine (54.0 g).

$^1$H NMR (500 MHz, CDCl$_3$) δ 4.01 (d, 7.1H), 3.99 (s, 7.1H), 3.74-3.48 (m, 1818H), 3.35 (s, 7.1H).

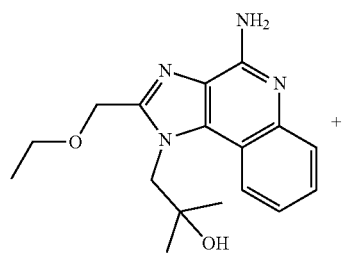

4-arm-PEG20k-CM-Glycine-N-R848:

The resulting 4-arm-PEG20k-CM-Glycine is used as in the above reaction scheme to produce 4-arm-PEG20k-CM-Glycine-N-R848.

Example 7

Synthesis of 4-arm-PEG20k-CM-(L)-alanine-N-R848 (Compound 7)

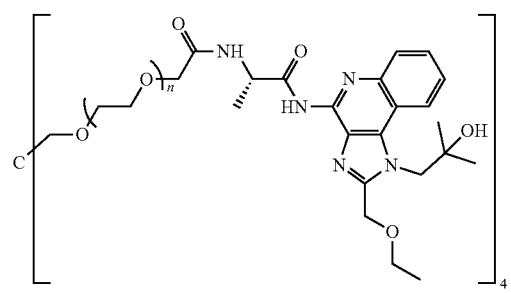

Compound 7

The title compound was synthesized according to the following reaction scheme.

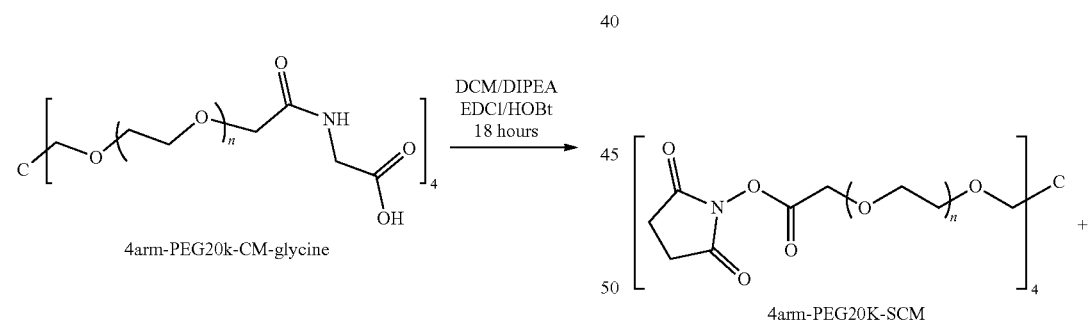

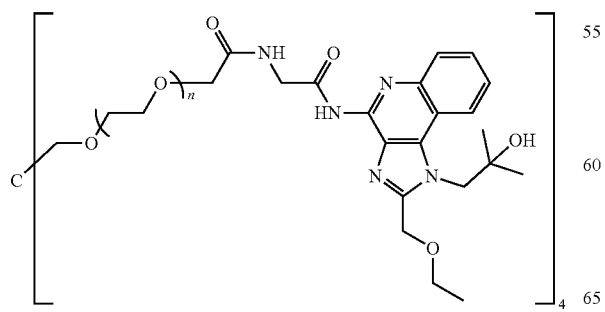

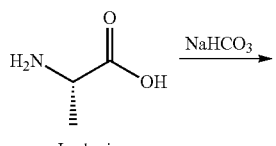

L-alanine

-continued

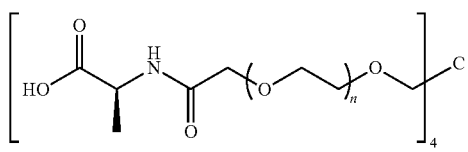

4-arm-PEG20k-CM-L-alanine:

L-alanine (7.100 g, 10 equiv.) and sodium bicarbonate (6.720 g, 10 equiv.) were added into deionized water (800 ml) and the solution was stirred until it was clear. Then 4-arm-PEG20k-SCM (40.030 g, 1 equiv.) was added into the solution. The reaction solution was stirred at 20° C. for 3 hours. 5N HCl solution was added into the solution to adjust pH to 4.0. The solution was extracted with dichloromethane (2×150 ml). The organic phase was combined and dried with anhydrous sodium sulfate. The solid was removed by running through a frit. The filtrate was condensed to 50 ml and then added to 500 mL ethyl ether to obtain precipitate. The product (35.012 g, yield 87%) as white solid powder was obtained by filtering and drying in vacuum overnight.

$^1$H NMR (500 MHz, CDCl$_3$) δ 4.42 (m, 3.56H), 3.85 (s, 7.11H), 3.58-3.33 (m, 1818H), 3.27 (s, 7.90H), 1.30 (d, 10.28H).

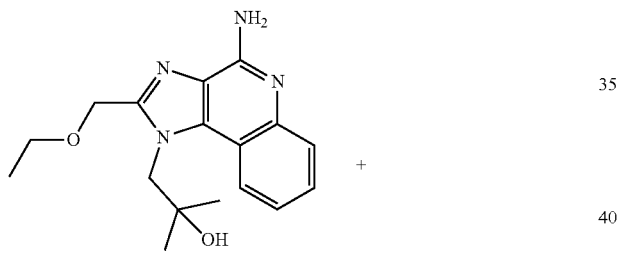

4-arm-PEG20k-CM-L-alanine-N-R848:

At 20° C., 4-arm-PEG20k-CM-L-alanine (2.500 g, 0.5 mmol of COOH), N,N-diisopropylethylamine (258 mg, 2.0 mmol), N-(3-dimethylaminopropyl)-N'-ethylcarbodiimide hydrochloride (192 mg, 1.0 mmol) and hydroxybenzotriazole (135 mg, 1 mmol) were dissolved in anhydrous dichloromethane (15 ml). R848 (189 mg, 0.6 mmol) was added in 30 minutes. The reaction solution was stirred at 20° C. for 18 hours. The reaction solution was poured into 1 liter of ethyl ether while being stirred. The formed precipitate was collected by filtration and was washed with ethyl ether (50 ml). The obtained solid was added into isopropyl alcohol (300 ml) and the suspension was heated to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 1.702 g as white solid with 4.2% (w/w) R848 loading.

$^1$H NMR (500 MHz, CDCl$_3$) δ 8.14 (d, J=8.4 Hz, 5.14H), 7.69-7.54 (m, 3.95H), 7.48 (d, J=8.0 Hz, 2.37H), 4.90 (s, 4.74H), 4.78 (s, 4.74H), 3.62 (br, 1818H), 1.60 (d, J=6.9 Hz, 5.93H), 1.39 (d, J=7.3 Hz, 5.93H), 1.36-1.27 (m, 21.73H), 1.24 (d, J=6.7 Hz, 15.80H).

Example 8

The Synthesis of 4-arm-PEG20k-CM-(L)-valine-N-R848 (Compound 8)

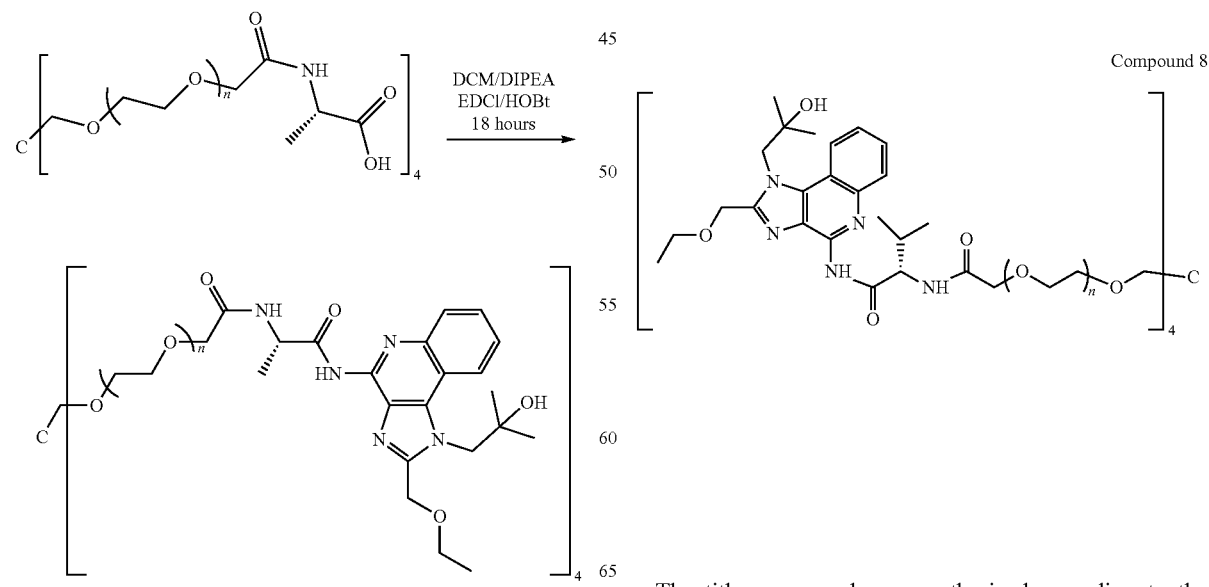

The title compound was synthesized according to the following reaction scheme.

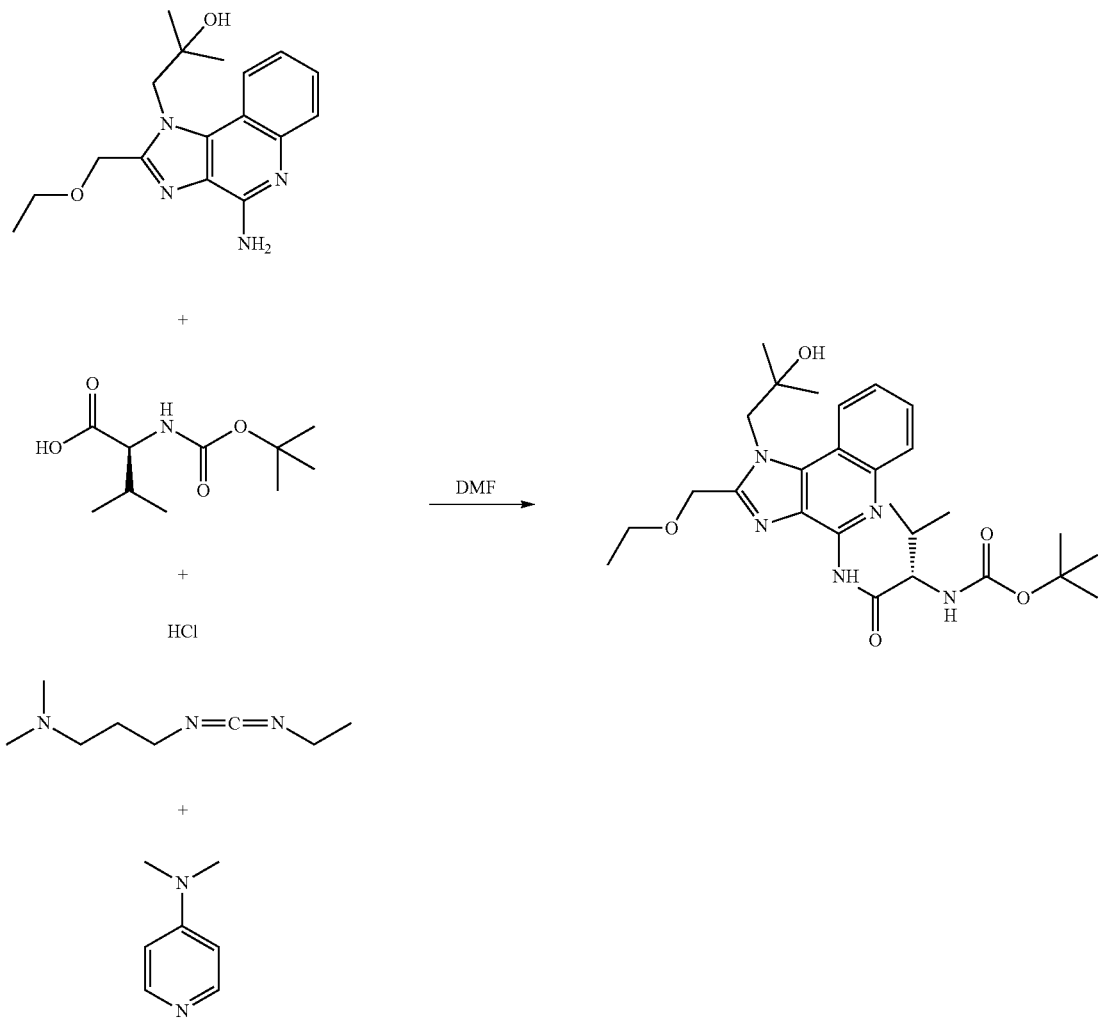

Boc-valine-R848:

1-(4-Amino-2-(ethoxymethyl)-1H-imidazo[4,5-c]quinolin-1-yl)-2-methylpropan-2-ol (R848) (237.5 mg, 0.755 mmol) was dissolved into anhydrous N,N-dimethylformamide (5 ml). Boc-L-valine (263.4 mg, 1.2 mmol) and 4-(dimethylamino)pyridine (187.4 mg, 1.534 mmol) were added. N-(3-dimethylaminopropyl)-N'-ethylcarbodiimide hydrochloride (236.1 mg, 1.232 mmol) was added. The resulting mixture was stirred at room temperature for 3 h. Water was added to quench the reaction. Brine was added. The mixture was extracted with ethyl acetate (2×50 ml). The combined organic solution was dried over anhydrous sodium sulfate, concentrated to dryness. The residue was purified with flash column chromatography on silica gel using 1-10% methanol/dichloromethane to afford product (394.7 mg) as white solid.

$^1$H-NMR (500 MHz, CDCl$_3$) δ 8.99 (br., 1H), 8.15-8.11 (m, 2H), 7.58 (t, J=7.5 Hz, 1H), 7.47 (t, J=7.5 Hz, 1H), 5.42 (m, 1H), 4.89 (br, 2H), 4.77 (s, 2H), 3.63 (q, J=7.0 Hz, 2H), 3.27 (m, 1H), 2.45 (br, 1H), 1.44 (s, 9H), 1.31 (br, 6H), 1.22 (t, J=7.0 Hz, 3H), 1.14 (br, 3H), 0.93 (d, J=6.0 Hz, 3H). LC-MS: 514 (MH$^+$/z).

Valine-R848.nTFA Salt:

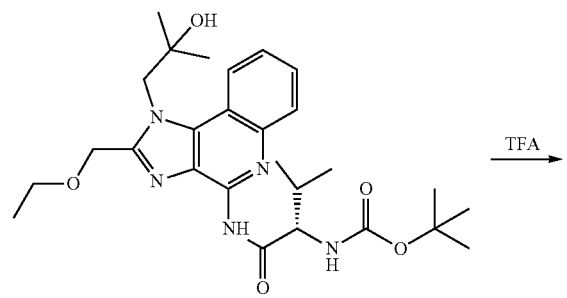

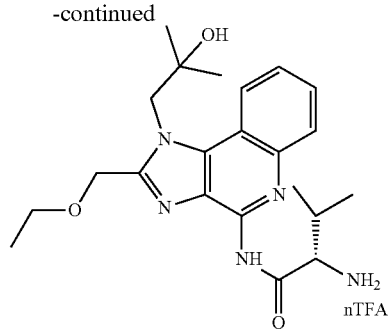

(S)-tert-butyl(1-((2-(ethoxymethyl)-1-(2-hydroxy-2-methylpropyl)-1H-imidazo[4,5-c]quinolin-4-yl)amino)-3-methyl-1-oxobutan-2-yl)carbamate (Boc-valine-R848) (377.0 mg, 0.73 mmol) was dissolved in dichloromethane (30 ml), and trifluoroacetic acid (3 ml, 38.8 mmol) was added. The resulting mixture was stirred at room temperature for 3.5 h. The mixture was concentrated to remove the solvent. The residue was dried under high vacuum to afford product (678.5 mg) as TFA salt.

LC-MS: 414 (MH+/z).

4-arm-PEG$_{20k}$-Valine-N-R848

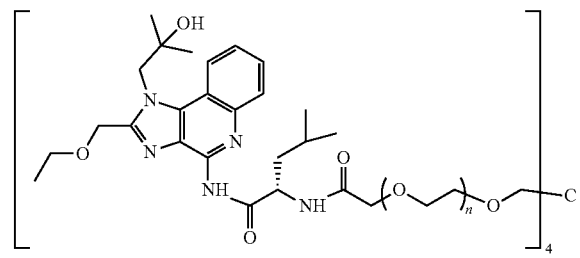

A solution of 4-arm-PEG20k-SCM (4.170 g, 0.74 mmol of SCM) in anhydrous dichloromethane (20 ml) was added to a mixture of valine-R848.nTFA (~0.734 mmol) and triethylamine (0.3 mL, 2.15 mmol) in N,N-dimethylformamide (1.0 ml) at room temperature. Dichloromethane (~10 mL) was used to dissolve the 4-arm-PEG20k-SCM residue in the vial and added to the reaction mixture. Triethylamine (0.15 mL, 1.076 mmol) was added. The resulting mixture was stirred at room temperature for 23 h. The reaction mixture was concentrated to remove the solvent. The residue was recrystallized with isopropyl alcohol (275 ml). The solid was washed with ethyl ether and dried under high vacuum overnight to afford 4.053 g of product as white solid. Drug loading was 4.3% (w/w).

$^1$H-NMR (500 MHz, CDCl$_3$) δ 8.99 (br), 8.10-8.09 (m, 6H), 7.54 (t, J=7.5 Hz, 3H), 7.47 (d, 3H). 7.42 (t, J=7.5 Hz, 3H), 4.840 (br, 6H), 4.712 (s, 6H), 4.07-3.95 (m, 6H), 3.72-3.42 (m, 1818H), 3.39 (m, 3H), 2.41 (br, 6H), 1.36 (br, 18H), 1.16 (t, J=6.5 Hz, 9H), 1.12 (m, 9H), 0.92 (d, J=6.0 Hz, 9H).

Example 9

Synthesis of 4-arm-PEG20k-CM-(L)-leucine-N-R848 (Compound 9)

Compound 9

The title compound was synthesized according to the following reaction scheme.

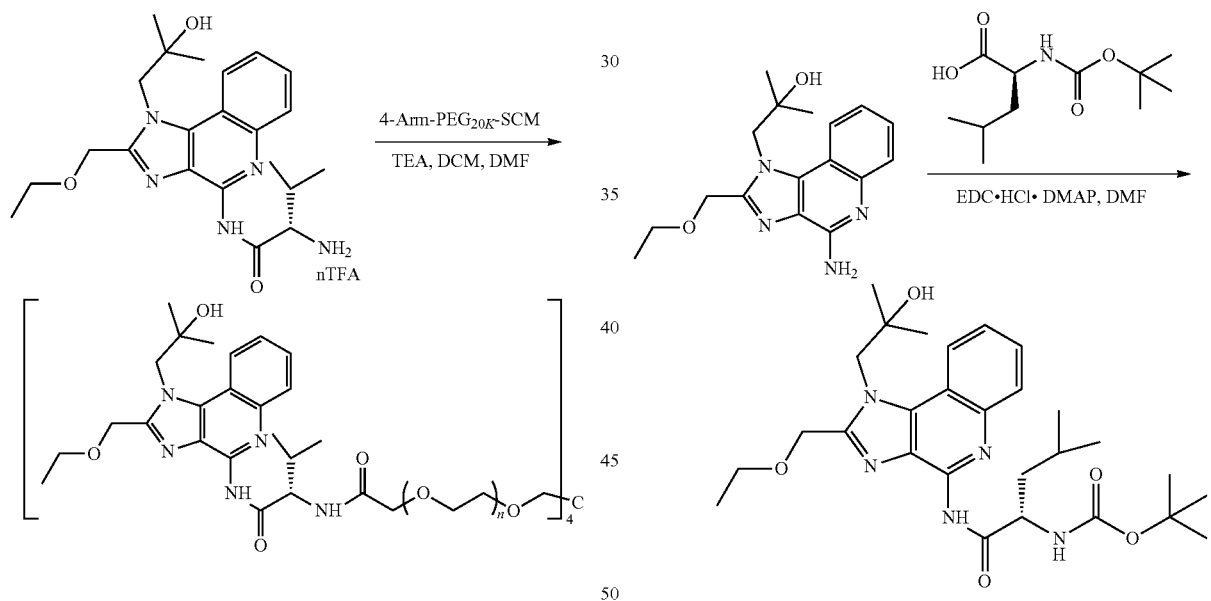

Boc-Leu-R848:

1-(4-Amino-2-(ethoxymethyl)-1H-imidazo[4,5-c]quinolin-1-yl)-2-methylpropan-2-ol (R848) (421.8 mg, 1.34 mmol) was dissolved into N,N-dimethylformamide (10 ml). Boc-Leu-OH (501.4 mg, 2.207 mmol) and 4-(dimethylamino)pyridine (344.6 mg, 2.82 mmol) were added. N-(3-dimethylaminopropyl)-N'-ethylcarbodiimide hydrochloride (438.2 mg, 2.286 mmol) was added. The resulting mixture was stirred at room temperature for 18 h. Water was added to quench the reaction. Brine was added. The mixture was extracted with ethyl acetate (2×50 ml). The combined organic solution was dried over anhydrous sodium sulfate, and concentrated to dryness. The residue was purified with flash column chromatography on silica gel using 1-10% methanol/dichloromethane to afford 494 mg of product as white solid in 70% yield.

¹H-NMR (500 MHz, CDCl₃) δ 9.03 (br, 1H), 8.16 (d, J=8.0 Hz, 1H), 8.17 (d, J=8.0 Hz, 1H), 7.57 (t, J=7.5 Hz, 1H), 7.46 (t, J=7.5 Hz, 1H), 5.26 (m, 1H), 4.85 (br, 2H), 4.77 (s, 2H), 3.63 (q, J=7.0 Hz, 2H), 3.26 (m, 1H), 1.89 (m, 2H), 1.69 (s, 3H), 1.56 (m, 1H), 1.43 (s, 9H), 1.31 (br, 3H), 1.22 (t, J=7.0 Hz, 3H), 1.08 (br, 3H), 0.94 (d, J=6.0 Hz, 3H). LC-MS: 528 (MH⁺/z).

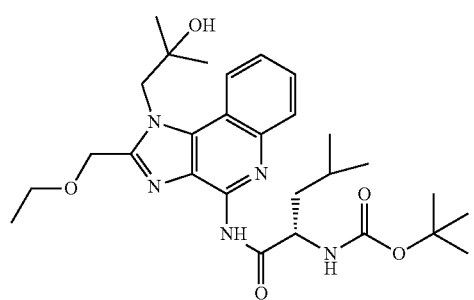

TFA →

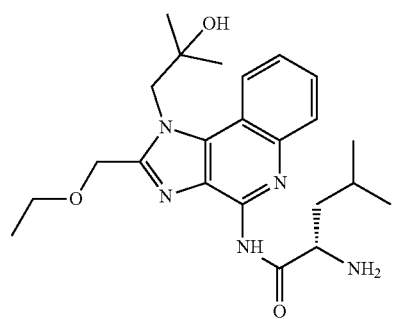

nTFA

Leu-R848.nTFA salt:

(S)-tert-butyl(1-((2-(ethoxymethyl)-1-(2-hydroxy-2-methylpropyl)-1H-imidazo[4,5-c]quinolin-4-yl)amino)-4-methyl-1-oxopentan-2-yl)carbamate (Boc-Leu-R848) (494 mg, 0.936 mmol) was dissolved in dichloromethane (20 ml), and trifluoroacetic acid (3 ml, 38.8 mmol) was added. The resulting mixture was stirred at room temperature for 4 h. The mixture was concentrated to remove the solvent. The residue was dried under high vacuum to afford product (895.7 mg) as TFA salt.

LC-MS: 428 (MH⁺/z).

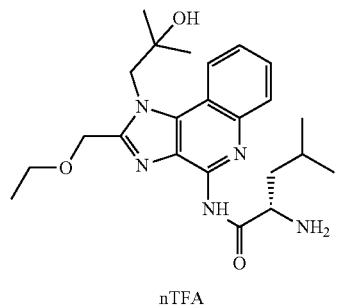

nTFA

4-Arm-PEG20K-SCM
TEA, DCM, DMF →

-continued

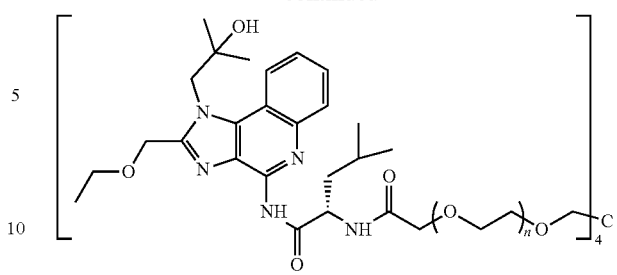

4-arm-PEG20k-CM-L-Leucine-R848:

A solution of 4-arm-PEG20k-SCM (5.200 g, 0.96 mmol of SCM) in anhydrous dichloromethane (30 ml) was added to a solution of R848-Leu-NH₂.nTFA (0.936 mmol) in N,N-dimethylformamide (1.0 ml) at room temperature. Dichloromethane (~10 mL) was used to dissolve the residue of 4-arm-PEG20k-SCM in the vial, which was added to the reaction mixture. Triethylamine (0.35 ml, 2.51 mmol) was added. The resulting mixture was stirred at room temperature for 35 min. Triethylamine (0.25 ml, 1.79 mmol) was added. The mixture was stirred at room temperature for 19 h. The reaction mixture was concentrated to remove the solvent. The residue was recrystallized with isopropyl alcohol (275 ml). The solid was washed with ethyl ether and dried under high vacuum overnight to afford 5.12 g of white solid as product. Drug loading was 4% (w/w).

¹H-NMR (500 MHz, CDCl₃) δ 8.09-8.08 (m, 5.5H), 7.51 (t, J=7.5 Hz, 2.75H), 7.40 (m, 5.5H). 4.85 (br, 5.5H), 4.70 (s, 5.5H), 4.02-3.91 (m, 5.5H), 3.70-3.32 (m, 1818H), 1.81 (m, 2.75H), 1.72 (br, 2.75H), 1.63 (m, 2.75H), 1.22 (m, 16.5H), 1.12 (t, J=6.0 Hz, 8.25H), 0.95 (br, 8.25H), 0.86 (d, J=6.0 Hz, 8.25H).

Example 10

Synthesis of 4-arm-PEG20k-CM-α,α-dimethyl-glycine-N-R848 (Compound 10)

Compound 10

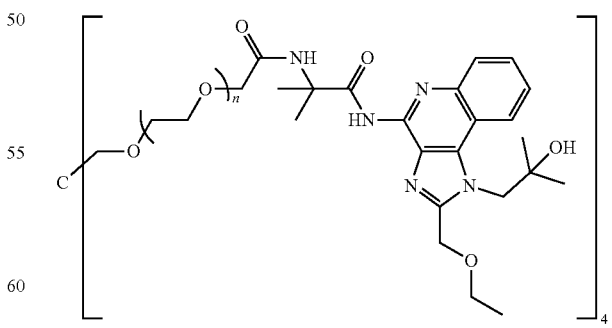

The title compound was synthesized according to the following reaction scheme.

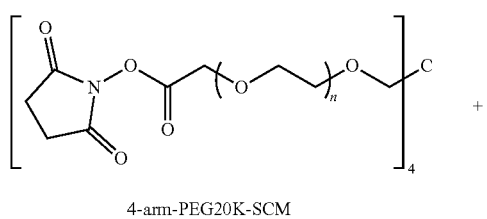

4-arm-PEG20K-SCM

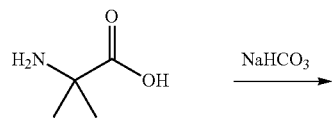

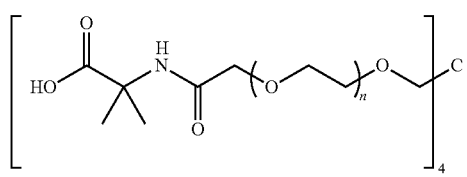

4-arm-PEG20k-CM-α,α-dimethyl-glycine:

2-Amino-2-methylpropanoic acid (2.890 g, 28 mmol) and sodium bicarbonate (2.352 g, 28 mmol) were dissolved in water (40 ml). 4-arm-PEG20k-SCM (7.0 g, 1.4 mmol of SCM) was added in portions. The reaction mixture was stirred at 20° C. for 18 hours. The reaction was neutralized with 1M HCl (42 ml) to pH 4.7. The reaction mixture was saturated with sodium chloride and extracted with dichloromethane (3×100 ml). Organic phase was dried over anhydrous magnesium sulfate and concentrated. Residue was recrystallized with isopropyl alcohol (500 ml) to give 4.710 g white solid 4-arm-PEG20k-CM-α,α-dimethyl-glycine with 80% substitution.

$^1$H NMR (500 MHz, CDCl$_3$) δ 7.45 (s, 3.56H), 4.15 (s, 2.77H), 3.97 (s, 2.77H), 3.64 (br, 1818H), 3.41 (s, 7.90H), 1.62 (s, 19.36H).

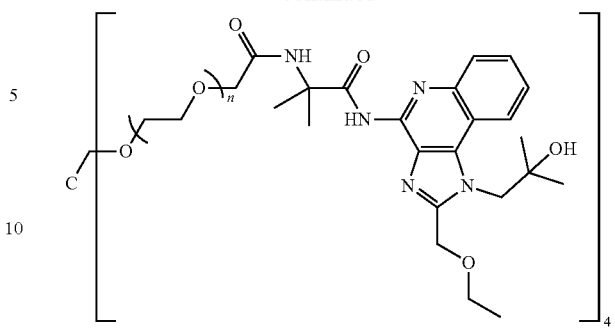

4-arm-PEG20k-CM-α,α-dimethyl-glycine-N-R848:

At 20° C., 4-arm-PEG20k-CM-α,α-dimethyl-glycine (2.000 g, 0.43 mmol of COOH), N,N-diisopropylethylamine (258 mg, 2.0 mmol), N-(3-dimethylaminopropyl)-N'-ethyl-carbodiimide hydrochloride (153 mg, 0.9 mmol), and hydroxybenzotriazole (108 mg, 0.9 mmol) were dissolved in anhydrous dichloromethane (15 ml). R848 (138 mg, 0.44 mmol) was added in 30 minutes. The reaction solution was stirred at 20° C. for 18 hours. The reaction solution was poured into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and washed with ethyl ether (50 ml). The purification by precipitation in isopropyl alcohol was repeated once more and followed by drying under high vacuum overnight to give pure conjugate 1.819 g as white solid with 4.7% (w/w) R848 loading.

$^1$H NMR (500 MHz, CDCl$_3$) δ 9.71 (s, 3.95H), 8.29-8.03 (m, 3.95H), 7.57 (s, 3.95H), 7.45 (s, 3.95H), 4.83 (d, J=66.8 Hz, 11.85H), 3.61 (br, 1818H), 2.50 (s, 7.90H), 1.76 (s, 11.85H), 1.42 (s, 3.95H), 1.26 (d, J=34.3 Hz, 27.65H).

Example 11

Synthesis of mPEG5k-carbamate-N-R848 (Compound 11)

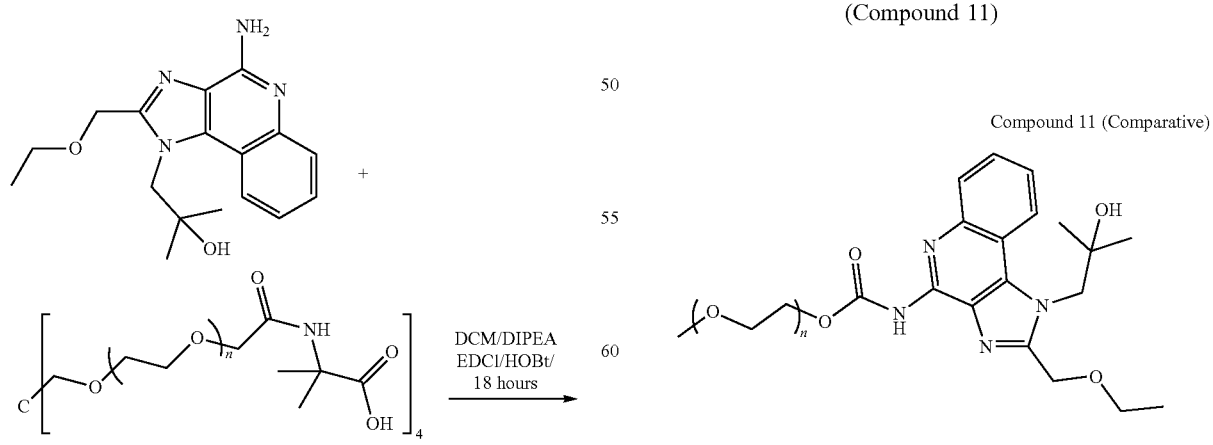

Compound 11 (Comparative)

The title compound was synthesized according to the following reaction scheme.

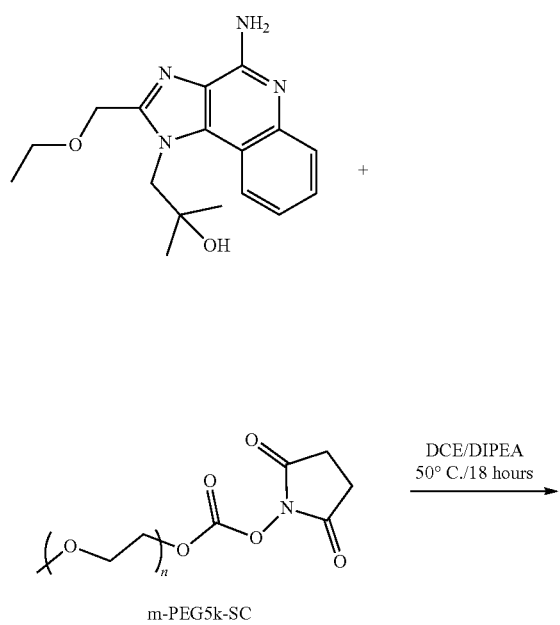

m-PEG5k-SC

Example 12

Synthesis of 4-arm-PEG20k-carbamate-N-R848 (Compound 12)

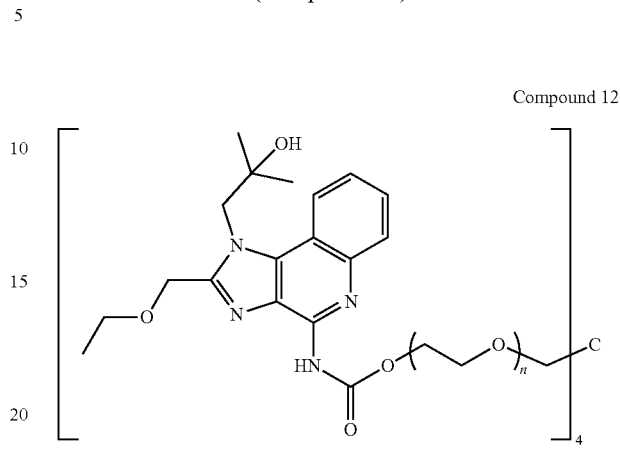

Compound 12

The title compound was synthesized according to the following reaction scheme.

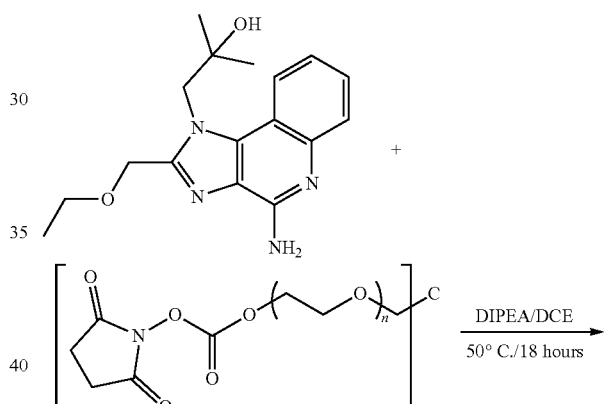

4-arm-PEG20K-SC

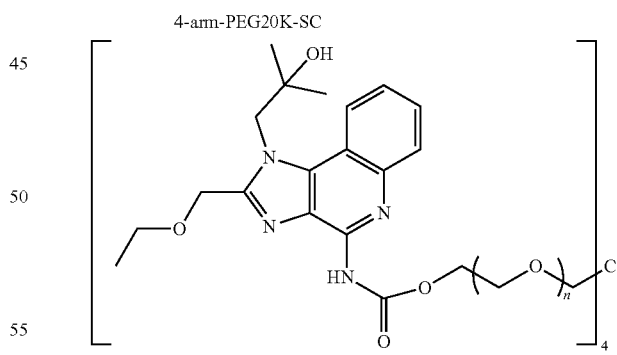

mPEG5k-carbamate-N-R848:

At 50° C., mPEG5k-SC (2.500 g, 0.5 mmol), R848 (236 mg, 0.75 mmol), and N,N-diisopropylethylamine (129 mg, 1.0 mmol) were dissolved in anhydrous N,N-dimethylformamide (20 ml). The reaction solution was stirred at 50° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate 2.338 g as white solid with 4.5% (w/w) R848 loading.

$^1$H NMR (500 MHz, CDCl$_3$) δ 8.18 (s, 0.77H), 8.13 (dd, J=8.4, 1.3 Hz, 0.78H), 7.59 (ddd, J=8.4, 7.0, 1.3 Hz, 0.82H), 7.49-7.44 (m, 0.82H), 4.91 (s, 1.7H), 4.78 (s, 1.7H), 4.43 (d, J=4.8 Hz, 1H), 3.63 (br, 574H), 3.37 (s, 3H), 1.32 (s, 5H), 1.25 (t, J=7.0 Hz, 2H).

4-arm-PEG20k-carbamate-N-R848:

At 50° C., 4-arm-PEG20k-SC (5.0 g, 1.0 mmol of SCM) and R848 (377 mg, 1.2 mmol) were dissolved in anhydrous 1,2-dichloroethane (25 ml). N,N-diisopropylethylamine (129 mg, 2 mmol) was added into the solution. The reaction solution was stirred at 50° C. for 18 hours. The reaction solution was added into 1 liter of ethyl ether while being stirred. The formed precipitate was collected by filtration and was washed with ethyl ether (50 ml). The obtained solid was added into isopropyl alcohol (300 ml) and the suspension was heated up to 60° C. to form a clear solution. The solution was cooled to room temperature while being stirred. The precipitate was formed and collected by filtration and was washed with ethyl ether (50 ml). The purification by precipitation in isopropyl alcohol was repeated once more and followed by drying under high vacuum overnight to give pure conjugate 4.240 g as white solid with 4.5% (w/w) R848 loading.

$^1$H NMR (500 MHz, CDCl$_3$) δ 8.16 (t, J=8.7 Hz, 5.93H), 7.61 (t, J=7.7 Hz, 3.16H), 7.48 (t, J=7.7 Hz, 3.16H), 4.93 (s, 2.96H), 4.80 (s, 5.93H), 4.45 (t, J=4.8 Hz, 2.96H), 3.82 (t, J=4.8 Hz, 2.96H), 3.79 (t, J=5.0 Hz, 5.93H), 3.65 (br, 1818H), 3.42 (s, 3.16H), 1.33 (s, 19.75H), 1.26 (t, J=7.0 Hz, 7.90H).

Example 13

Synthesis of 4-arm-PEG20k-urea-N-R848 (Compound 13)

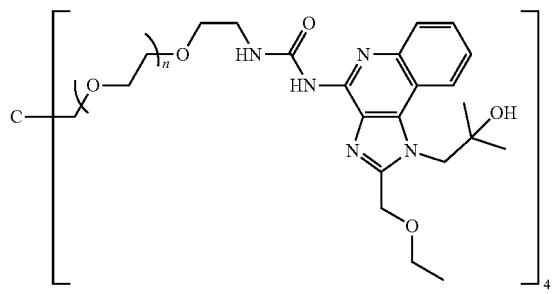

Compound 13

The title compound was synthesized according to the following reaction scheme.

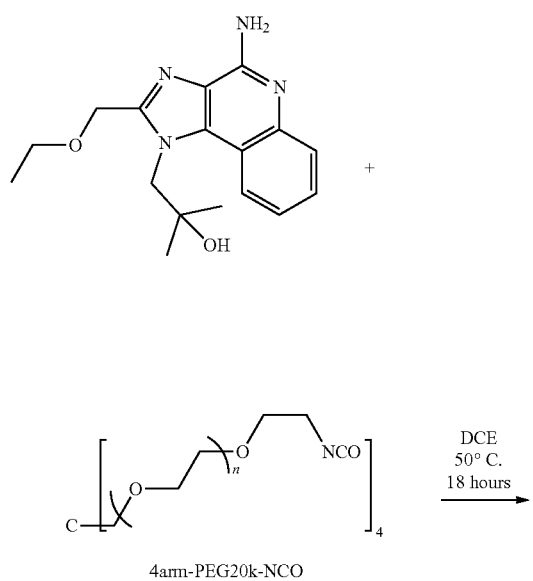

4arm-PEG20k-NCO

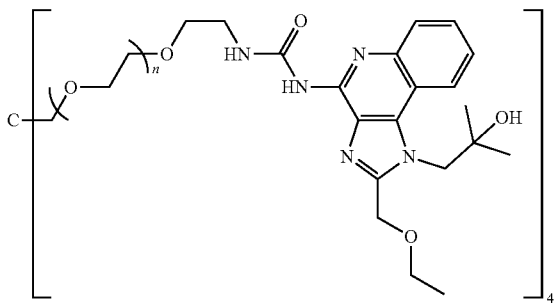

4-arm-PEG20k-urea-N-R848:

At 50° C., 4-arm-PEG20k-isocyanate (1.0 g, 0.2 mmol NCO) and R848 (69.2 mg, 0.22 mmol) were dissolved in anhydrous 1,2-dichlororthane (10 ml). The reaction solution was stirred at 50° C. for 18 hours. The reaction solution was poured into 0.5 liter of ethyl ether while being stirred. The formed precipitate was collected by filtration and was washed with ethyl ether (50 ml). The obtained solid was added into isopropyl alcohol (250 ml) and the suspension was heated up to 60° C. to form a clear solution. The solution was cooled to room temperature while being stirred. The formed precipitate was collected by filtration and was washed with ethyl ether (50 ml). The purification by precipitation in isopropyl alcohol was repeated once more and followed by drying under high vacuum overnight to give pure conjugate as white solid 938 mg with 4.7% (w/w) R848 loading.

$^1$H NMR (500 MHz, CDCl$_3$) δ 10.30 (d, J=5.5 Hz, 3.56H), 8.17-8.09 (m, 7.11H), 7.94 (d, J=8.3 Hz, 3.56H), 7.57 (t, J=7.8 Hz, 3.56H), 7.43 (t, J=7.8 Hz, 3.56H), 4.92 (s, 7.51H), 4.77 (s, 7.51H), 3.63 (br, 1818H), 1.32 (s, 23.70H), 1.24 (t, J=7.1 Hz, 10.67H).

Example 14

Synthesis of 4-arm-PEG20k-CM-imiquimod (Compound 14)

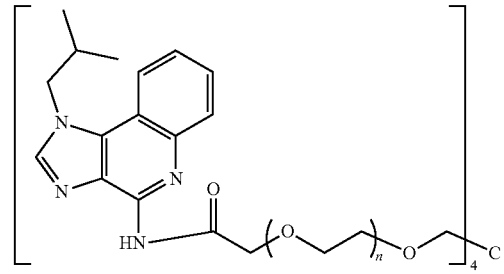

Compound 14

The title compound was synthesized according to the following reaction scheme.

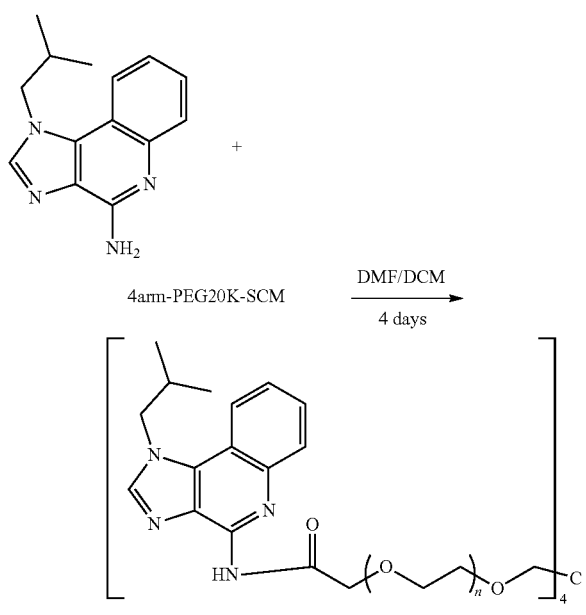

4arm-PEG20K-SCM  →  DMF/DCM, 4 days

4-arm-PEG20k-CM-imiquimod:

4-arm-PEG20k-SCM (6.789 g, 1.2 mmol of SCM) was dissolved in anhydrous dichloromethane (33 ml), and then was added to a suspension of imiquimod (359.7 mg, 1.452 mmol) in N,N-dimethylformamide (5.0 ml) at room temperature. Dichloromethane (~10 mL) was used to dissolve the 4-arm-PEG20k-SCM residue and added to the reaction mixture. The resulting mixture was stirred at room temperature for 3 days. Dichloromethane (10 ml) was added. The mixture was stirred at room temperature for another day. The reaction mixture was concentrated to remove the solvents. The residue was recrystallized twice with isopropyl alcohol to afford 4.8612 g of product as white solid. Drug loading was 3.9% (w/w).

$^1$H NMR (500 MHz, CDCl$_3$) δ 9.55 (br, 2.5H), 8.026 (m, 3.2H), 7.853 (d, J=8.0 Hz, 3.3H), 7.720 (s, 3.3H), 7.450 (t, J=8.0 Hz, 3.3H), 7.371 (t, J=8.0 Hz, 3.3H), 4.30-4.18 (m, 13.26H), 3.471 (m, 1818H), 2.190 (m, 3.1H), 0.877 and 0.986 (2s, 20.4H).

Example 15

Synthesis of 4-arm-PEG40k-CM-N-imiquimod (Compound 15)

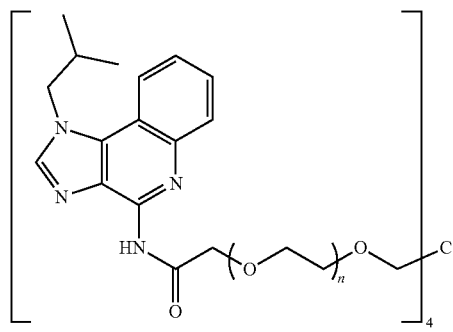

Compound 15

The title compound was synthesized according to the following reaction scheme.

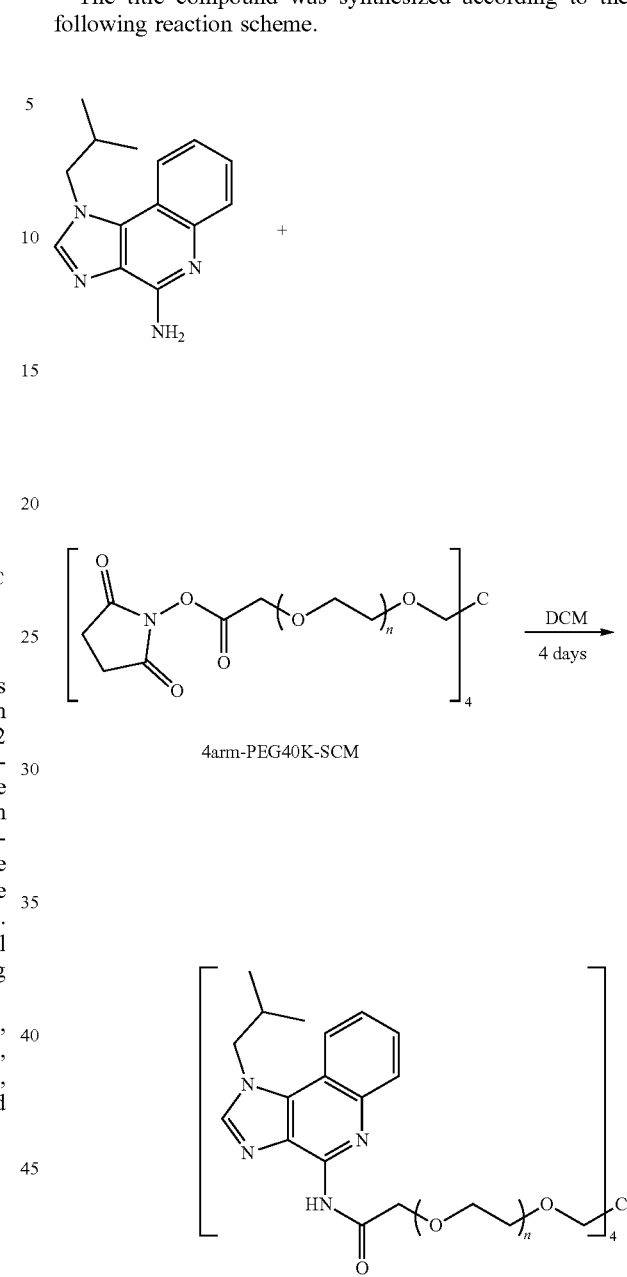

4-arm-PEG40k-CM-N-imiquimod:

4-arm-PEG40k-SCM (5.110 g, 0.51 mmol of SCM) was dissolved in anhydrous dichloromethane (33 ml), and imiquimod (148 mg, 0.61 mmol) was added at room temperature. The resulting suspension was stirred at room temperature for 4 days to form a clear solution. The reaction mixture was concentrated to remove the solvent. The residue was recrystallized twice with isopropyl alcohol (250 ml) as mentioned above to afford 4.609 g of product as white solid. The product contained 1.8% (w/w) imiquimod based on NMR analysis.

$^1$H NMR (500 MHz, CDCl$_3$) δ 8.21 (d, 3.06H), 8.02 (d, 3.06H), 7.85 (s, 3.15H), 7.63 (t, 3.34H), 7.53 (t, 3.17H), 4.34 (d, 6.21H), 3.89-3.43 (m, 3636H), 1.03 (s, 18.09H).

Example 16

Synthesis of 4-arm-PEG20k 4-((6-amino-8-hydroxy-2-(2-methoxyethoxy)-9H-purin-9-yl)methyl)-benzamide (Compound 16)

Compound 16

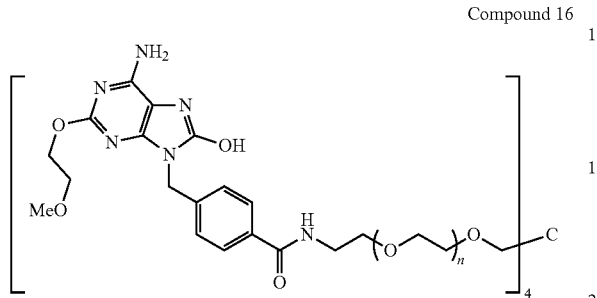

The title compound was synthesized according to the following reaction scheme.

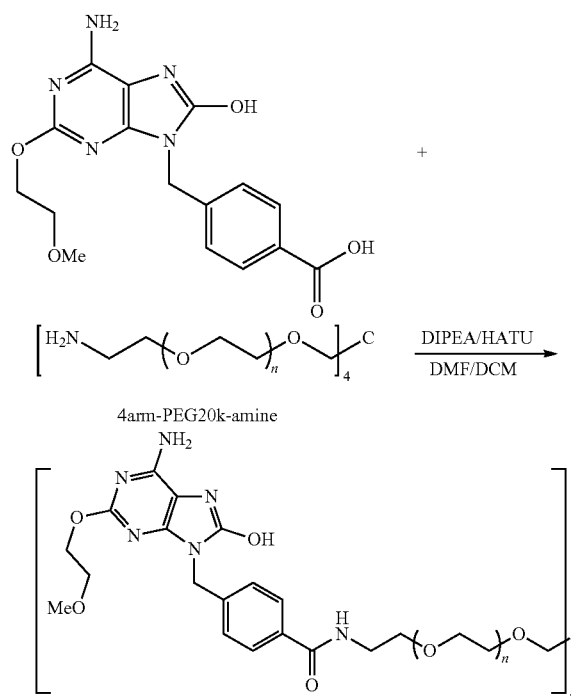

At 20° C., 4-arm-PEG20k-amine (1.500 g, 0.3 mmol of amine) was dissolved in dichloromethane (3 ml). The solution was added into N,N-dimethylformamide (10 ml) solution containing N, N-diisopropylethylamine (116 mg, 0.9 mmol), 1-[bis(dimethylamino)methylene]-1H-1,2,3-triazolo[4,5-b]pyridinium-3-oxid hexafluorophosphate (137 mg, 0.36 mmol), and 4-((6-amino-8-hydroxy-2-(2-methoxyethoxy)-9H-purin-9-yl)methyl) benzoic acid (108 mg, 0.3 mmol). The reaction mixture was stirred at 20° C. for 18 hours. The reaction solution was added into 0.3 liter of ethyl ether while being stirred. The formed precipitate was collected by filtration and was washed with ethyl ether (50 ml). The obtained solid was purified by flash chromatography with 10-30% methanol in dichloromethane. The product was dissolved in 20 ml dichloromethane and filtered. The filtrate was concentrated and precipitated in ethyl ether again to give pure conjugate 300 mg as white solid with 6.0% (w/w) drug loading.

$^1$H NMR (500 MHz, CDCl$_3$) δ 9.26 (s, 3.95H), 7.78 (d, J=7.9 Hz, 7.90H), 7.52 (d, J=7.9 Hz, 7.90H), 5.67 (s, 7.90H), 5.04 (s, 7.90H), 4.42 (t, J=5.0 Hz, 7.90H), 3.66 (br, 1818H).

Example 17

In Vivo Study: Demonstration of TLR7/8-Dependent Cytokine Production

Studies were conducted to evaluate TLR7/8-dependent cytokine production in plasma, by measuring induction of cytokines following TLR7/8 agonism by Compound 6 or R848.

Method

Compound 6, R848, or vehicle (HBSS; Hank's Balanced Salt Solution) was administered intratumorally to Balb/c mice bearing CT26 tumor. Dose was 10 μg Compound 6 (R848 equivalent) or 10 μg R848. (Conjugate doses and concentrations are expressed based on TLR 7/8 agonist (e.g., resiquimod or other TLR 7/8 agonist) content, wherein the mass of the TLR 7/8 agonist is expressed independent of PEG mass). Plasma was collected at pre-determined time points for analysis of level of IFN-gamma, IL-2, IL-4, IL5, IL-6, IL-1 beta, IL-10, IL-12p70, KC/GRO, TNF-alpha, and IFN-alpha.

For assessing IFN-gamma, IL-2, IL-4, IL5, IL-6, IL-1 beta, IL-10, IL-12p70, KC/GRO, and TNF alpha, an electrochemiluminescence assay was performed on duplicate samples using capture antibody precoated 96 well multispot plates from Meso Scale Discovery (MSD; Gaithersburg, Md., US). Specific cytokine levels were quantitated by adding detection antibody labeled with MSD SULFO-TAG reagent to each well and incubated for 2 hours at room temperature. Plates were immediately read using SECTOR Imager 2400 and data was quantitated using Discovery Workbench software version 4.0 (MSD, Gaithersburg, Md., US).

Mouse IFN alpha was measured with the Verikine mouse Interferon-Alpha ELISA kit (PBL, Piscataway, N.J., USA), according to the instructions of the manufacturer. After the addition of a stop solution, the absorbance at 450 nm was determined using BioTek μQuant microplate reader (Biotek; Winooski, Vt., USA). The ELISA data was quantitated using Biotek Gen5 software (Biotek; Winooski, Vt., USA). Data are represented as the mean of the fold-change of replicates.

Results

Results are provided in Table 1 and Table 2 as an average of three animals.

TABLE 1

Cytokine production at 2 hours following single 10 μg intratumoral administration of test compound.

| Test compound | Fold change (treated/vehicle) | | | | |
| --- | --- | --- | --- | --- | --- |
| | IL6 | IFNa | IL12 | KC/GRO | TNFa |
| R848 | ++++ | ++ | ++ | + | ++ |
| Compound 6 | ++ | + | + | + | + |

Fold-change is provided as follows:
NA is Not Applicable
- - - is not tested
+<50≤++<200≤+++<800≤++++

TABLE 2

Cytokine production at 6 hours following single
10 μg intratumoral administration of test compound

| Test compound | Fold change (treated/vehicle) | |
| --- | --- | --- |
| | IFNg | IL10 |
| R848 | ++++ | ++ |
| Compound 6 | +++ | + |

Fold-change is provided as follows:
NA is Not Applicable
- - - is not tested
+<5≤++<10≤+++<20≤++++

Intratumoral administration of Compound 6 resulted in induction of cytokines in plasma but at a reduced level to the induction observed with R848 parent molecule. These results demonstrate that PEGylation of R848 reduces the systemic production of plasma cytokines, reducing the potential for toxicity.

Example 18

In Vivo Study: Plasma and Tumor Pharmacokinetics and Cytokine Production

Studies were conducted to evaluate the single dose pharmacokinetics of R848 and Compound 6 in plasma and tumor tissue.

R848 or Compound 6 was administered intratumorally to Balb/c mice bearing a CT26 or EMT6 tumor. The dose for both R848 and Compound 6 was 10 μg (R848 equivalents). Plasma and tumor tissues were collected at pre-determined time points for analysis of R848 and Compound 6 using a qualified LC-MS/MS method.

Results are provided in Tables 3A and 3B. Results provided are an average of 3 animals and are provided as R848 equivalent.

TABLE 3A

Plasma and tumor concentrations following single intratumoral
administration of test compound to CT26 tumor bearing mice

| Test compound | Time post-dose (hr) | R848 plasma concentration (ng/mL) | R848 tumor concentration (ng/g) | Compound 6 plasma concentration (ng/mL*) | Compound 6 tumor concentration (ng/g*) |
| --- | --- | --- | --- | --- | --- |
| R848 | 0.25 | ++ | ++ | NA | NA |
| | 2.00 | + | + | NA | NA |
| | 6.00 | + | + | NA | NA |
| | 24.00 | + | + | NA | NA |
| | 48.00 | BLQ | + | NA | NA |
| | 72.00 | BLQ | + | NA | NA |
| | 96.00 | BLQ | + | NA | NA |
| | 120.00 | BLQ | + | NA | NA |
| | 144.00 | BLQ | + | NA | NA |
| Compound 6 | 0.25 | + | + | +++ | +++ |
| | 2.00 | + | + | +++ | +++ |
| | 6.00 | + | + | +++ | ++ |
| | 24.00 | + | + | +++ | ++ |
| | 48.00 | + | + | ++ | + |
| | 72.00 | + | + | BLQ | + |
| | 96.00 | BLQ | + | BLQ | + |
| | 120.00 | + | + | BLQ | + |
| | 144.00 | + | + | BLQ | + |

*R848 Equivalent

TABLE 3B

Plasma and tumor concentrations following single intratumoral
administration of test compound to EMT6 tumor bearing mice

| Test compound | Time post-dose (hr) | R848 plasma concentration (ng/mL) | R848 tumor concentration (ng/g) | Compound 6 plasma concentration (ng/mL*) | Compound 6 tumor concentration (ng/g*) |
| --- | --- | --- | --- | --- | --- |
| R848 | 0.25 | +++ | ++ | NA | NA |
| | 2.00 | + | + | NA | NA |
| | 6.00 | + | + | NA | NA |
| | 24.00 | BLQ | + | NA | NA |
| | 48.00 | BLQ | + | NA | NA |
| | 72.00 | BLQ | + | NA | NA |
| | 96.00 | BLQ | + | NA | NA |
| | 120.00 | BLQ | + | NA | NA |
| | 144.00 | BLQ | + | NA | NA |
| Compound 6 | 0.25 | + | + | ++ | +++ |
| | 2.00 | + | + | +++ | +++ |
| | 6.00 | + | + | +++ | ++ |
| | 24.00 | + | + | ++ | + |
| | 48.00 | + | + | ++ | + |
| | 72.00 | BLQ | + | BLQ | + |
| | 96.00 | BLQ | + | BLQ | + |
| | 120.00 | BLQ | + | BLQ | + |
| | 144.00 | BLQ | + | BLQ | BLQ |

*R848 Equivalent

Plasma concentration is provided as follows:
NA is Not Applicable
BLQ is Below the Limit of Quantitation
- - - is not tested
+<10≤++<100≤+++<1,000≤++++
Tumor concentration is provided as follows:
NA is Not Applicable
BLQ is Below the Limit of Quantitations—is not tested
+<1,000≤++<10,000≤+++<100,000≤++++

When compared to intratumoral administration of R848, intratumoral administration of Compound 6 is an effective method for retaining Compound 6 (and locally released R848) in the treated tumor while significantly reducing the peak systemic concentration of released R848, which is in agreement with observed, lower peak induction of systemic cytokines.

Cytokine analysis (in CT26 tumor-bearing mice): Tumor and plasma samples were obtained at multiple time points following administration for cytokine analysis. RNA was isolated from treated tumors to assess induction of type I interferon- and NFκB-dependent gene expression. A panel of pro-inflammatory cytokines was measured from tumor tissue and plasma by multiplex protein measurement assay.

Figure 6A:
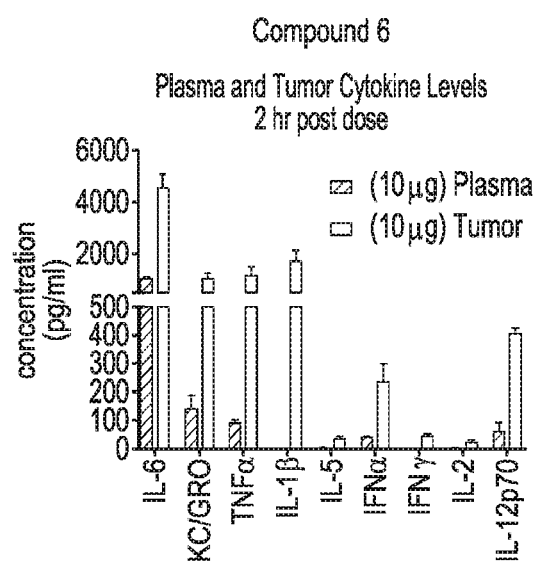
FIGS. 6A and 6B are graphs providing a comparison of tumor and plasma cytokine concentrations at 2 hours and at 6 hours, respectively, following treatment with Compound 6, as described in Example 18. The concentration of systemic cytokines was significantly less than that in the tumor for each of the cytokines measured (IL-6, KC/GRO, TNF-α, IL-1β, IL-5, IFN-α, IFN-γ, IL-2 and IL-12p70).
Figure 6B:
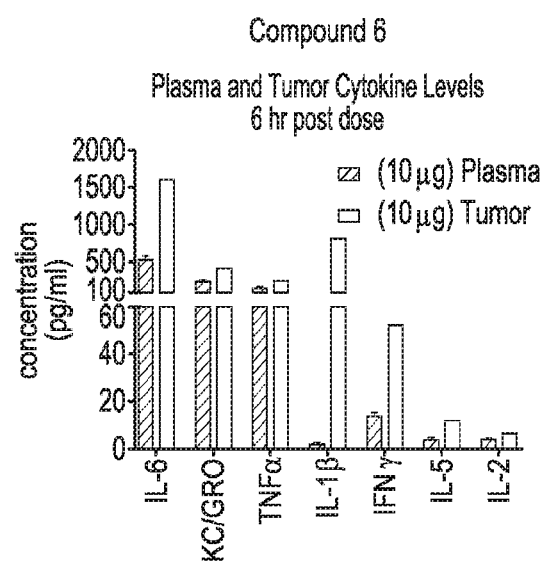

The lower peak induction of systemic cytokines by Compound 6 is shown in FIGS. 6A and 6B. FIGS. 6A and 6B are graphs providing a comparison of tumor and plasma cytokine concentrations at 2 hours and at 6 hours, respectively, following treatment with Compound 6. The concentration of systemic cytokines was significantly less than that in the tumor for each of the cytokines measured (IL-6, KC/GRO, TNF-α, IL-β, IL-5, IFN-α, IFN-γ, IL-2 and IL-12p70).

The Compound 6 dose in these CT26 model conditions showed an optimal cytokine induction profile maximizing intratumoral cytokine induction and minimal induction in blood (FIGS. 6A and 6B). This observation supports the aim of tumor environment-biased engagement of immune cells by intra/peritumorally delivered Compound 6, an illustrative multi-arm polymer conjugate of a TLR 7/8 agonist, reducing risk of excessive systemic immune activation.

Compound 6, a multi-arm polymer conjugate of a TLR 7/8 agonist, dependently induced the plasma cytokines downstream of TLR7 receptor activity in mouse tumors. Intra/peritumoral delivery of the conjugate led to higher levels of TLR7 pathway activation in treated tumors compared to peripheral blood supporting the concept of local intratumorally biased immune activation.

Example 19

Reaction of rIL-2 with mPEG2-C2-Fmoc-20kD-NHS

Purified rIL-2 (106.4 mL) at 1.44 mg/ml was charged into a first vessel followed by the addition of 53.6 mL of formulation buffer (10 mM sodium acetate, pH 4.5, 5% trehalose). The pH was measured at 4.62 the temperature was measured at 21.2° C. The PEG reagent, C2-PEG2-FMOC-NHS-20K (available as described in WO 2006/138572) (13.1 g), was charged into a second vessel followed by the addition of 73.3 mL of 2 mM HCl. The resulting solution was swirled by hand for 25 minutes. Sodium borate (0.5 M, pH 9.8) was added to the first vessel to raise the pH to about 9.1 and then the contents of the second vessel containing the PEG reagent was added to the first vessel over a period of from one to two minutes. A rinse step was then performed by charging 8.1 mL of 2 mM HCl into the second vessel and adding the contents to the first vessel. For the conjugation reaction, the final rIL-2 concentration was 0.6 mg/mL, the sodium borate concentration was 120 mM, the pH was 9.1+/−0.2, the temperature was 20-22° C., and the molar ratio of PEG reagent to rIL-2, after adjustment for activity of the reagent (substitution level) was 35:1. The conjugation reaction was allowed to proceed for thirty minutes and quenched by acidification by addition of 75 mL of 2N acetic acid (to bring the pH down to approximately to 4). The product was purified by ion exchange chromatography as previously described to provide a composition of primarily 4-mers, 5-mers and 6-mers (referring to the number of PEG reagents releasably covalently attached to r-IL-2 (wherein 8-mers and higher degrees of PEGylation were removed during a washing step associated with chromatography). This composition is referred to herein as "RSLAIL-2".

Example 20

Receptor-Bias of RSLAIL-2 and Related Immunotherapeutic Properties

Binding Affinity to IL-2 Receptors and Receptor Bias Related to Immunostimulatory Profile: The affinity of RSLAIL-2 to IL-2Rα and IL-2Rβ was measured directly by surface plasmon resonance (Biacore T-100) and compared to that of clinically available IL-2 (aldesleukin). Antihuman antibody (Invitrogen) was coupled to the surface of a CM-5 sensor chip using EDC/NHS chemistry. Then either human IL-2Rα-Fc or IL-2Rβ-Fc fusion protein was used as the captured ligand over this surface. Serial dilutions of RSLAIL-2 and its active IL-2 conjugates metabolites (1-PEG- and 2-PEG-IL-2) were made in acetate buffer pH 4.5, starting at 5 mM. These dilutions were allowed to bind to the ligands for 5 minutes, and the response units (RU) bound was plotted against concentration to determine EC50 values. The affinities of each isoform to each IL-2 receptor subtype were calculated as fold change relative to those of IL-2.

The in vitro binding and activation profiles of RSLAIL-2 suggested that PEGylation interferes with the interaction between IL2 and IL2Rα relative to aldesleukin; an investigation was carried out to determine whether these effects bias the profile of immune cell subtypes in vivo. The number of CD8 T and Treg cells in a tumor following administration of either RSLAIL-2 or IL2 is an important measure of whether pleiotropic effects of IL2 have been shifted due to conjugation of IL2 to poly(ethylene glycol) (as in RSLAIL-2) at the IL2/IL2Rα interface. To address the question, mice bearing subcutaneous B16F10 mouse melanoma tumors were treated with a single dose of RSLAIL-2 or 5 doses of aldesleukin, and immune cells in the tumor microenvironment were quantified by flow cytometry.

In tumors of aldesleukin-treated mice, total and memory CD8 cells were increased as a percentage of tumor-infiltrating lymphocytes; however, these effects were transient, reaching significance relative to vehicle on day 5. In contrast, significant (P<0.05) and sustained total and memory CD8 T-cell stimulation was achieved following a single RSLAIL-2 administration, with superior percentages of memory CD8 (day 7) and total CD8 (days 7 and 10) relative to aldesleukin. Both RSLAIL-2 and aldesleukin treatment resulted in increased activated natural killer (NK) cells 5 and 7 days after treatment initiation, though this effect was diminished by day 10. CD4 cell percentages of tumor-infiltrating lymphocytes were diminished following RSLAIL-2 treatment relative to vehicle on day 5. On day 10, RSLAIL-2 resulted in fewer CD4 cell percentages compared with vehicle and aldesleukin. The CD4 cell population was further analyzed for the FoxP3$^+$ subset, which defines the Treg population. RSLAIL-2 administration reduced percentage of Tregs at every time point, consistent with reduced access to the IL2Rα subunit arising from the PEG chains. In contrast, Treg reduction with aldesleukin was modest achieving significance on day 5. The increase of CD8 T cells and reduction of Tregs led to a marked elevation of the CD8/Treg ratio in the tumor by day 7. The ratio of CD8/Treg for RSLAIL-2, aldesleukin, and vehicle was 449, 18, and 4, respectively, supporting preferential activation of the IL2 receptor beta over IL2 receptor alpha for RSLAIL-2.

Immunohistochemical staining was performed and confirmed that CD8 T cells were not only increased in number but were interspersed with tumor cells. These results indicate RSLAIL-2 is effective to induce a more robust in vivo memory effector CD8 T-cell response than seen with unmodified IL-2 (aldesleukin), without a commensurate stimulation of Tregs in tumor, consistent with an in vitro IL2I0-biased binding profile. That is to say, RSLAIL-2 is effective to preferentially activate and expand effector CD8+ T- and NK-cells over Tregs.

Example 21

In Vivo Study: Administration of RSLAIL-2 and 4-arm-PEG20k-CM-N—R848 in a Murine CT-26 Colon Tumor Model Studies were conducted to evaluate and compare the antitumor response of a combination of an illustrative long acting IL-2Rβ-biased agonist, RSLAIL-2, and an exemplary long-acting TLR agonist, 4-arm-PEG20k-CM-N—R848, in a murine CT-26 colon tumor model when compared to immunotherapy with each of the single agents, RSLAIL-2 and 4-arm-PEG20k-CM-N—R848.

In vivo model: Mice used were ~10 weeks old female Balb/c strain with 2 million CT26 tumor cells implanted on each flank. Cells were allowed to mature into tumors for 9 days reaching a volume of 100-150 mm³ volume.

Dosing: 4-arm-PEG20k-CM-N—R848 was dosed in 40 μl volume intra- or peritumorally (i.e., directly) to one of the two tumors (primary tumor). Secondary, the contralateral side tumor was not treated directly with the TLR agonist, 4-arm-PEG20k-CM-N—R848. RSLAIL-2 was dosed systemically by intravenous injection at 0.8 mg/kg.

Group labeled: "RSLAIL-2+4-arm-PEG20k-CM-N—R848": mice were dosed intra-/peritumorally with 800 μg of 4arm-20kPEG-CM-N-R848 on the first dosing day (dosing day 0) at a tumor size 100-150 mm³. The same mice were also dosed intravenously with RSLAIL-2 at a dose of 0.8 mg/kg on days 0, 9 and 18 (i.e., they were dosed every 9 days, for a total of 3 doses, starting on dosing day 0).

Group labeled "4-arm-PEG20k-CM-N—R848": mice were dosed intra-/peritumorally with 800 μg of 4arm-20kPEG-CM-N-R848 once on the first dosing day (dosing day 0) at a tumor size ranging from 100-150 mm³.

Group labeled "RSLAIL-2": mice were also dosed intravenously with 0.8 mg/kg RSLAIL-2 on days 0, 9 and 18 (every 9 days for a total of three doses, starting on dosing day 0).

Group labeled "vehicle": mice were dosed intra-/peritumorally with 40 μl Hank's buffered saline (vehicle of 4-arm-PEG20k-CM-N—R848) on the first dosing day (dosing day 0) at tumor size ranging from 100-150 mm³. Same mice were also dosed intravenously with RSLAIL-2 vehicle on days 0, 9 and 18 (every 9 days for a total of 3 doses, starting on dosing day 0).

Measurements: Tumor volumes were collected by caliper measurements 3 times per week and calculated using formula: L×W²/2 where L is tumor length and W is tumor width.

Results are provided in Table 4.

TABLE 4

Survival Proportions, In Percent

| Days after treatment start | Vehicle i.t. | 1 × 800 μg 4-arm-PEG20k-CM-N-R848 i.t. + RSLAIL-2 i.v. "Combo" | Single agent 1 × 800 μg 4-arm-PEG20k-CM-N-R848 i.t. | Single agent RSLAIL-2 |
|---|---|---|---|---|
| 0 | 100 | 100 | 100 | 100 |
| 9 | 90 | | | 90 |
| 12 | 50 | | 80 | |
| 14 | 20 | | | |
| 16 | 0 | | 70 | |
| 19 | | | 40 | |
| 21 | | | 30 | |
| 26 | | | | 70 |
| 40 | | | | 60 |
| 43 | | | | 40 |
| 47 | | 100 | 30 | 30 |

Single agent treatment with 4-arm-PEG20k-CM-N—R848 leads to survival of only 30% of the animals by the end of the experiment at day 47 after dosing start. Only 20% of the animals had a complete response, both treated and untreated side tumors were eliminated; 10% of the animals had a partial response with one of the two tumors eradicated.

Single agent treatment with RSLAIL-2 resulted in survival of 30% of the animals by the end of the study at day 47 after commencement of dosing. All animals in the surviving group had complete responses, both tumors eliminated.

Most notably, combination treatment with RSLAIL-2+4-arm-PEG20k-CM-N—R848 resulted in complete elimination of tumors in all treated animals and 100% survival. Strikingly, both the primary and secondary tumors were eliminated over the course of treatment. See FIGS. 1-3. That is to say, unexpectedly, the combination treatment resulted not only in a significant improvement over the single agent immunotherapeutic treatment modalities, e.g., 4-arm-PEG20k-CM-N—R848 (30% survival at day 47); RSLAIL-2 (30% survival at day 47) versus combination immunotherapy at 100% survival to at least day 47, but also resulted in the complete eradication of both the primary tumor (injected with the TLR agonist) and the secondary tumor (no direct injection of TLR agonist, site remove from site of primary tumor).

The vehicle group had no surviving animals. All animals were removed from study due to reaching limiting tumor volume between days 10 and 20 after treatment start.

The results are striking for the combination when compared to monotherapy with each of the immunomodulators administered singly—that is, the combined administration of RSLAIL-2+4-arm-PEG20k-CM-N—R848 was effective to eradicate not only the primary CT-26 colon tumor to which 4-arm-PEG20k-CM-N—R848 was directly administered by injection, but was also effective to eradicate the secondary CT-26 colon tumor. No tumor regrowth was observed over the course of the study, 47 days. Moreover, survival remained at 100 percent for the combination therapy group, while by day 47, both of the monotherapy groups were reduced to 30% survival.

Figure 2:
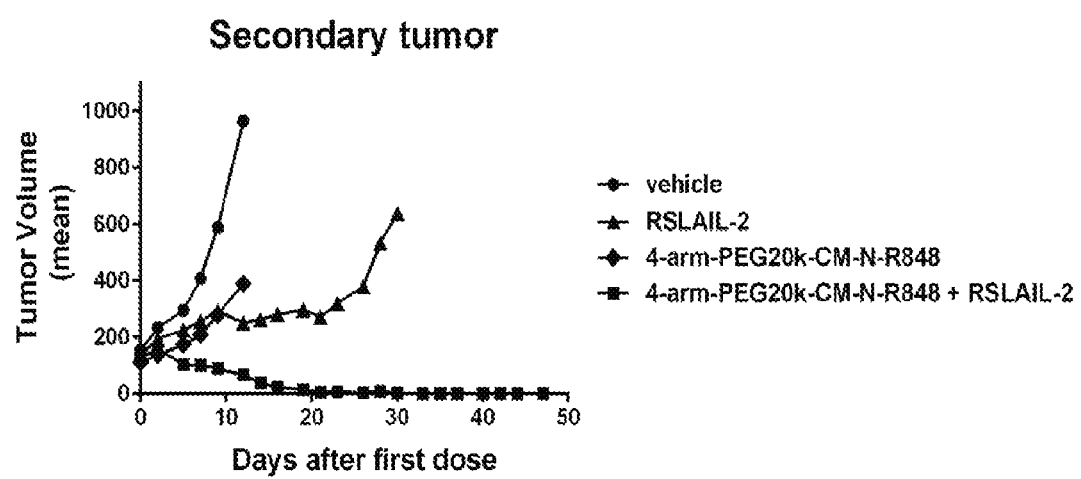
FIG. 2 is a plot showing secondary tumor (remote, non-TLR agonist injection site) volume versus days following initial dosing of mice treated with various interventions in a mouse colon carcinoma model (CT-26) as described in detail in Example 21.
Figure 3:
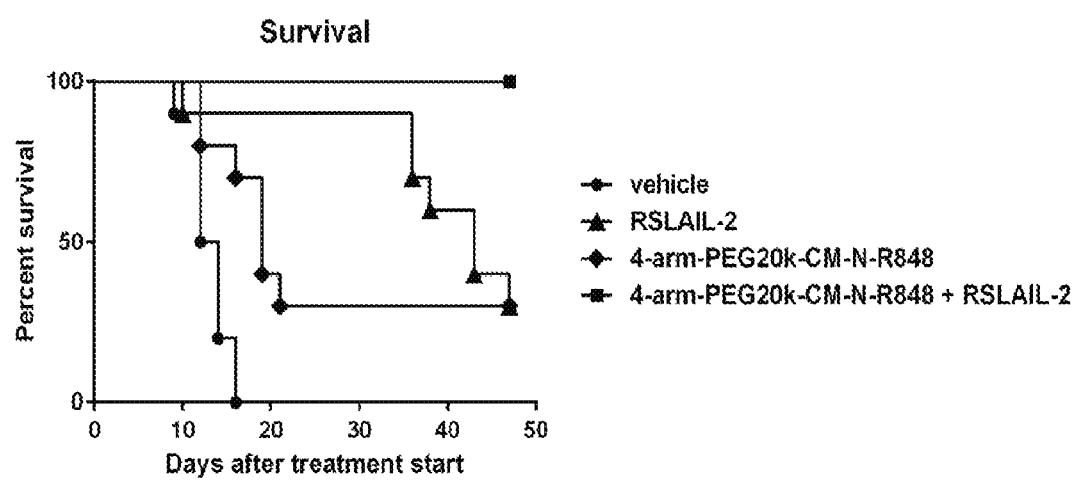
FIG. 3 is a plot of percent survival versus days following initial dosing for mice treated with various interventions (vehicle, exemplary long acting IL-2Rβ-biased agonist, RSLAIL-2; an exemplary TLR agonist, 4-arm-PEG20k-CM-N—R848; and a combination of RSLAIL-2 and 4-arm-PEG20k-CM-N—R848) in a mouse colon carcinoma model (CT-26) as described in detail in Example 21.
Figure 4A:
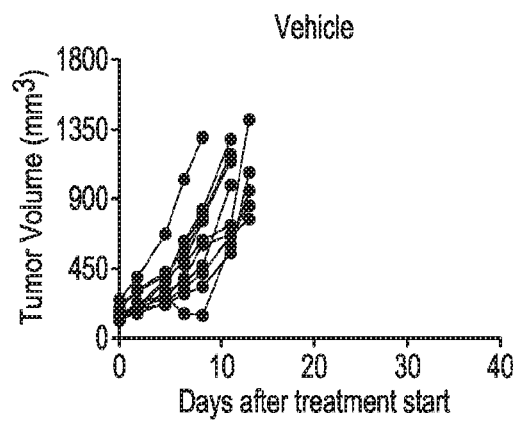
FIGS. 4A-4D are plots showing that that combination treatment with RSLAIL-2 and R848 leads to decreased or maintained tumor volume of the treated tumor for nine of the ten animals in the high dosage group, seven of the ten animals in the mid dosage group, and only one of the eight animals in the low dosage group by day 25 after treatment start, as described in detail in Example 23.
Figure 4B:
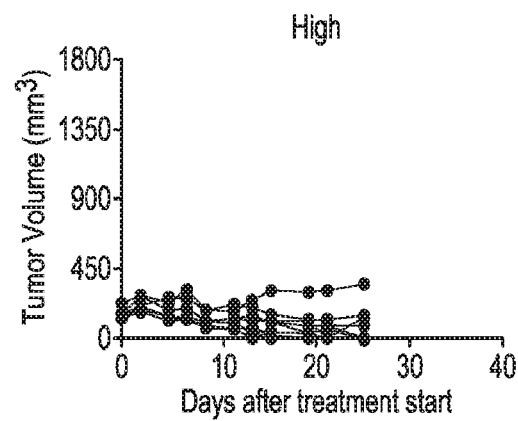
Figure 4C:
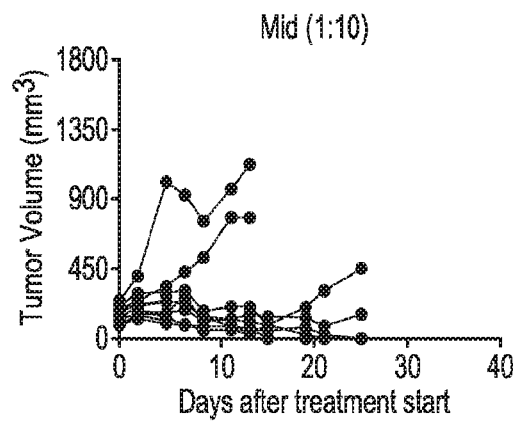
Figure 4D:
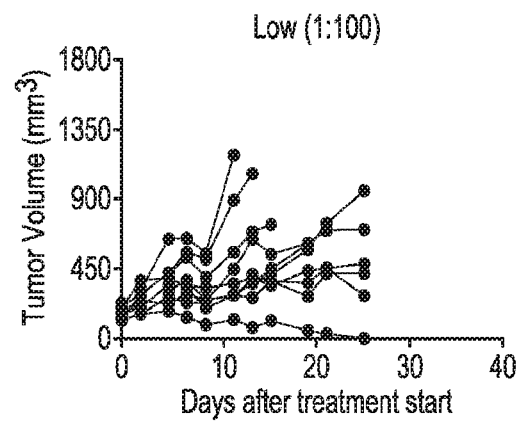
Figure 4E:
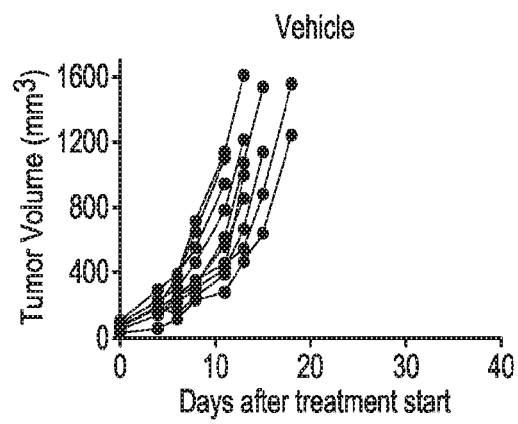
FIGS. 4E-4H are plots showing that combination treatment with RSLAIL-2 and Compound 6 leads to decreased or maintained tumor volume of the treated tumor for nine of the ten animals in the high dosage group, nine of the ten animals in the mid dosage group, and (surprisingly) ten of the ten animals in the low dosage group by day 32 after treatment start, as described in detail in Example 23.
Figure 4F:
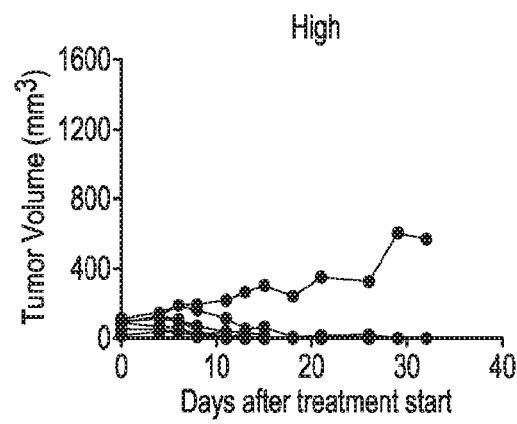
Figure 4G:
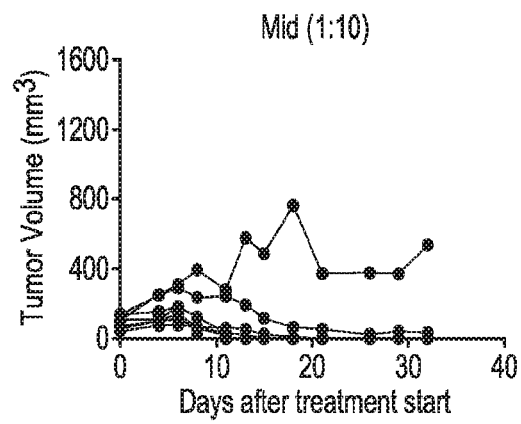
Figure 4H:
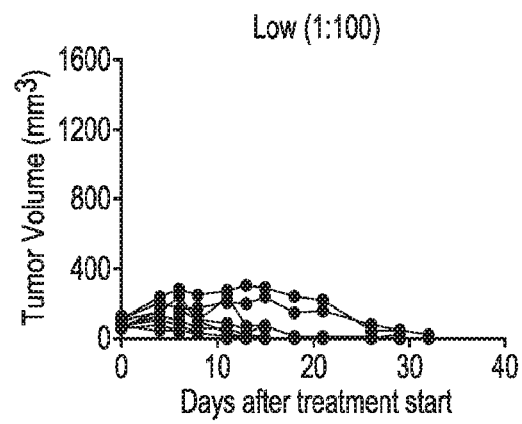
Figure 5A:
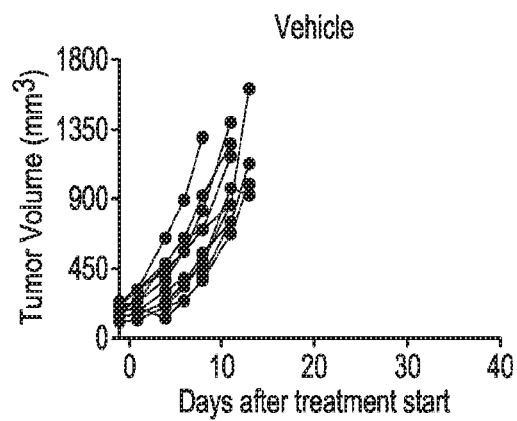
FIGS. 5A-5D are plots showing that combination treatment with RSLAIL-2 and R848 leads to decreased or maintained tumor volume of the non-treated tumor for nine of the ten animals in the high dosage group, five of the ten animals in the mid dosage group, and only one of the eight animals in the low dosage group by day 25 after treatment start, as described in detail in Example 23.
Figure 5B:
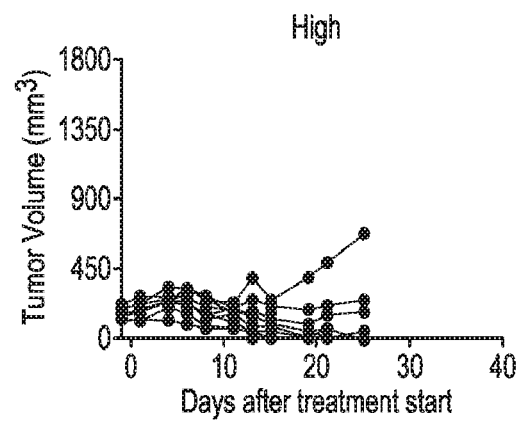
Figure 5C:
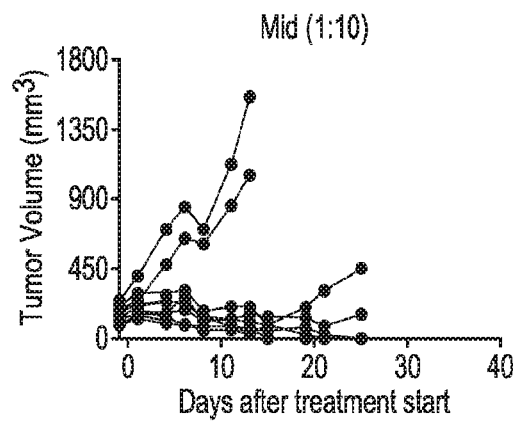
Figure 5D:
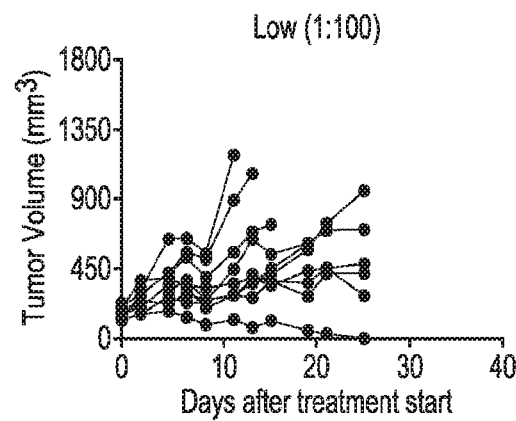
Figure 5E:
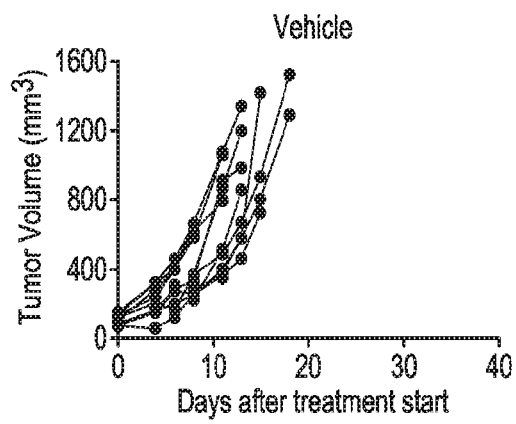
FIGS. 5E-5H are plots showing that combination treatment with RSLAIL-2 and Compound 6 leads to decreased or maintained tumor volume of the non-treated tumor for nine of the ten animals in the high dosage group, eight of the ten animals in the mid dosage group, and (surprisingly) ten of the ten animals in the low dosage group by day 32 after treatment start, as described in detail in Example 23.
Figure 5F:
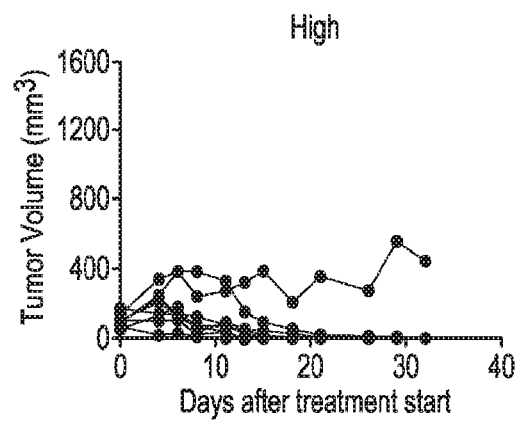
Figure 5G:
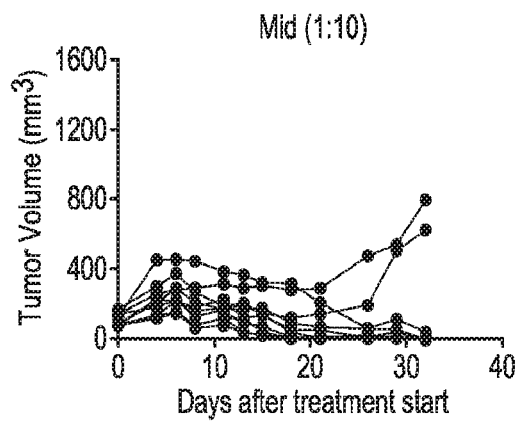
Figure 5H:
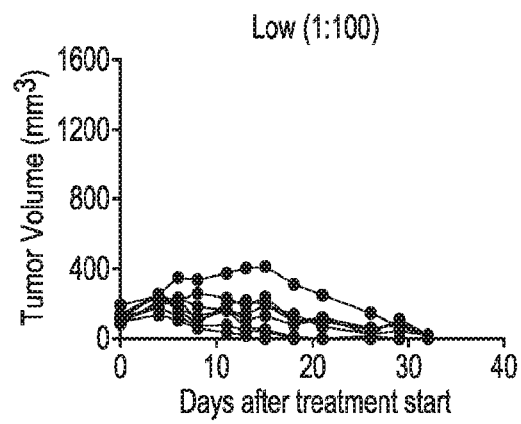

Results are shown in FIGS. 1-3.

Example 22

Effect of Treatment In Vivo on Immune Cell Types

This example shows that the combination of a long acting IL-2Rβ-biased agonist and a TLR7/8 agonist can promote activation of the immune system, while also overcoming immune suppression. Specifically, immune activation is shown through promotion of CD8 T cells, CD11c+ and CD8+ dendritic cells, and neutrophils, while overcoming immune suppression is shown through suppression of T regulatory cells, macrophages, and monocytes.

Female Balb/c mice used were about 10 weeks old with two million CT26 tumor cells implanted on each flank. Cells were allowed to grow for nine days, reaching tumor sizes from 100-150 mm³ in volume.

R848 was dosed in 40 μl volume intra- or peri-tumorally to one of the tumors (primary tumor). The other (contralateral) tumor was not dosed with R848.

RSLAIL-2 was dosed systemically by intravenous injection at 0.8 mg/kg.

Immune cell subtypes were measured by flow cytometry. Tumors were dissociated into single cell suspensions and cells were stained with cell type identifying combinations of fluorescently labeled antibodies to evaluate intra-tumoral immune cell type proportional changes including monocytes, macrophages, regulatory T cells, CD8+ T cells, neutrophils, and dendritic cells subtypes in response to RSLAIL-2 and R848 treatment as single agents and in combination.

Results are provided in Table 5 as percent cell population with respect to the vehicle control group.

TABLE 5

In Vivo Effect of Single Agents and Combination on Immune Cell Types (Percent of Vehicle)

|  | RSLAIL-2 | R848 | RSLAIL-2 & R848 |
| --- | --- | --- | --- |
| CD8 T Cells | 200% | 95% | 265% |
| CD11c+ CD8+ Dendritic Cells | 165% | 135% | 330% |
| Neutrophils | 225% | 500% | 525% |
| T Regulatory Cells | 125% | 20% | 30% |
| Macrophages | 85% | 80% | 50% |
| Monocytes | 20% | 160% | 50% |

As can be seen from the data in Table 5, single agent treatment with R848 or combination treatment with R848 and RSLAIL-2 leads to: (i) reduction of regulatory T cell abundance in tumors; and (ii) an increase in neutrophil abundance relative to vehicle-treated tumors.

Single agent treatment with RSLAIL-2 leads to reduction of intratumoral monocytes and an increase in CD8 T cells relative to vehicle-treated tumors.

In considering the combination, treatment with RSLAIL-2 and R848 (an exemplary TLR agonist) leads to an enhanced effect of combining the above mentioned single agent effects on intratumoral immune cell abundance. Additionally, the combination specifically increases CD8+ CD11c+ dendritic cells and reduces macrophages in treated tumors when compared to vehicle treatment.

All cellular changes in the combination treatment with RSLAIL-2 are observed not only in R848 treated tumors, but also in distal tumors that are not treated directly with R848 but reside in the same animal as the R848 treated tumor (i.e., demonstrating an abscopal effect).

Example 23

In Vivo Study: Administration of RSLAIL-2 and a TLR Agonist in a CT26 Tumor Model Studies were conducted to evaluate and compare the antitumor response of a combination of an illustrative long acting IL-2Rβ-biased agonist, RSLAIL-2, and a short-acting TLR agonist (R848) or an exemplary long-acting TLR agonist (Compound 6), in a CT26 tumor model over a range of TLR agonists dosages.

Mice used were ~10 weeks old female Balb/c strain with 2 million CT26 tumor cells implanted on each flank. Cells were allowed to mature into tumors for 7 days for treatment with RSLAIL-2 and Compound 6 combination, and for 9 days for RSLAIL-2 and R848 combination treatment, reaching a volume of 100-150 mm³ for each treatment group. Each treatment group contained 10 mice.

The TLR agonist (R848 or Compound 6) was dosed in 40 μl volume intra- or peritumorally (i.e., directly) to one of the two tumors (primary tumor) at 10 micrograms ("high"), 1 microgram ("mid"), or 0.1 micrograms ("low") (R848 equivalent) fixed dose. The contralateral side tumor was not treated directly with the TLR agonist. RSLAIL-2 was dosed systemically by intravenous injection at 0.8 mg/kg.

Mice were dosed intra-/peritumorally with 10 micrograms, 1 microgram, or 0.1 micrograms (R848 equivalent) fixed dose of TLR agonist on the first dosing day (dosing day 0) at a tumor size 100-150 mm³. The same mice were also dosed intravenously with RSLAIL-2 at a dose of 0.8 mg/kg on days 4, 13 and 22 (i.e., they were dosed every 9 days, for a total of 3 doses, starting on dosing day 0).

For the group labeled "vehicle": mice were dosed intra-/peritumorally with 40 μl Hank's buffered saline (vehicle of TLR agonist) on the first dosing day (dosing day 0) at tumor size ranging from 100-150 mm³. The same mice were also dosed intravenously with RSLAIL-2 vehicle on days 0, 9 and 18 (every 9 days for a total of 3 doses, starting on dosing day 0).

Tumor volumes were collected by caliper measurements 2-3 times per week and calculated using formula: $L \times W^2/2$ where L is tumor length and W is tumor width.

Results are provided in FIGS. 4A-4D for combination treatment with RSLAIL-2 and R848 and in FIGS. 4E-H for combination treatment with RSLAIL-2 and Compound 6. Results are also shown in FIGS. 5A-5D for combination treatment with RSLAIL-2 and R848 and in FIGS. 5E-5H for combination treatment with RSLAIL-2 and Compound 6. As provided in FIGS. 4A-4D, combination treatment with RSLAIL-2 and R848 leads to decreased or maintained tumor volume of the treated tumor for nine of the ten animals in the high dosage group, seven of the ten animals in the mid-dosage group, and only one of the eight animals in the low dosage group by day 25 after treatment start.

As provided in FIGS. 4E-4H, combination treatment with RSLAIL-2 and Compound 6 leads to decreased or maintained tumor volume of the treated tumor for nine of the ten animals in the high dosage group, nine of the ten animals in the mid dosage group, and surprisingly, ten of the ten animals in the low dosage group by day 32 after treatment start.

As provided in FIGS. 5A-5D, combination treatment with RSLAIL-2 and R848 leads to decreased or maintained tumor volume of the non-treated tumor for nine of the ten animals in the high dosage group, five of the ten animals in the mid dosage group, and only one of the eight animals in the low dosage group by day 25 after treatment start.

As provided in FIGS. 5E-5H, combination treatment with RSLAIL-2 and Compound 6 leads to decreased or maintained tumor volume of the non-treated tumor for nine of the ten animals in the high dosage group, eight of the ten animals in the mid dosage group, and surprisingly, ten of the ten animals in the low dosage group by day 32 after treatment start.

As provided in FIGS. 4A-4H, and FIGS. 5A-5H, the vehicle groups had no surviving animals by day 25 after treatment start. All animals were removed from the study due to reaching limiting tumor volume between days 8 and 18 after treatment start.

This data indicate that very low sub-microgram amounts of intratumorally delivered TLR agonist Compound 6 in combination with RSLAIL-2 treatment significantly inhibits tumor growth at the treatment site as well as at an untreated abscopal tumor site, i.e., a site in which the TLR agonist compound was not directly administered.

Example 24

In Vivo Study: Administration of RSLAIL-2 and an Exemplary TLR Agonist in a WEHI-164 Tumor Model Studies were conducted to evaluate and compare the antitumor response of a combination of an illustrative long-acting IL-2Rβ-biased agonist, RSLAIL-2, and an exemplary TLR agonist, 4-arm-PEG20k-CM-Gly-N-R848 (Compound 6), in a WEHI-164 fibrosarcoma tumor model when compared to vehicle treatment.

In vivo model: Mice used were ~10 weeks old female Balb/c strain with 1 million WEHI-164 tumor cells implanted subcutaneously on right-side flank. Cells were allowed to grow into tumors reaching a volume of 50-150 mm$^3$ volume prior to treatment start.

Dosing: 4-arm-PEG20k-CM-Gly-N-R848 was dosed in 40 μl volume intra- or peritumorally (i.e., directly) to the tumor. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 50-150 mm$^3$. The same mice were also dosed intravenously with RSLAIL-2 at a dose of 0.8 mg/kg on days 0, 9 and 18 (i.e., they were dosed for a total of 3 doses, 9 days apart).

Group labeled "vehicle": mice were dosed intra-/peritumorally with 40 μl Hank's buffered saline (vehicle of 4-arm-PEG20k-CM-Gly-N-R848) on the first dosing day (dosing day 0) at tumor size ranging from 50-150 mm$^3$. Same mice were also dosed intravenously with RSLAIL-2 vehicle buffer on days 0, 9 and 18, a total of 3 doses that were 9 days apart, starting on dosing day 0.

Measurements: Tumor volumes were collected by caliper measurements 2-3 times per week for 52 days and calculated using formula: L×W$^2$/2 where L is tumor length and W is tumor width.

Data is provided in Table 6.

TABLE 6

| Survival Proportions | | |
|---|---|---|
| Days after treatment start | Vehicle | 4-arm-PEG20k-CM-Gly-N-R848 + RSLAIL-2 |
| 0 | ++++ | ++++ |
| 3 | ++++ | ++++ |
| 7 | ++++ | ++++ |
| 10 | ++++ | ++++ |
| 15 | ++++ | ++++ |
| 22 | +++ | ++++ |
| 27 | +++ | ++++ |
| 29 | ++ | ++++ |
| 31 | + | ++++ |
| 34 | none | ++++ |
| 41 | | ++++ |
| 48 | | ++++ |
| 52 | | ++++ |

Survival percentages are provided as follows:

0%≤+<25%

25%≤++<50%

50%≤+++<75%

75%≤++++<100%

Double agent treatment with RSLAIL-2+4-arm-PEG20k-CM-Gly-N-R848 resulted in survival of 90% of the animals by the end of the study at day 52 after commencement of dosing. Strikingly, 80% of all animals in the RSLAIL-2+4-arm-PEG20k-CM-Gly-N-R848 treatment group had complete responses, meaning no measurable tumors were observed by the end of the study.

The vehicle group had no surviving animals. All animals were removed from study due to reaching limiting tumor volume between days 17 and 31 after treatment start.

Example 25

In Vivo Study: Administration of RSLAIL-2 and TLR Agonist in a JC Tumor Model

Studies were conducted to evaluate and compare the antitumor response of a combination of an illustrative long acting IL-2Rβ-biased agonist, RSLAIL-2, and an exemplary TLR agonist, 4-arm-PEG20k-CM-Gly-N-R848, in a JC mammary adenocarcinoma tumor model when compared to vehicle treatment.

In vivo model: Mice used were ~10 weeks old female Balb/c strain with 4 million JC tumor cells implanted subcutaneously on right-side flank. Cells were allowed to grow into tumors reaching a volume of 50-150 mm$^3$ volume prior to treatment start.

Dosing: 4-arm-PEG20k-CM-Gly-N-R848 was dosed in 40 μl volume intra- or peritumorally (i.e., directly) to the tumor. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 50-150 mm$^3$. The same mice were also dosed intravenously with RSLAIL-2 at a dose of 0.8 mg/kg on days 0, 9 and 18 (i.e., they were dosed for a total of 3 doses, 9 days apart).

Group labeled "vehicle": mice were dosed intra-/peritumorally with 40 μl Hank's buffered saline (vehicle of 4-arm-PEG20k-CM-Gly-N-R848) on the first dosing day (dosing day 0) at tumor size ranging from 50-150 mm$^3$. Same mice were also dosed intravenously with RSLAIL-2 vehicle buffer on days 0, 9 and 18, a total of 3 doses that were 9 days apart, starting on dosing day 0.

Measurements: Tumor volumes were collected by caliper measurements 2-3 times per week for 113 days and calculated using formula: L×W$^2$/2 where L is tumor length and W is tumor width.

Data provided in Table 7.

TABLE 7

| Survival Proportions | | |
|---|---|---|
| Days after treatment start | Vehicle | 4-arm-PEG20k-CM-Gly-N-R848 + RSLAIL-2 |
| 0 | ++++ | ++++ |
| 8 | ++++ | ++++ |
| 15 | ++++ | ++++ |
| 22 | ++++ | ++++ |
| 29 | +++ | ++++ |
| 36 | + | ++++ |
| 43 | none | ++++ |
| 46 | | +++ |
| 50 | | +++ |
| 57 | | ++ |
| 60 | | ++ |
| 64 | | + |
| 71 | | + |
| 78 | | + |
| 85 | | + |
| 95 | | + |
| 102 | | + |
| 113 | | + |

Survival percentages are provided as follows:

0%≤+<25%

25%≤++<50%

50%≤+++<75%

75%≤++++<100%

Double agent treatment (i.e., combination therapy) with RSLAIL-2 and 4-arm-PEG20k-CM-Gly-N-R848 (Compound 6) resulted in survival of 90% of the animals by day 43, while no surviving animals were remaining in the vehicle group by day 43. RSLAIL-2+4-arm-PEG20k-CM-Gly-N-R848 combination treatment led to 20% of the animals surviving by the end of the study at day 113 after commencement of dosing. Strikingly, 10% of animals in the RSLAIL-2+4-arm-PEG20k-CM-Gly-N-R848 treatment group had complete responses, meaning that no measurable tumors were observed by the end of the study.

The vehicle group had no surviving animals. All animals were removed from study due to reaching limiting tumor volume between days 26 and 36 after treatment start.

Example 26

In Vivo Study: Administration of RSLAIL-2 and TLR Agonist in a 4T1 Tumor Model

Studies were conducted to evaluate and compare the antitumor response of a combination of an illustrative long acting IL-2Rβ-biased agonist, RSLAIL-2, and an exemplary TLR agonist, 4-arm-PEG20k-CM-Gly-N-R848, in a subcutaneous 4T1 mammary carcinoma tumor model when compared to immunotherapy with the single agent RSLAIL-2 and the single agent TLR agonist (comparative monotherapies).

In vivo model: Mice used were ~10 weeks old female Balb/c strain with 2 million 4T1 tumor cells implanted on each flank. Cells were allowed to mature into tumors for 7 days reaching a volume of 75-150 mm³ volume.

Dosing: 4-arm-PEG20k-CM-Gly-N-R848 was dosed in 40 μl volume intra- or peritumorally (i.e., directly) to one of the two tumors (primary tumor). Secondary, the contralateral side tumor was not treated directly with the TLR agonist, 4-arm-PEG20k-CM-Gly-N-R848. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 75-150 mm³. The same mice were also dosed intravenously with RSLAIL-2 at a dose of 0.8 mg/kg on days 0, 9 and 18 (i.e., they were dosed for a total of 3 doses, 9 days apart, starting on dosing day 0).

Group labeled "vehicle": mice were dosed intra-/peritumorally with 40 μl Hank's buffered saline (vehicle of 4-arm-PEG20k-CM-Gly-N-R848) on the first dosing day (dosing day 0) at tumor size ranging from 75-150 mm³.

Measurements: Tumor volumes were collected by caliper measurements 2-3 times per week and calculated using formula: L×W²/2 where L is tumor length and W is tumor width.

Results: Data is provided in Table 8. The results are notable for the doublet combination when compared to vehicle treatments—that is, the doublet combined administration of RSLAIL-2 and 4-arm-PEG20k-CM-Gly-N-R848 was effective to slow tumor growth not only in the primary tumor to which 4-arm-PEG20k-CM-Gly-N-R848 was directly administered by injection, but was also effective to slow secondary tumor growth. Survival remained at 30% percent for the doublet combination therapy group of RSLAIL-2 and 4-arm-PEG20k-CM-Gly-N-R848 by the end of the study at day 25, while no surviving animals were remaining in the vehicle treatment group after day 18 of the study.

TABLE 8

| | Survival Proportions | |
| --- | --- | --- |
| Days after treatment start | Vehicle | 4-arm-PEG20k-CM-Gly-N-R848 + RSLAIL-2 |
| 0 | ++++ | ++++ |
| 3 | ++++ | ++++ |
| 7 | ++++ | ++++ |
| 9 | ++++ | ++++ |
| 11 | ++++ | ++++ |
| 14 | ++++ | ++++ |
| 16 | +++ | ++++ |
| 18 | +++ | ++++ |
| 21 | none | +++ |
| 23 | | +++ |
| 25 | | ++ |

Survival percentages are provided as follows:
0%≤+<25%
25%≤++<50%
50%≤+++<75%
75%≤++++<100%

Double immunotherapeutic agent treatment with RSLAIL-2+4-arm-PEG20k-CM-Gly-N-R848 resulted in survival of 30% of the animals by the end of the study at day 25 after commencement of dosing. The combination treatment with RSLAIL-2+4-arm-PEG20k-CM-Gly-N-R848 showed significant improvement over the vehicle treatment by slowing tumor growth in treated animals.

The vehicle group had no surviving animals by end of study at day 25. All animals were removed from study due to reaching limiting tumor volume between days 16 and 18 after treatment start.

Example 27

In Vivo Study: Administration of RSLAIL-2 and TLR Agonist in a MC38 Tumor Model

Studies were conducted to evaluate and compare the antitumor response of a combination of an illustrative long acting IL-2Rβ-biased agonist, RSLAIL-2, and an exemplary multi-armed polymer conjugate of a TLR 7/8 agonist, 4-arm-PEG20k-CM-Gly-N-R848, in a MC38 colon carcinoma tumor model when compared to vehicle treatment.

In vivo model: Mice used were ~10 weeks old female Balb/c strain with 0.25 million MC38 tumor cells implanted subcutaneously on right-side flank. Cells were allowed to grow into tumors reaching a volume of 50-150 mm³ volume prior to treatment start.

Dosing: 4-arm-PEG20k-CM-Gly-N-R848 was dosed in 40 μl volume intra- or peritumorally (i.e., directly) to the tumor. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 50-150 mm³. The same mice were also dosed intravenously with RSLAIL-2 at a dose of 0.8 mg/kg on days 0, 9 and 18 (i.e., they were dosed for a total of 3 doses, 9 days apart).

Group labeled "vehicle": mice were dosed intra-/peritumorally with 40 μl Hank's buffered saline (vehicle of 4-arm-PEG20k-CM-Gly-N-R848) on the first dosing day (dosing day 0) at tumor size ranging from 50-150 mm³. Same mice were also dosed intravenously with RSLAIL-2 vehicle buffer on days 0, 9 and 18, a total of 3 doses that were 9 days apart, starting on dosing day 0.

Measurements: Tumor volumes were collected by caliper measurements 2-3 times per week for 70 days and calculated using formula: L×W²/2 where L is tumor length and W is tumor width.

Results: Data is provided in Table 9.

TABLE 9

Survival Proportions

| Days after treatment start | Vehicle | 4-arm-PEG20k-CM-Gly-N-R848 + RSLAIL-2 |
|---|---|---|
| 0 | ++++ | ++++ |
| 3 | ++++ | ++++ |
| 7 | ++++ | ++++ |
| 14 | +++ | ++++ |
| 17 | +++ | ++++ |
| 21 | ++ | +++ |
| 28 | ++ | +++ |
| 35 | + | +++ |
| 39 | + | +++ |
| 42 | none | +++ |
| 49 | | +++ |
| 56 | | +++ |
| 63 | | +++ |
| 70 | | +++ |

Survival percentages are provided as follows:
0%≤+<25%
25%≤++<50%
50%≤+++<75%
75%≤++++<100%

Double agent treatment with RSLAIL-2+4-arm-PEG20k-CM-Gly-N-R848 resulted in survival of 50% of the animals by the end of the study at day 70 after commencement of dosing. Significantly, all surviving animals in the RSLAIL-2+4-arm-PEG20k-CM-Gly-N-R848 treatment group had complete responses, meaning no measurable tumors were observed by the end of the study.

The vehicle group had no surviving animals. All animals were removed from study due to reaching limiting tumor volume between days 7 and 39 after treatment start.

Example 28

In Vivo Study: Administration of RSLAIL-2 and TLR Agonist in an EMT6 Tumor Model Studies were conducted to evaluate and compare the antitumor response of a combination of an illustrative long acting IL-2Rβ-biased agonist, RSLAIL-2, and an exemplary long-acting TLR agonist, 4-arm-PEG20k-CM-Gly-N-R848, in a subcutaneous EMT6 mammary carcinoma tumor model when compared to immunotherapy with the single agent RSLAIL-2 and the single agent TLR agonist.

In vivo model: Mice used were ~10 weeks old female Balb/c strain with 2 million EMT6 tumor cells implanted on each flank. Cells were allowed to mature into tumors for 7 days reaching a volume of 75-150 mm³ volume.

Dosing: 4-arm-PEG20k-CM-Gly-N-R848 was dosed in 40 μl volume intra- or peritumorally (i.e., directly) to one of the two tumors (primary tumor). Secondary, the contralateral side tumor was not treated directly with the TLR agonist, 4-arm-PEG20k-CM-Gly-N-R848. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 75-150 mm³. The same mice were also dosed intravenously with RSLAIL-2 at a dose of 0.8 mg/kg on days 0, 9 and 18 (i.e., they were dosed for a total of 3 doses, 9 days apart, starting on dosing day 0).

Group labeled "RSLAIL-2": mice were also dosed intravenously with RSLAIL-2 at a dose of 0.8 mg/kg on days 0, 9 and 18 (i.e., they were dosed for a total of 3 doses, 9 days apart, starting on dosing day 0).

Group labeled "4-arm-PEG20k-CM-Gly-N-R848": mice were dosed intra-/peritumorally with 20 μg of 4arm-20kPEG-CM-Gly-N-R848 on the first dosing day (dosing day 0) at a tumor size 75-150 mm³.

Group labeled "vehicle": mice were dosed intra-/peritumorally with 40 μl Hank's buffered saline (vehicle of 4-arm-PEG20k-CM-Gly-N-R848) on the first dosing day (dosing day 0) at tumor size ranging from 75-150 mm³.

Measurements: Tumor volumes were collected by caliper measurements 2-3 times per week and calculated using formula: L×W²/2 where L is tumor length and W is tumor width.

Results: Data is provided in Table 10. The results are dramatic for the doublet combination when compared to the poorly efficacious RSLAIL-2 and 4-arm-PEG20k-CM-Gly-N-R848 single agent treatments—that is, the doublet combined administration of RSLAIL-2 and 4-arm-PEG20k-CM-Gly-N-R848 was effective to eradicate not only the primary tumor to which 4-arm-PEG20k-CM-Gly-N-R848 was directly administered by injection, but was also effective to eradicate the secondary tumor. No tumor regrowth was observed over the course of 21 days after complete tumor regressions. Moreover, survival remained at 100% percent for the doublet combination therapy group, while by the end of the study at day 55 no surviving animals were remaining in the single agent treatment groups.

TABLE 10

Survival Proportions

| Days after treatment start | Vehicle | 4-arm-PEG20k-CM-Gly-N-R848 + RSLAIL-2 | 4-arm-PEG20k-CM-Gly-N-R848 | RSLAIL-2 |
|---|---|---|---|---|
| 0 | ++++ | ++++ | ++++ | ++++ |
| 3 | ++++ | ++++ | ++++ | ++++ |
| 8 | ++++ | ++++ | ++++ | ++++ |
| 13 | ++++ | ++++ | ++++ | ++++ |
| 15 | + | ++++ | ++++ | ++++ |
| 20 | none | ++++ | +++ | +++ |
| 27 | | ++++ | ++ | ++ |
| 34 | | ++++ | + | + |
| 42 | | ++++ | + | + |
| 48 | | ++++ | + | none |
| 55 | | ++++ | none | |

Survival percentages are provided as follows:
0%≤+<25%
25%≤++<50%
50%≤+++<75%
75%≤++++<100%

Single agent treatment with RSLAIL-2 or 4-arm-PEG20k-CM-Gly-N-R848 resulted in partial control of tumor growth but no surviving animals by the end of the study at day 55 after commencement of dosing.

In contrast, double agent treatment with RSLAIL-2+4-arm-PEG20k-CM-Gly-N-R848 resulted in survival of 100% of the animals by the end of the study at day 55 after commencement of dosing. All animals in the surviving group had complete responses, both tumors eliminated. That is to say, unexpectedly, the combination treatment with RSLAIL-2+4-arm-PEG20k-CM-Gly-N-R848 not only is a significant improvement over the equivalent dose RSLAIL-2 or 4-arm-PEG20k-CM-Gly-N-R848 immunotherapeutic treatment modalities, but also resulted in the complete eradication of both the primary tumor (injected with the TLR agonist) and the secondary tumor (no direct injection of TLR agonist, removed from site of primary tumor).

The vehicle group had no surviving animals. All animals were removed from study due to reaching limiting tumor volume between days 13 and 15 after treatment start.

Example 29

In Vivo Study: Administration of RSLAIL-2 and TLR Agonist in a RM-1 Tumor Model

Studies were conducted to evaluate and compare the antitumor response of a combination of an illustrative long acting IL-2Rβ-biased agonist, RSLAIL-2, and an exemplary long-acting TLR agonist, 4-arm-PEG20k-CM-Gly-N-R848, in a RM-1 prostate carcinoma tumor model when compared to vehicle treatment.

In vivo model: Mice used were ~10 weeks old female Balb/c strain with 2 million RM-1 tumor cells implanted subcutaneously on right-side flank. Cells were allowed to grow into tumors reaching a volume of 50-150 mm³ volume prior to treatment start.

Dosing: 4-arm-PEG20k-CM-Gly-N-R848 was dosed in 40 µl volume intra- or peritumorally (i.e., directly) to the tumor. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 µg of 4arm-20kPEG-CM-Gly-N-R848 on the first dosing day (dosing day 0) at a tumor size 50-150 mm³. The same mice were also dosed intravenously with RSLAIL-2 at a dose of 0.8 mg/kg on days 0, 9 and 18 (i.e., they were dosed for a total of 3 doses, 9 days apart).

Group labeled "vehicle": mice were dosed intra-/peritumorally with 40 µl Hank's buffered saline (vehicle of 4-arm-PEG20k-CM-Gly-N-R848) on the first dosing day (dosing day 0) at tumor size ranging from 50-150 mm³. Same mice were also dosed intravenously with RSLAIL-2 vehicle buffer on days 0, 9 and 18, a total of 3 doses that were 9 days apart, starting on dosing day 0.

Measurements: Tumor volumes were collected by caliper measurements 2-3 times per week for 36 days and calculated using formula: L×W²/2 where L is tumor length and W is tumor width.

Results: Data is provided in Table 11.

TABLE 11

| Survival Proportions | | |
| --- | --- | --- |
| Days after treatment start | Vehicle | 4-arm-PEG20k-CM-Gly-N-R848 + RSLAIL-2 |
| 0 | ++++ | ++++ |
| 6 | ++++ | ++++ |
| 13 | ++++ | ++++ |
| 18 | + | +++ |
| 20 | none | +++ |
| 25 | | +++ |
| 29 | | ++ |
| 36 | | + |

Survival percentages are provided as follows:
0%≤+<25%
25%≤++<50%
50%≤+++<75%
75%≤++++<100%

Double agent treatment with RSLAIL-2+4-arm-PEG20k-CM-Gly-N-R848 resulted in significantly reduced tumor growth compared to vehicle treatment resulting in survival of 80% of the animals by 20 days after treatment commencement and 10% of animals by the end of study on day 36 in the RSLAIL-2+4-arm-PEG20k-CM-Gly-N-R848 treatment group.

The vehicle group had no surviving animals by day 20 after treatment start. All animals were removed from study due to reaching limiting tumor volume between days 13 and 18 after treatment start.

Example 30

In Vivo Study: Administration of RSLAIL-2 and TLR Agonist in a H22 Tumor Model

Studies were conducted to evaluate and compare the antitumor response of a combination of an illustrative long acting IL-2Rβ-biased agonist, RSLAIL-2, and an exemplary long-acting TLR agonist, 4-arm-PEG20k-CM-Gly-N-N-R848, in a H22 hepatocellular carcinoma tumor model when compared to vehicle treatment.

In vivo model: Mice used were ~10 weeks old female Balb/c strain with 3 million H22 tumor cells implanted subcutaneously on right-side flank. Cells were allowed to grow into tumors reaching a volume of 50-150 mm³ volume prior to treatment start.

Dosing: 4-arm-PEG20k-CM-Gly-N-R848 was dosed in 40 µl volume intra- or peritumorally (i.e., directly) to the tumor. RSLAIL-2 was dosed systemically by intravenous injection at 0.8 mg/kg.

Group labeled: "RSLAIL-2+4-arm-PEG20k-CM-Gly-N-R848": mice were dosed intra-/peritumorally with 20 µg of 4arm-20kPEG-CM-Gly-N-R848 on the first dosing day (dosing day 0) at a tumor size 50-150 mm³. The same mice were also dosed intravenously with RSLAIL-2 at a dose of 0.8 mg/kg on days 0, 9 and 18 (i.e., they were dosed for a total of 3 doses, 9 days apart).

Group labeled "vehicle": mice were dosed intra-/peritumorally with 40 µl Hank's buffered saline (vehicle of 4-arm-PEG20k-CM-Gly-N-R848) on the first dosing day (dosing day 0) at tumor size ranging from 50-150 mm³. Same mice were also dosed intravenously with RSLAIL-2 vehicle buffer on days 0, 9 and 18, a total of 3 doses that were 9 days apart, starting on dosing day 0.

Measurements: Tumor volumes were collected by caliper measurements 2-3 times per week for 105 days and calculated using formula: L×W²/2 where L is tumor length and W is tumor width.

Results: Data is provided in Table 12.

TABLE 12

| Survival Proportions | | |
| --- | --- | --- |
| Days after treatment start | Vehicle | 4-arm-PEG20k-CM-Gly-N-R848 + RSLAIL-2 |
| 0 | ++++ | ++++ |
| 7 | ++++ | ++++ |
| 14 | ++++ | ++++ |
| 21 | ++++ | ++++ |
| 28 | ++++ | ++++ |
| 35 | ++++ | ++++ |

TABLE 12-continued

Survival Proportions

| Days after treatment start | Vehicle | 4-arm-PEG20k-CM-Gly-N-R848 + RSLAIL-2 |
|---|---|---|
| 38 | +++ | ++++ |
| 42 | +++ | ++++ |
| 45 | ++ | ++++ |
| 49 | ++ | ++++ |
| 52 | ++ | ++++ |
| 56 | + | ++++ |
| 59 | none | +++ |
| 63 | | +++ |
| 70 | | +++ |
| 73 | | +++ |
| 77 | | +++ |
| 80 | | +++ |
| 84 | | +++ |
| 91 | | +++ |
| 94 | | +++ |
| 98 | | +++ |
| 105 | | +++ |

Survival percentages are provided as follows:
0%≤+<25%
25%≤++<50%
50%≤+++<75%
75%≤++++<100%

Double agent treatment with RSLAIL-2+4-arm-PEG20k-CM-Gly-N-R848 resulted in survival of 50% of the animals by the end of the study at day 105 after commencement of dosing. Significantly, 40% of animals in the RSLAIL-2+4-arm-PEG20k-CM-Gly-N-R848 treatment group had complete responses, meaning no measurable tumors were observed by the end of the study.

The vehicle group had no surviving animals. All animals were removed from study due to reaching limiting tumor volume between days 28 and 56.

Example 31

In Vitro Studies: Activation of TLR by 4-arm-PEG20k-CM-Gly-N-N-R848 and Related Compounds Resiquimod and an exemplary long-acting TLR agonist, 4-arm-PEG20k-CM-Gly-N-N-R848 (Compound 6), were comparatively tested for initiating a transcriptional response downstream of human (h)TLR7, hTLR8 and hTLR4 in a dose response experiment.

The test systems used were reporter gene cell lines in HEK293 cells stably transfected with human TLR receptors and a secreted alkaline phosphatase (SEAP) reporter construct downstream of minimal IFNβ promoter fused to five NFkB and AP-1 binding sites (hTLR7 and hTLR8 cell lines) or IL-12 p40 minimal promoter fused to five NFkB and AP-1 binding sites (hTLR4 cell line). Parental cell lines (Null1 and Null1K, stably transfected with the SEAP reports but without hTLR receptor expression) were used as negative controls.

As shown in Table 13, resiquimod and Compound 6 activated reporter expression in hTLR7 and hTLR8 expressing cell lines but not in the hTLR4 cell line. LPS, a known hTLR4 ligand, specifically activated reporter expression the hTLR4 cell line. These data indicate that resiquimod specifically activated hTLR7 and hTLR8 signaling. Compound 6 also specifically activated reporter expression downstream hTLR7 and hTLR8 but at a >20 fold higher concentration compared to resiquimod and had no effect on hTLR4.

Since resiquimod is a known TLR 7/8 agonist, response in hTLR7 and hTLR8 but not hTLR4 expressing cell lines was expected. These experiments demonstrated that Compound 6 is poorly active and suggest that release of resiquimod is required for effective receptor agonism.

These data demonstrate that Compound 6 is a prodrug of resiquimod, and that conjugation to PEG via a releasable linker greatly attenuates the activity of resiquimod. This conclusion is further supported by Compound 6 and resiquimod activity comparison in primary blood monocytes in PBMC cultures.

TABLE 13

Summary of hTLR Activation by Compound 6, Resiquimod and LPS.

| TLR reporter cell line | Test Compound Experiment No. | R848 $EC_{50}$ (μM) | Compound 6 $EC_{50}$ (μM) | LPS $EC_{50}$ (ng/mL) |
|---|---|---|---|---|
| hTLR7 | Experiment 1 | 0.077 | 4.6 | NT* |
| | Experiment 2 | 0.040 | 3.5 | NT |
| | Experiment 3 | 0.092 | 4.8 | NT |
| | Mean | 0.070 | 4.3 | NT |
| | SD | 0.026 | 0.77 | NT |
| hTLR8 | Experiment 1 | 0.50 | >30 | NT |
| | Experiment 2 | 0.45 | >30 | NT |
| | Experiment 3 | 0.48 | >30 | NT |
| | Mean | 0.48 | >30 | NT |
| | SD | 0.027 | — | NT |
| hTLR4 | Experiment 1 | NA | NA | 0.095 |
| Null1 | Experiment 1 | NA | NA | NT |
| Null1K | Experiment 1 | NA | NA | NT |

*NT = not tested,
** NA = no activation of TLR pathway detected

Example 32

Analysis of Plasma Cytokine Induction After Compound 6 or Resiquimod Treatment in Combination with Staggered RSLAIL-2 Administration in Mouse Colon Carcinoma Model CT26 in BALB/c Mice Balb/c mice (n=6/group) bearing two CT26 subcutaneous tumors (100-200 mm3), one on each flank, were administered a single intra/peritumoral fixed dose of either resiquimod (10 μg) or an exemplary long-acting TLR agonist, 4-arm-PEG20k-CM-Gly-N-N-R848 (Compound 6) (1 μg or 10 μg) into the anatomical right side tumor. Half of these mice (n=3/group) received a single intravenous dose of an illustrative long acting IL-2Rβ-biased agonist, RSLAIL-2, of 0.8 mg/kg 96 hrs after Compound 6 or resiquimod administration enabling comparison between resiquimod and Compound 6 as single agents or in combination with RSLAIL-2. The concentration of proinflammatory cytokines IFNα, IFNγ, TNFα, IL-6 and IL-12 was determined in plasma by multiplex protein measurement assay at indicated time points post dose.

The lower Compound 6 dose level (1 μg) showed very modest induction of all cytokines in plasma. However, the 10 μg intra/peritumoral doses of resiquimod and Compound 6 both showed robust pro-inflammatory cytokine induction in blood. Both compounds showed similar transient induction patterns for all the cytokines examined with a rapid induction leading to peak levels at 2 hrs for IFNα, TNFα, IL-6, and IL-12 and a delayed peak for IFN-γ at 6 hrs after administration. Cytokine levels subsided to near background levels by 24 hrs.

A key difference between resiquimod and Compound 6, however, was observed in the magnitude of induction for all the cytokines measured with the exception of TNFα. The difference in peak cytokine levels induced by resiquimod compared to Compound 6 varied from 8 to10-fold (IL-6, IFNα) higher to 3 to 4-fold (IFNγ, IL-12) higher. Administration of RSAIL-2 four days after Compound 6 or resiquimod induced modest elevation of IFNα, TNF- and IL-12 in plasma. IFNγ however was induced to higher levels by RSLAIL-2 than by single-agent resiquimod or Compound 6 at the start of the treatment. Plasma IFNγ levels remained high (>100 pg/ml) for 3 days, which represented the last sampling time.

In summary, in side-by-side comparison at equivalent resiquimod dose levels, Compound 6 showed reduced plasma cytokine induction compared to unconjugated resiquimod after intra/peritumoral delivery. The addition of RSLAIL-2 to treatment with Compound 6 significantly induced only one of the measured cytokines, IFNγ, indicating largely non-overlapping cytokine induction profile for the two treatment agents.

Example 33

Flow Cytometry Evaluation of Immune Cell Pharmacodynamics Induced by Intra/Peritumorally Administered TLR Agonist and Intravenous RSLAIL-2 in CT26 Tumor Model Balb/c mice (n=3/group) bearing bilateral CT26 subcutaneous tumors, one on each flank, were administered a single intra/peritumoral dose of an exemplary long-acting TLR agonist, 4-arm-PEG20k-CM-Gly-N-N-R848 (Compound 6) (10 μg or 0.1 μg) in the anatomical right side tumor or vehicle. Four days after Compound 6 administration, an illustrative long acting IL-2Rβ-biased agonist, RSLAIL-2, (0.8 mg/kg) was delivered intravenously.

Treatment induced changes in immune cells locally in the Compound 6 treated tumors and abscopally in the contralateral untreated tumors and in blood were assessed by flow cytometry analysis. Tumors and blood were collected and processed for antibody staining one day and seven days after Compound 6 administration. This treatment and analysis scheme enabled the characterization of a rapid Compound 6 dose dependent single component activity, primarily in innate immune cell types including neutrophils and dendritic cells that are required for tumor antigen presentation to T cells. The second sampling time point of seven days after Compound 6 (three days after RSLAIL-2 treatment), showed how Compound 6 treatment dependently modulated later emerging RSLAIL-2 driven T cell responses in blood and tumors.

Early immunological events observed one day after treatment included an increase in intratumoral neutrophils at the higher 10 μg dose in the Compound 6 treated tumors, which coincided with increased cell death. Also coinciding with the neutrophil tumor infiltration was the transient activation of dendritic cells that showed upregulation of markers for maturation and lymph node homing in both treated and abscopal tumors. Seven days after combination treatment start (3 days after RSLAIL-2 administration) neutrophils were increased in a Compound 6-dose dependent manner in treated tumors. A Compound 6-dependent effect on RSLAIL-2-induced tumor cell death was observed in both Compound 6-treated and untreated tumors, likely driven by the enhancement of RSLAIL-2 dependent increase of cytotoxic CD8+ T cells in both tumors.

Tumor associated monocytes were reduced in tumors after treatment, most significantly three days after RSLAIL-2 administration at the day 7 time point. Total numbers of macrophages as a fraction of live cells increased suggesting that increased cell death was selectively induced in tumor cells and not in leukocytes. The relative numbers of macrophages as a fraction of total leukocytes in tumors were reduced however after combination treatment.

The primary driver for the relative macrophage decrease in leukocyte was the substantial increase in tumor infiltrating T cells shown. CD8+ T cells showed a selective Compound 6-dose dependent increase in tumors after combination treatment with RSLAIL-2. The relative fraction of regulatory T cells decreased dramatically leading to a high CD8:Treg ratio. An increased fraction of tumor infiltrating CD8+ cytotoxic T cells displayed high CD44 surface expression and increase in PD-1+ CTLA-4+ dual-positivity suggesting high antigen specific activity in the tumor environment.

Unlike in treated tumors, cell viability and neutrophil numbers were not affected in the blood. Monocytes were initially transiently increased in a dose dependent manner in the blood after Compound 6 treatment but reduced in the blood after RSLAIL-2 treatment compared to vehicle. Blood NK cells showed a slight increase in response to the high Compound 6 dose. However, significantly higher NK cell increase was apparent after RSLAIL-2 treatment. Compared to the tumor environment, T cells in the blood showed a markedly different response to treatment with the most striking difference being a significant increase in regulatory T cells after RSLAIL-2 treatment. Only a modest increase was observed in blood CD8+ T cell population in the higher Compound 6 dose group after RSLAIL-2 administration. CD4+ T cells showed marginal dose-dependent transient increase after Compound 6 administration but no significant response was observed after RSLAIL-2 administration. Importantly, both treatment groups showed an overall reduction of CD8:Treg ratio in the blood, unlike the dramatic dose dependent CD8:Treg increase observed in tumors.

While displaying only modest increase in abundance, a clear upregulation of activation markers and inhibitory feedback checkpoint receptors was observed in the examined T cell subpopulations in blood. CD25 expression was upregulated on regulatory T cells in blood in response to RSLAIL-2 treatment consistent with engagement of the IL-2 receptor and the observed increase in abundance. CD4+ T cells induced expression of the CD69 activation marker at the high dose of Compound 6 and in both drug treatment groups after RSLAIL-2 administration. CD8+ T cells showed a robust increase in CD25 expression in response to RSLAIL-2 administration and a transient CD69 upregulation in response to high Compound 6 dose. The CD44 expressing fraction of CD8+ T cells showed a Compound 6 dose dependent increase after RSLAIL-2 administration. Inhibitory checkpoint receptors PD-1 and CTLA-4 followed the same induction pattern as activation markers CD25, CD69 and CD44 on CD8+ T cells suggesting tumor antigen dependent activation.

These data support a model where an illustrative combination therapy with a long-acting TLR agonist and a long acting IL-2Rβ-biased agonist such as Compound 6 and RSLAIL-2, respectively, leads to sequential activation of innate and adaptive immune cell types optimizing the tumor antigen specific intratumoral accumulation and activity of cytotoxic T cells.

Innate immunity was activated by locally delivered Compound 6 driving tumor antigen release by neutrophils and presentation by dendritic cells to prime CD8+ T lymphocytes which were then greatly amplified by the RSLAIL-2 component of the treatment leading to a large systemic intratumoral increase of a tumor antigen specific active CD8+ T cell population.

INCORPORATION BY REFERENCE

All articles, books, patents, patent publications and other publications referenced herein are incorporated by reference in their entireties. In the event of an inconsistency between the teachings of this specification and the art incorporated by reference, the meaning of the teachings in this specification shall prevail.

It is claimed:

1. A conjugate comprising a Toll-like receptor 7/8 (TLR 7/8) agonist covalently attached, via a linkage-containing spacer moiety, to a multi-arm, water-soluble, non-peptidic polymer having a formula in accordance with Formula III:

(Formula III)

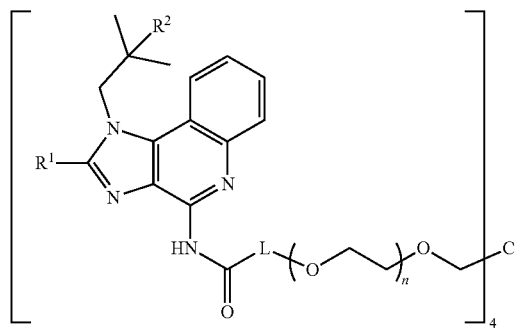

or a pharmaceutically acceptable salt or stereoisomer thereof, wherein:

L is —$(CH_2)_m$—, —$(CH_2)_m$—NH—C(O)—$(CH_2)_m$—, —CHF—$(CH_2)_m$—NH—C(O)—$(CH_2)_m$—, —$CH(CH_3)$—NH—C(O)—$(CH_2)_m$—, —$CH(CH(CH_3)_2)$—NH—C(O)—$(CH_2)_m$—, —$CH(CH_2CH(CH_3)_2)$—NH—C(O)—$(CH_2)_m$—, —$C(CH_3)_2$—NH—C(O)—$(CH_2)_m$—, a single bond, or —NH—$(CH_2)_m$—, each m is independently an integer from 1 to 5, inclusive;

each n is independently an integer from 40 to 350, inclusive;

$R^1$ is hydrogen or —$CH_2$—O—$CH_2$—$CH_3$; and $R^2$ is hydrogen or hydroxyl.

2. The conjugate of claim 1, wherein L is —$CH_2$—, —$CH_2$—$CH_2$—NH—C(O)—$CH_2$—, —$CH_2$—$CH_2$—$CH_2$—, —CHF—$CH_2$—NH—C(O)—$CH_2$—, —$CH_2$—NH—C(O)—$CH_2$—, —$CH(CH_3)$—NH—C(O)—$CH_2$—, —$CH(CH(CH_3)_2)$—NH—C(O)—$CH_2$—, —$CH(CH_2CH(CH_3)_2)$—NH—C(O)—$CH_2$—, —$C(CH_3)_2$—NH—C(O)—$CH_2$—, a single bond, or —NH—$CH_2$—$CH_2$—.

3. The conjugate of claim 1, wherein each n is independently an integer from 100 to 250, inclusive.

4. The conjugate of claim 1, wherein $R^1$ is hydrogen and $R^2$ is hydrogen.

5. The conjugate of claim 1, wherein $R^1$ is —$CH_2$—O—$CH_2$—$CH_3$ and $R^2$ is hydroxyl.

6. A conjugate selected from the group consisting of Compounds 1-10 and 12-15:

Compound 1

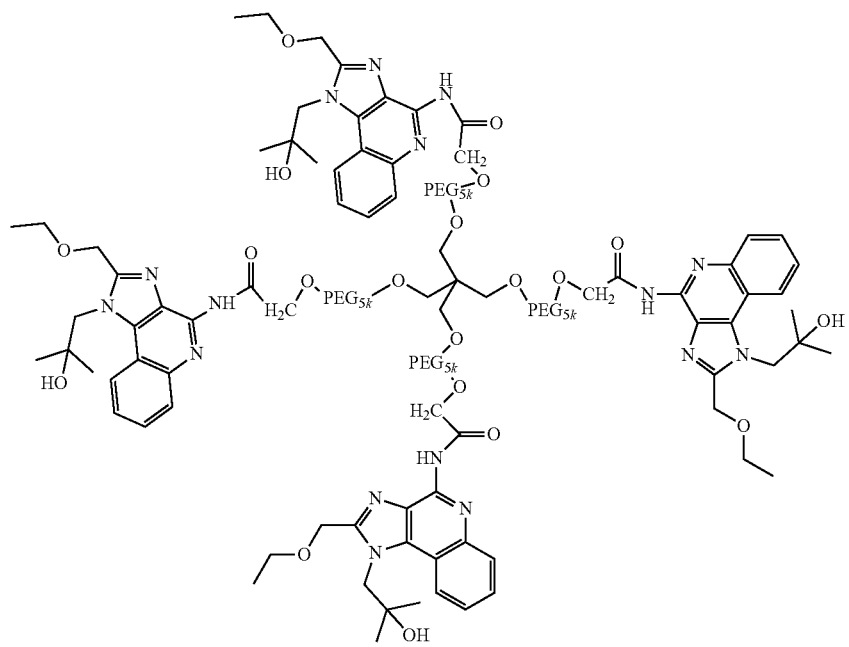

-continued
Compound 2
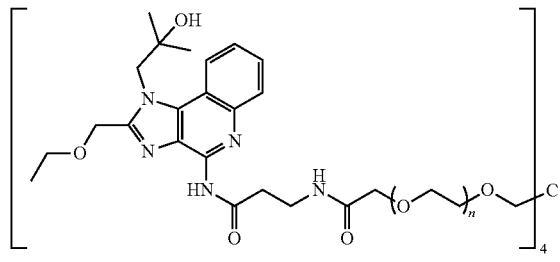
Compound 3
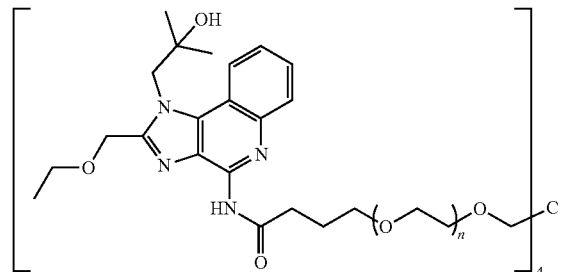
Compound 4
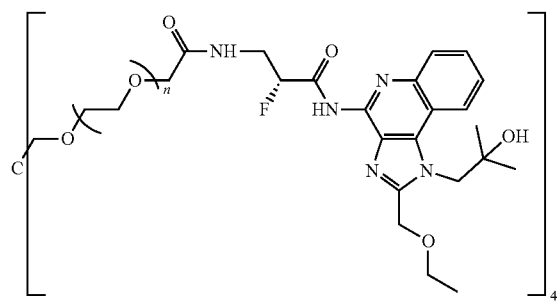
Compound 5
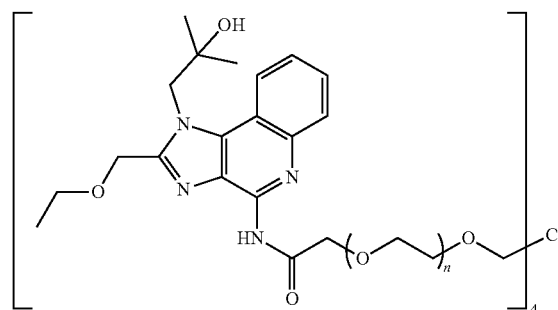
Compound 6
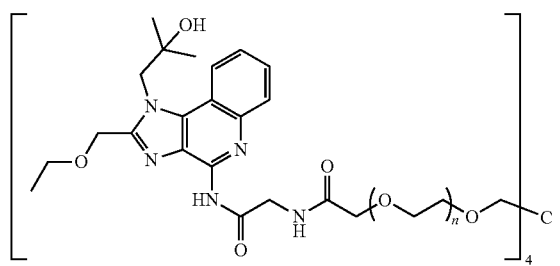
Compound 7
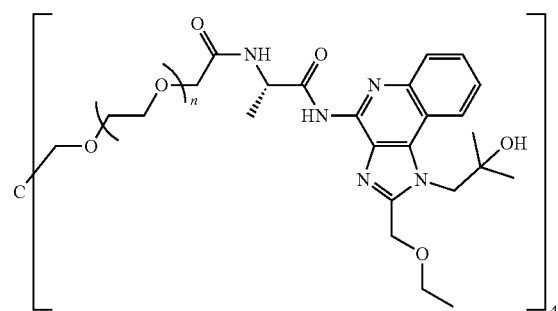
Compound 8
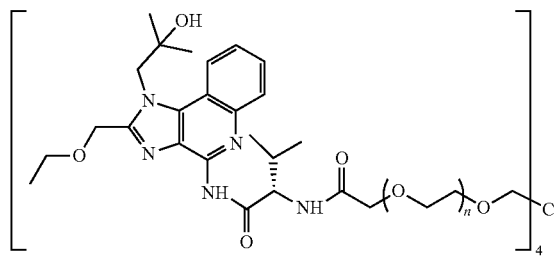
Compound 9
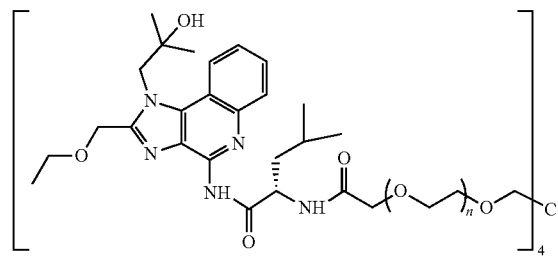
Compound 10
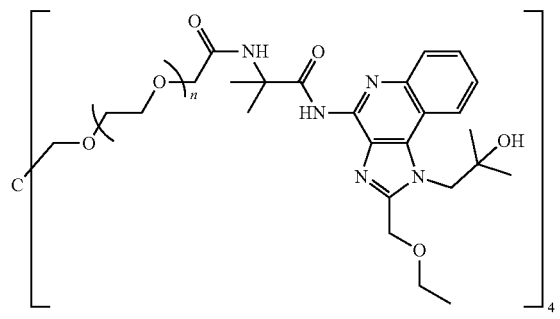
Compound 12
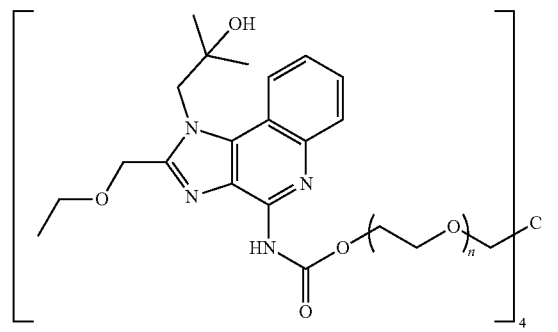

-continued

Compound 13

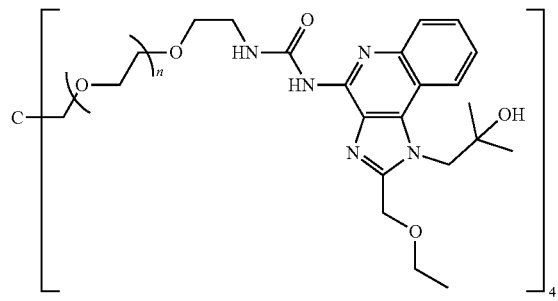

Compound 14

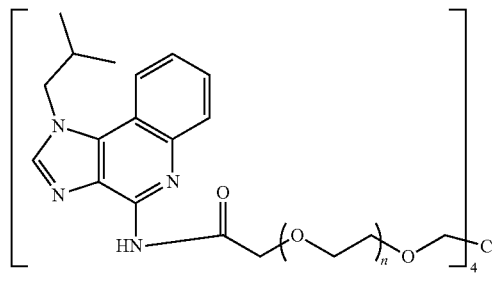

Compound 15

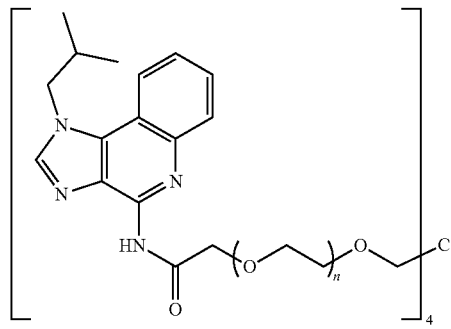

or a pharmaceutically acceptable salt or stereoisomer thereof, wherein each n is independently an integer from 40 to 350.

7. A composition comprising the conjugate of claim 1 and a pharmaceutically acceptable excipient.

8. The conjugate of claim 1, wherein n has a value corresponding to a weight average molecular weight of the poly(ethylene glycol) polymer selected from about 2,000 Daltons to about 150,000 Daltons, about 5,000 Daltons to about 40,000 Daltons, or about 5,000 Daltons to about 25,000 Daltons.

* * * * *